(12) United States Patent
Ding et al.

(10) Patent No.: US 9,815,841 B2
(45) Date of Patent: Nov. 14, 2017

(54) COMPOUNDS

(71) Applicant: GLAXOSMITHKLINE INTELLECTUAL PROPERTY DEVELOPMENT LIMITED, Brentford, Middlesex (GB)

(72) Inventors: Xiao Ding, Shanghai (CN); Qian Liu, Shanghai (CN); Kai Long, Shanghai (CN); Yingxia Sang, Shanghai (CN); Luigi Piero Stasi, Shanghai (CN); Zehong Wan, Shanghai (CN); Qiongfeng Xu, Shanghai (CN); Colin Michael Edge, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/114,857

(22) PCT Filed: Jan. 28, 2015

(86) PCT No.: PCT/CN2015/000054
§ 371 (c)(1),
(2) Date: Jul. 28, 2016

(87) PCT Pub. No.: WO2015/113451
PCT Pub. Date: Aug. 6, 2015

(65) Prior Publication Data
US 2017/0022204 A1  Jan. 26, 2017

(30) Foreign Application Priority Data
Jan. 29, 2014 (WO) ............... PCT/CN2014/000140

(51) Int. Cl.
| A61K 31/519 | (2006.01) |
| C07D 487/04 | (2006.01) |
| A61K 31/437 | (2006.01) |
| A61K 31/4375 | (2006.01) |
| C07D 519/00 | (2006.01) |

(52) U.S. Cl.
CPC .......... *C07D 487/04* (2013.01); *A61K 31/437* (2013.01); *A61K 31/4375* (2013.01); *C07D 519/00* (2013.01)

(58) Field of Classification Search
CPC ............................ C07D 487/04; A61K 31/519
USPC .......................................... 544/280; 514/258
See application file for complete search history.

(56) References Cited

U.S. PATENT DOCUMENTS

| 7,855,205 B2 | 12/2010 | Huang et al. |
| 7,998,978 B2 | 8/2011 | Huang et al. |
| 9,156,775 B2 | 10/2015 | Thiele et al. |
| 9,315,449 B2 | 4/2016 | Thiele et al. |
| 9,353,116 B2 | 5/2016 | Garske et al. |
| 2005/0070542 A1 | 3/2005 | Hodgetts et al. |
| 2007/0275984 A1 | 11/2007 | Imogai et al. |
| 2008/0004295 A1* | 1/2008 | Gore .................... C07D 487/04 514/265.1 |
| 2009/0325964 A1 | 12/2009 | Bursavich et al. |
| 2012/0094999 A1 | 4/2012 | Gray et al. |
| 2012/0122838 A1 | 5/2012 | Ren et al. |
| 2012/0165329 A1 | 6/2012 | Ibrahim et al. |
| 2013/0079324 A1 | 3/2013 | Cheng et al. |
| 2014/0018540 A1 | 1/2014 | Sheridan et al. |
| 2014/0031547 A1 | 1/2014 | Sheridan et al. |
| 2015/0209368 A1 | 7/2015 | Sheridan et al. |
| 2016/0058745 A1 | 3/2016 | Sheridan et al. |

FOREIGN PATENT DOCUMENTS

| CN | 102482277 A | 5/2012 |
| CN | 103492389 A | 1/2014 |
| WO | WO2009/036066 | 3/2009 |
| WO | 2010129053 A1 | 11/2010 |
| WO | 2011038572 A1 | 4/2011 |
| WO | WO2012/009258 | 1/2012 |
| WO | WO2012/045195 | 4/2012 |
| WO | 2012062783 A1 | 5/2012 |
| WO | WO2012/143144 | 10/2012 |
| WO | 2013042006 A1 | 3/2013 |
| WO | 2013079496 A1 | 6/2013 |
| WO | WO2013/139882 | 9/2013 |
| WO | 2013164321 A1 | 11/2013 |
| WO | 2013164323 A1 | 11/2013 |
| WO | WO2014/001973 | 1/2014 |
| WO | 2015113452 A1 | 8/2015 |

OTHER PUBLICATIONS

Chan et al., Discovery of a Highly Selective, Brain-Penetrant Aminopyrazole LRRK2 Inhibitor. ACS Med Chem Lett. Nov. 23, 2012;4(1):85-90.
Deng et al., Leucine-rich repeat kinase 2 inhibitors: a patent review (2006-2011). Expert Opin Ther Pat. Dec. 2012; 22 (12):1415-26.
Estrada et al., Discovery of highly potent, selective, and brain-penetrable leucine-rich repeat kinase 2 (LRRK2) small molecule inhibitors. J Med Chem. Nov. 26, 2012;55(22):9416-33.
Estrada et al., Discovery of highly potent, selective, and brain-penetrant aminopyrazole leucine-rich repeat kinase 2 (LRRK2) small molecule inhibitors. J Med Chem. Feb. 13, 2014;57(3):921-36.
Kethiri et al., Leucine-rich repeat kinase 2 inhibitors: a review of recent patents (2011-2013). Expert Opin Ther Pat. Jul. 24, 2014; (7):745-57.
Extended European Search Report 15743645.2 dated May 15, 2017.
Extended European Search Report 15743797.1 dated May 15, 2017.

\* cited by examiner

*Primary Examiner* — Charanjit Aulakh
(74) *Attorney, Agent, or Firm* — Feng Xu; William R. Majarian

(57) ABSTRACT

The present invention relates to novel compounds that inhibit LRRK2 kinase activity, processes for their preparation, to compositions containing them and to their use in the treatment of or prevention of diseases characterized by LRRK2 kinase activity, for example Parkinson's disease, Alzheimer's disease and amyotrophic lateral sclerosis (ALS).

13 Claims, No Drawings

COMPOUNDS

This application is a 371 of International Application No. PCT/CN2015/000054, filed 28 Jan. 2015, which claims priority to PCT/CN2014/000140, filed 29 Jan. 2014.

RELATED APPLICATION

The present application claims priority from PCT International Application No. PCT/CN2014/000140 filed on Jan. 29, 2014 at the State Intellectual Property Office of the People's Republic of China, the entire contents of which is incorporated herein by reference.

FIELD OF THE INVENTION

The present invention relates to novel compounds that inhibit LRRK2 kinase activity, processes for their preparation, compositions containing them and their use in the treatment of diseases characterized by LRRK2 kinase activity, for example, Parkinson's disease, amyotrophic lateral sclerosis (ALS) and Alzheimer's disease.

BACKGROUND OF THE INVENTION

Parkinson's disease (PD) is a neurodegenerative disorder characterized by selective degeneration and cell death of dopaminergic neurons in the substantial nigra region of the brain. Parkinson's disease was generally considered to be sporadic and of unknown etiology, but, in the last 15 years, there has been an important development of the understanding of the genetic basis of this disease and associated pathogenic mechanisms. One area of the development is the understanding of leucine rich repeat kinase 2 (LRRK2) protein. A number of mis-sense mutations in the LRRK2 gene have been strongly linked with autosomal dominant Parkinson's disease in familial studies (See WO2006068492 and WO2006045392; Trinh and Farrer 2013, Nature Reviews in Neurology 9: 445-454; Paisan-Ruiz et al., 2013, J. Parkinson's Disease 3: 85-103). The G2019S mutation in LRRK2 is the most frequent mis-sense mutation and is associated with a clinical phenotype that closely resembles sporadic Parkinson's disease. The LRRK2 G2019S mutation is also present in approximately 1.5% of sporadic Parkinson's disease cases (See Gilks et al., 2005, Lancet, 365: 415-416). In addition to the known pathogenic coding mutations in LRRK2, additional amino acid coding variants of LRRK2 have been identified that are also associated with risk of developing Parkinson's disease (See Ross et al., 2011 Lancet Neurology 10: 898-908). Furthermore, genome-wide association studies (GWAS) have identified LRRK2 as a Parkinson's disease susceptibility locus, which indicates that LRRK2 may be also relevant to sporadic Parkinson's disease cases without mutations that cause amino acid substitutions in the LRRK2 protein. (See Satake et al., 2009 Nature Genetics 41:1303-1307; Simon-Sanchez et al 2009 Nature Genetics 41: 1308-1312)

LRRK2 is a member of the ROCO protein family and all members of this family share five conserved domains. The most common pathogenic mutation G2019S occurs in the highly conserved kinase domain of LRRK2. This mutation confers an increase in the LRRK2 kinase activity in in vitro enzyme assays of recombinant LRRK2 proteins (See Jaleel et al., 2007, Biochem J, 405: 307-317) and in LRRK2 proteins purified from G2019S PD patient-derived cells (See Dzamko et al., 2010 Biochem. J. 430: 405-413). A less frequent LRRK2 pathogenic mutation that confers amino acid substitution at a different residue, R1441, has also been shown to elevate LRRK2 kinase activity by decreasing the rate of GTP hydrolysis by the GTPase domain of LRRK2 (See Guo et al., 2007 Exp Cell Res. 313: 3658-3670; West et al., 2007 Hum. Mol Gen. 16: 223-232). Therefore, the evidence indicates that the kinase and GTPase activities of LRRK2 are important for pathogenesis, and that the LRRK2 kinase domain may regulate overall LRRK2 function (See Cookson, 2010 Nat. Rev. Neurosci. 11: 791-797).

There is evidence to show that the increased LRRK2 kinase activity is associated with neuronal toxicity in cell culture models (See Smith et al., 2006 Nature Neuroscience 9: 1231-1233) and kinase inhibitor compounds protect against LRRK2-mediated cell death (See Lee et al., 2010 Nat. Med. 16: 998-1000).

Induced pluripotent stem cells (iPSCs) derived from LRRK2 G2019S Parkinson's disease patients have been found to exhibit defects in neurite outgrowth and increased susceptibility to rotenone, that may be ameliorated by either genetic correction of the G2019S mutation or treatment of cells with small molecule inhibitors of LRRK2 kinase activity (See Reinhardt et al., 2013 Cell Stem Cell 12: 354-367). Increased mitochondrial damage associated with LRRK2 G2019S mutation in iSPCs is also blocked by genetic correction of the G2019S mutation (See Sanders et al., 2013 Neurobiol. Dis. 62: 381-386).

Additional evidence links LRRK2 function and dysfunction with autophagy-lysosomal pathways (See Manzoni and Lewis, 2013 Faseb J. 27:3234-3429). LRRK2 proteins confer defects in chaperone-mediated autophagy that negatively impact the ability of cells to degrade alpha-synuclein (Orenstein et al., 2013 Nature Neurosci. 16 394-406). In other cell models, selective LRRK2 inhibitors have been shown to stimulate macroautophagy (See Manzoni et al., 2013 BBA Mol. Cell Res. 1833: 2900-2910). These data suggest that small molecule inhibitors of LRRK2 kinase activity may have utility in the treatment of diseases characterized by defects in cellular proteostasis that result from aberrant autophagy/lysosomal degradation pathways including forms of Parkinson's disease associated with GBA mutations (See Swan and Saunders-Pullman 2013 Curr. Neurol. Neurosci Rep. 13: 368), other alpha-synucleinopathies, tauopathies, Alzheimer's disease (See Li et al., 2010 Neurodegen. Dis. 7: 265-271) and other neurodegenerative diseases (See Nixon 2013 Nat. Med. 19: 983-997) and Gaucher disease (See Westbroek et al., 2011 Trends. Mol. Med. 17: 485-493). Further, significantly elevated levels of LRRK2 mRNA have also been observed in fibroblasts of Niemann-Pick Type C (NPC) disease patients compared with fibroblasts of normal subjects, which indicates that aberrant LRRK2 function may play a role in lysosomal disorders (See Reddy et al., 2006 PLOS One 1 (1):e19 doi: 10.1371/journal.pone.0000019—supporting information Dataset 51). This observation suggests that LRRK2 inhibitors may have utility for treatment of NPC.

The PD-associated G2019S mutant form of LRRK2 has also been reported to enhance phosphorylation of tubulin-associated Tau (See Kawakami et al., 2012 PLoS ONE 7: e30834, doi 10.1371), and disease models have been proposed in which LRRK2 acts upstream of the pathogenic effects of Tau and alpha-synuclein (See Taymans & Cookson, 2010, BioEssays 32: 227-235). In support of this, LRRK2 expression has been associated with increased aggregation of insoluble Tau, and increased Tau phosphorylation, in a transgenic mouse model (See Bailey et al., 2013 Acta Neuropath. 126:809-827). Over-expression of the PD pathogenic mutant protein LRRK2 R1441G is reported to cause symptoms of Parkinson's disease and hyperphosphorylation of Tau in transgenic mouse models (See Li, Y. et al. 2009, Nature Neuroscience 12: 826-828). Therefore, these data suggest that LRRK2 inhibitors of kinase catalytic activity may be useful for the treatment of tauopathy diseases characterized by hyperphosphorylation of Tau such as argyrophilic grain disease, Pick's disease, corticobasal degeneration, progressive supranuclear palsy and inherited frontotemporal dementia and parkinsonism linked to chromosome 17 (FTDP-17) (See Goedert, M and Jakes, R (2005) Biochemica et Biophysica Acta 1739, 240-250). In addition, LRRK2 inhibitors may have utility in treatment of other diseases characterized by diminished dopamine levels such as withdrawal symptoms/relapse associated with drug addiction (See Rothman et al., 2008, Prog. Brain Res, 172: 385).

Other studies have also shown that overexpression of the G2019S mutant form of LRRK2 confers defects in subventricular zone (SVZ) neuroprogenitor cell proliferation and migration in transgenic mouse models (See VVinner et al., 2011 Neurobiol. Dis. 41: 706-716) and reduces neurite length and branching cell culture models (See Dachsel et al., 2010 Parkinsonism & Related Disorders 16: 650-655). Moreover, it was reported that agents that promote SVZ neuroprogenitor cell proliferation and migration also improve neurological outcomes following ischemic injury in rodent models of stroke (See Zhang et al., 2010 J. Neurosci. Res. 88: 3275-3281). These findings suggest that compounds that inhibit aberrant activity of LRRK2 may have utility for the treatments designed to stimulate restoration of CNS functions following neuronal injury, such as ischemic stroke, traumatic brain injury, spinal cord injury.

Mutations in LRRK2 have also been identified that are clinically associated with the transition from mild cognitive impairment (MCI) to Alzheimer's disease (See WO2007149798). These data suggest that inhibitors of LRRK2 kinase activity may be useful for the treatment diseases such as Alzheimer's disease, other dementias and related neurodegenerative disorders.

Aberrant regulation of normal LRRK2 proteins is also observed in some disease tissues and models of disease. Normal mechanisms of translational control of LRRK2 by miR-205 are perturbed in some sporadic PD cases, where significant decreases in miR-205 levels in PD brain samples concur with elevated LRRK2 protein levels in those samples (See Cho et al., (2013) Hum. Mol. Gen. 22: 608-620). Therefore, LRRK2 inhibitors may be used in treatment of sporadic PD patients who have elevated levels of normal LRRK2 proteins.

In an experimental model of Parkinson's disease in marmosets, an elevation of LRRK2 mRNA is observed in a manner that correlates with the level of L-Dopa induced dyskinesia (See Hurley, M. J et al., 2007 Eur. J. Neurosci. 26: 171-177). This suggests that LRRK2 inhibitors may have a utility in amelioration of such dyskinesias.

Significantly elevated levels of LRRK2 mRNA have been reported in ALS patient muscle biopsy samples (See Shtilbans et al., 2011 Amyotrophic Lateral Sclerosis 12: 250-256) It is suggested that elevated levels of LRRK2 kinase activity may be a characteristic feature of ALS. Therefore, this observation indicated that LRRK2 inhibitor may have utility for treatment of ALS.

There is also evidence indicating that LRRK2 kinase activity may play a role in mediating microglial proinflammatory responses (See Moehle et al., 2012, J. Neuroscience 32: 1602-1611). This observation suggests a possible utility of LRRK2 inhibitors for treatment of aberrant neuroinflammatory mechanisms that contribute a range of neurodegenerative diseases, including Parkinson's disease, Alzheimer's disease, multiple sclerosis, HIV-induced dementia, amyotrophic lateral sclerosis, ischemic stroke, traumatic brain injury and spinal cord injury. Some evidence also indicates that LRRK2 plays a role in regulating neuronal progenitor differentiation in vitro (See Milosevic, J. et al., 2009 Mol. Neurodegen. 4: 25). This evidence suggests that inhibitors of LRRK2 may have a utility in production of neuronal progenitor cells in vitro for consequent therapeutic application in cell based-treatment of CNS disorders.

It has been reported that Parkinson's disease patients bearing LRRK2 G2019S mutation display increased frequency of non-skin cancers, including renal, breast, lung, prostate cancers as well as acute myelogenous leukemia (AML). Since there is evidence to show that G2019S mutation in LRRK2 increases catalytic activity of the LRRK2 kinase domain, small molecule inhibitors of LRRK2 may have a utility in treatment of cancers, for example kidney cancer, breast cancer, lung cancer, prostate cancer (e.g. solid tumors) and blood cancer (See. AML; Saunders-Pullman et al., 2010, Movement Disorders, 25:2536-2541; Inzelberg et al., 2012 Neurology 78: 781-786). Amplification and over-expression of LRRK2 has also been reported in papillary renal and thyroid carcinomas, where co-operativity between LRRK2 and the MET oncogene may promote tumor cell growth and survival (See Looyenga et al., 2011 PNAS 108: 1439-1444.)

Some studies suggested that genetic association of common LRRK2 variants with susceptibility to ankylosing spondylitis (See Danoy P, et al., 2010. PLoS Genet.; 6(12): e1001195; and leprosy infection. (See Zhang F R, et al. 2009, N Engl J Med. 361:2609-18.) These findings suggest that inhibitors of LRRK2 may have a utility in the treatment of ankylosing spondylitis and leprosy infection.

Meta-analysis of three genome wide associated scans for Crohn's disease identified a number of loci associated with the disease, including the locus containing the LRRK2 gene (See Barrett et al., 2008, Nature Genetics, 40: 955-962). Evidence has also emerged that LRRK2 is an IFN-γ target gene that may be involved in signaling pathways relevant to Crohn's disease pathogenesis (See Gardet et al., 2010, J. Immunology, 185: 5577-5585). These findings suggest that inhibitors of LRRK2 may have utility in the treatment of Crohn's disease.

As an IFN-γ target gene, LRRK2 may also play a role in T cell mechanisms that underlie other diseases of the immune system such as multiple sclerosis and rheumatoid arthritis. Further potential utility of LRRK2 inhibitors comes from the reported finding that B lymphocytes constitute a major population of LRRK2 expressing cells (See Maekawa et al. 2010, BBRC 392: 431-435). This suggests that LRRK2 inhibitors may be effective in treatment of diseases of the immune system for which B cell depletion is, or may be, effective in diseases such as lymphomas, leukemias, multiple sclerosis (See Ray et al., 2011 J. Immunol. 230: 109), rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies (See Engel et al., 2011 Pharmacol. Rev. 63: 127-156; Homam et al., 2010 J. Olin. Neuromuscular Disease 12: 91-102).

SUMMARY OF THE INVENTION

The present invention provides, in a first aspect, a compound of Formula (I) or a pharmaceutically acceptable salt thereof Formula (I)

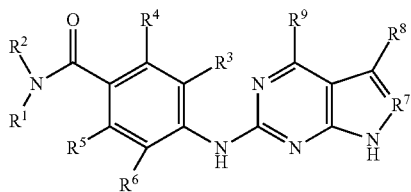

wherein
R¹ is H,
R² is $C_{1-5}$ alkyl optionally substituted with one or more hydroxyl, or
R¹ and R², together with the nitrogen to which they are attached, form:
(1) a nitrogen containing heterocyclic ring, wherein the heterocyclic ring is optionally substituted with one or more substituents independently selected from the group consisting of $C_{1-3}$alkyl, —$CH_2$—$OCH_3$, halo, and piperazin-1-yl optionally substituted with $C_{1-3}$alkyl on the nitrogen at the 4 position, or
(2) a bicyclic ring system selected from the group consisting of

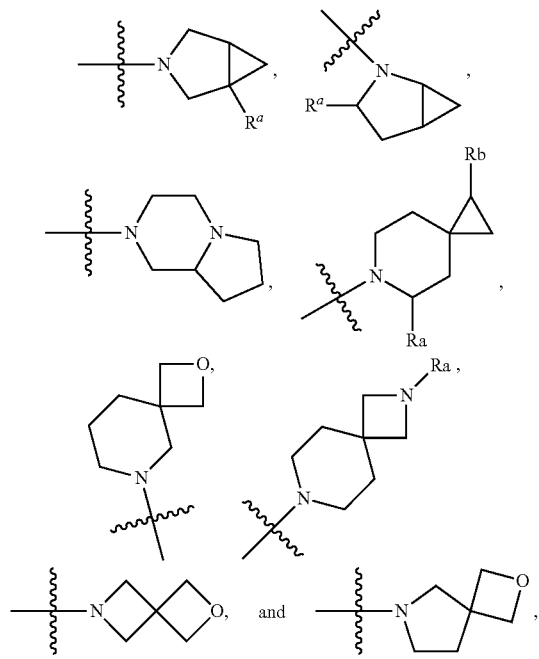

wherein each occurrence of $R^a$ and $R^b$ is independently selected from the group consisting of H, ON, halo, —$CH_2OCH_3$, $C_{1-3}$alkoxyl, and $C_{1-3}$alkyl optionally substituted with one hydroxy group;
$R^3$ and $R^6$ are each independently selected from the group consisting of H, $C_{1-3}$alkoxyl, —O—$C_{1-3}$haloalkyl, —O—$CH_2$—$C_{3-6}$cyclalkyl, halo, and —$NR^xR^y$, wherein $R^x$ and $R^y$ are each independently H or $C_{1-3}$alkyl;
$R^4$ and $R^5$ are each independently selected from the group consisting of H, halo, $C_{1-3}$alkoxy, and $C_{1-3}$alkyl,
$R^7$ is N or CH;
$R^8$ is selected from the group consisting of H, ON, $C_{1-3}$haloalkyl and $C_{1-3}$alkyl; and
$R^9$ is selected from the group consisting of $C_{1-3}$alkoxyl, $C_{1-3}$haloalkyl, —O—$C_{1-3}$haloalkyl, and —O—$CH_2$—$C_{3-6}$cycloalkyl,
with the proviso that the compound of Formula (I) is not N-propyl-4-[[4-[3,3,3-tris(fluoranyl)propyl]-7H-pyrrolo[2,3-d]pyrimidin-2-yl]amino]benzamide.

In a further aspect of the invention, the invention provides a pharmaceutical composition comprising a compound of Formula (I) or a pharmaceutically acceptable salt thereof and a pharmaceutically acceptable carrier.

A further aspect of the invention provides a compound of Formula (I) or a pharmaceutically acceptable salt thereof for use in the treatment or prevention of Parkinson's disease or Alzheimer's disease.

DETAILED DESCRIPTION OF THE INVENTION

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Generally, the nomenclature used herein and the laboratory procedures in organic chemistry, medicinal chemistry, biology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

All patents, patent applications and publications referred to herein are incorporated by reference in their entirety. In case of a conflict in terminology, the present specification is controlling.

A. Definitions

As used herein, "alkyl" refers to a monovalent, saturated hydrocarbon chain having a specified number of carbon atoms. For example, $C_{1-3}$ alkyl refers to an alkyl group having from 1 to 3 carbon atoms. $C_{1-5}$ alkyl refers to an alkyl group having from 1 to 5 carbon atoms. Alkyl groups may be straight or branched. In some embodiments, branched alkyl groups may have one, two, or three branches. Exemplary alkyl groups include, but are not limited to, methyl, methylethyl, ethyl, propyl (n-propyl and isopropyl), methylpropyl, butyl (n-butyl, isobutyl, and t-butyl), pentyl (n-pentyl, isopentyl, and neopentyl), and hexyl.

As used herein, "alkoxy" refers to the group —O-alkyl. For example, $C_{1-5}$ alkoxyl groups contain from 1 to 5 carbon atoms. $C_{1-3}$ alkoxyl groups contain from 1 to 3 carbon atoms. Exemplary alkoxy groups include, but are not limited to, methoxy, ethoxy, propoxy, butoxyl, and pentyloxy.

As used herein, "cycloalkyl" refers to a saturated monocyclic hydrocarbon ring of 3 to 10 carbon atoms. For example, $C_{3-6}$ cycloalkyl contains 3 to 6 carbon atoms as member atoms in the ring. Examples of cycloalkyl include cyclopropyl, cyclobutyl, cyclopentyl and cyclohexyl.

As used herein, "halogen" refers to fluorine (F), chlorine (Cl), bromine (Br), or iodine (I). "Halo" refers to the halogen radicals: fluoro (—F), chloro (—Cl), bromo (—Br), or iodo (—I).

As used herein, "haloalkyl" refers to an alkyl group, as defined above, having one or more halogen atoms selected from F, Cl, Br, or I, which are substituted on any or all of the carbon atoms of the alkyl group by replacing hydrogen atoms attached to the carbon atoms. For example, $C_{1-3}$haloalkyl refers to a $C_{1-3}$alkyl group substituted with one or more halogen atoms. In some embodiments, "haloalkyl" refers to an alkyl group substituted with one or more halogen atoms independently selected from F or Cl. Exemplary haloalkyl groups include, but are not limited to, chloromethyl, bromoethyl, trifluoromethyl, and dichloromethyl.

As used herein, "nitrogen containing heterocyclic ring" refers to a five or six-membered nitrogen containing monoheterocyclic ring which is saturated and which contains at least one nitrogen atom. Optionally, the heterocyclic ring may contain one or two hetero atoms each independently selected from O or N. Examples of nitrogen containing heterocyclic ring includes, but are not limited to, morpholine, piperazine, piperidine, oxazolidine, pyrrolidine and the like.

As used herein, "substituted" in reference to a group indicates that one or more hydrogen atom attached to a member atom (e.g., carbon atom) within the group is replaced with a substituent selected from the group of defined substituents. It should be understood that the term "substituted" includes the implicit provision that such substitution is in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom. Exemplary substituents include, but are not limited to, alkyl, alkoxyl, halo, haloalkyl, —CH$_2$OCH$_3$, OH, and heterocycloalkyl (e.g., piperazinyl). Suitable substituents are defined herein for each substituted or optionally substituted group.

As used herein, "optionally substituted" indicates that a group, such as alkyl, phenyl, pyrazol-4-yl, and alkoxyl may be unsubstituted, may be substituted with one or more substituent as defined.

As used herein, the term "disease" refers to any alteration in state of the body or of some of the organs, interrupting or disturbing the performance of the functions and/or causing symptoms such as discomfort, dysfunction, distress, or even death to the person afflicted or those in contact with a person. A disease can also include a distemper, ailing, ailment, malady, disorder, sickness, illness, complain, interdisposition and/or affectation.

As used herein, "treat", "treating" or "treatment" in reference to a disease means: (1) to ameliorate the disease or one or more of the biological manifestations of the disease, (2) to interfere with (a) one or more points in the biological cascade that leads to or is responsible for the disease or (b) one or more of the biological manifestations of the disease, (3) to alleviate one or more of the symptoms or effects associated with the disease, (4) to slow the progression of the disease or one or more of the biological manifestations of the disease, and/or (5) to diminish the likelihood of severity of a disease or biological manifestations of the disease.

As used herein, "prevent", "preventing" or "prevention" means the prophylactic administration of a drug to diminish the likelihood of the onset of or to delay the onset of a disease or biological manifestation thereof.

As used herein, "subject" means a mammalian subject (e.g., dog, cat, horse, cow, sheep, goat, monkey, etc.), and human subjects including both male and female subjects, and including neonatal, infant, juvenile, adolescent, adult and geriatric subjects, and further including various races and ethnicities including, but not limited to, white, black, Asian, American Indian and Hispanic.

As used herein, "pharmaceutically acceptable salt(s)" refers to salt(s) that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

As used herein, "therapeutically effective amount" in reference to a compound of the invention or other pharmaceutically-active agent means an amount of the compound sufficient to treat or prevent the patient's disease but low enough to avoid serious side effects (at a reasonable benefit/risk ratio) within the scope of sound medical judgment. A therapeutically effective amount of a compound will vary with the particular compound chosen (e.g. consider the potency, efficacy, and half-life of the compound); the route of administration chosen; the disease being treated; the severity of the disease being treated; the age, size, weight, and physical disease of the patient being treated; the medical history of the patient to be treated; the duration of the treatment; the nature of concurrent therapy; the desired therapeutic effect; and like factors, but can nevertheless be routinely determined by the skilled artisan.

As used herein, the terms "compound(s) of the invention" or "compound(s) of present invention" mean a compound of Formula (I), as defined above, in any form, i.e., any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

B. Compounds

This invention provides, in a first aspect, a compound of Formula (I) or a pharmaceutically acceptable salt thereof Formula (I)

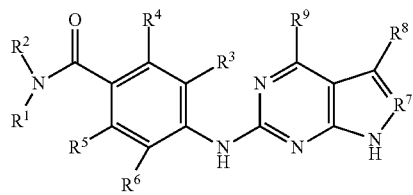

wherein
$R^1$ is H,
$R^2$ is $C_{1-5}$alkyl optionally substituted with one or more hydroxyl, or
$R^1$ and $R^2$, together with the nitrogen to which they are attached, form:
(1) a nitrogen containing heterocyclic ring, wherein the heterocyclic ring is optionally substituted with one or more substituents independently selected from the group consisting of $C_{1-3}$alkyl, —$CH_2$—$OCH_3$, halo, and piperazin-1-yl optionally substituted with $C_{1-3}$alkyl on the nitrogen at the 4 position, or
(2) a bicyclic ring system selected from the group consisting of

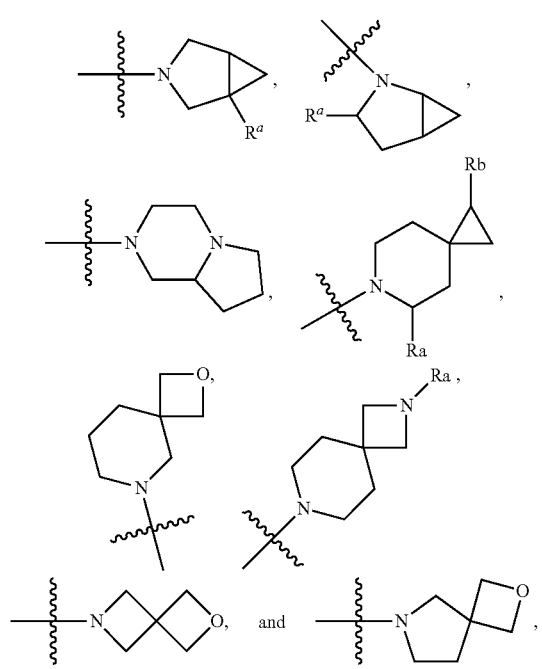

wherein each occurrence of $R^a$ and $R^b$ is independently selected from the group consisting of H, ON, halo, —$CH_2OCH_3$, $C_{1-3}$alkoxyl, and $C_{1-3}$alkyl optionally substituted with one hydroxy group;
$R^3$ and $R^6$ are each independently selected from the group consisting of H, $C_{1-3}$alkoxyl, —O—$C_{1-3}$haloalkyl, —O—$CH_2$—$C_{3-6}$cyclalkyl, halo, and —$NR^xR^y$, wherein $R^x$ and $R^y$ are each independently H or $C_{1-3}$alkyl;

$R^4$ and $R^5$ are each independently selected from the group consisting of H, halo, $C_{1-3}$alkoxy, and $C_{1-3}$alkyl,
$R^7$ is N or CH;
$R^8$ is selected from the group consisting of H, ON, $C_{1-3}$haloalkyl and $C_{1-3}$alkyl; and
$R^9$ is selected from the group consisting of $C_{1-3}$alkoxyl, $C_{1-3}$haloalkyl, —O—$C_{1-3}$haloalkyl, and —O—$CH_2$—$C_{3-6}$cycloalkyl,
with the proviso that the compound of Formula (I) is not N-propyl-4-[[4-[3,3,3-tris(fluoranyl)propyl]-7H-pyrrolo[2,3-d]pyrimidin-2-yl]amino]benzamide.

In one embodiment, this invention relates to compounds of Formula (I), wherein $R^1$ and $R^2$, together with the nitrogen to which they are attached, form a nitrogen containing heterocyclic ring, wherein the heterocyclic ring is optionally substituted with one or two substituents each independently selected from the group consisting of $C_{1-3}$alkyl, —$CH_2$—$OCH_3$, halo, and piperazine optionally substituted with $C_{1-3}$alkyl on the nitrogen, or pharmaceutically acceptable salts thereof. In one embodiment, this invention relates to compounds of Formula (I), wherein $R^1$ and $R^2$, together with the nitrogen to which they are attached, form a nitrogen containing heterocyclic ring, wherein the heterocyclic ring is optionally substituted with one or two substituents each independently selected from the group consisting of $C_{1-3}$alkyl and halo, or pharmaceutically acceptable salts thereof.

In a further embodiment, this invention relates to compounds of Formula (I), $R^1$ and $R^2$, together with the nitrogen to which they are attached, form a nitrogen containing heterocyclic ring, wherein the heterocyclic ring is selected from morpholine, piperazine or piperidine, optionally substituted with one or two substituents each independently selected from $C_{1-3}$alkyl, or pharmaceutically acceptable salts thereof. In yet a further embodiment, this invention relates to compounds of Formula (I), wherein $R^1$ and $R^2$, together with the nitrogen to which they are attached, form a nitrogen containing heterocyclic ring, wherein the heterocyclic ring is morpholine optionally substituted with one or two substituents each independently selected from $C_{1-3}$alkyl, or pharmaceutically acceptable salts thereof. In a further embodiment, this invention relates to compounds of Formula (I), wherein $R^1$ and $R^2$, together with the nitrogen to which they are attached, form a nitrogen containing heterocyclic ring, wherein the heterocyclic ring is morpholinyl with no substitution, or pharmaceutically acceptable salts thereof. In a further embodiment, this invention relates to compounds of Formula (I), wherein $R^1$ and $R^2$, together with the nitrogen to which they are attached, form a nitrogen containing heterocyclic ring, wherein the heterocyclic ring is piperazine optionally substituted with one or two substituents each independently selected from $C_{1-3}$alkyl, or pharmaceutically acceptable salts thereof.

In a further embodiment, this invention relates to compounds of Formula (I), wherein $R^1$ and $R^2$, together with the nitrogen to which they are attached, form a nitrogen containing heterocyclic ring, wherein the heterocyclic ring is oxazolidine or pyrrolidine, optionally substituted with one or more substituents each independently selected from $C_{1-3}$alkyl, or pharmaceutically acceptable salts thereof.

In one embodiment, this invention relates to compounds of Formula (I), wherein $R^1$ and $R^2$, together with the nitrogen to which they are attached, form

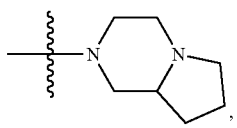

or pharmaceutically acceptable salts thereof.

In one embodiment, this invention relates to compounds of Formula (I), wherein $R^1$ and $R^2$, together with the nitrogen to which they are attached, form

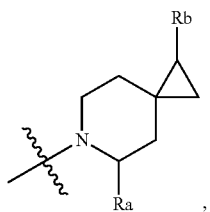

wherein each occurrence of $R^a$ and $R^b$ is independently selected from the group consisting of H, —CH$_2$OCH$_3$, C$_{1-3}$alkoxyl, and CH$_2$OH, or pharmaceutically acceptable salts thereof.

In another embodiment, this invention relates to compounds of Formula (I) and any of the above applicable embodiments, wherein $R^3$ and $R^6$ are each independently selected from H and C$_{1-3}$alkoxyl, or pharmaceutically acceptable salts thereof. In another embodiment, this invention relates to compounds of Formula (I) and any of the above applicable embodiments, wherein $R^3$ and $R^6$ are each independently selected from C$_{1-3}$alkoxyl, and pharmaceutically acceptable salts thereof. In one embodiment, this invention relates to compounds of Formula (I) and any of the above applicable embodiments, wherein $R^3$ and $R^6$ are each independently selected from H and OCH$_3$, or pharmaceutically acceptable salts thereof. In yet a further embodiment, this invention relates to compounds of Formula (I) and any of the above applicable embodiments, wherein $R^3$ and $R^6$ are H, or pharmaceutically acceptable salts thereof.

In another embodiment, this invention relates to compounds of Formula (I) and any of the above applicable embodiments, wherein $R^4$ and $R^5$ are each independently selected from H and halo, or pharmaceutically acceptable salts thereof. In one embodiment, this invention relates to compounds of Formula (I) and any of the above applicable embodiments, wherein $R^4$ and $R^5$ are each independently selected from H and F, or pharmaceutically acceptable salts thereof. In yet a further embodiment, this invention relates to compounds of Formula (I) and any of the above applicable embodiments, wherein $R^4$ and $R^5$ are H, or pharmaceutically acceptable salts thereof.

In another embodiment, this invention relates to compounds of Formula (I) and any of the above applicable embodiments, wherein $R^7$ is CH, or pharmaceutically acceptable salts thereof.

In another embodiment, this invention relates to compounds of Formula (I) and any of the above applicable embodiments, wherein $R^8$ is selected from the group consisting of H, CH$_3$, CF$_3$ and ON, or pharmaceutically acceptable salts thereof. In one embodiment, this invention relates to compounds of Formula (I) and any of the above applicable embodiments, wherein $R^8$ is selected from the group consisting of H, CH$_3$, and ON, or pharmaceutically acceptable salts thereof. In yet a further embodiment, this invention relates to compounds of Formula (I) and any of the above applicable embodiments, wherein $R^8$ is selected from H and ON, or pharmaceutically acceptable salts thereof. In a further embodiment, this invention relates to compounds of Formula (I) and any of the above applicable embodiments, wherein $R^8$ is H or pharmaceutically acceptable salts thereof.

In another embodiment, this invention relates to compounds of Formula (I) and any of the above applicable embodiments, wherein $R^9$ is selected from the group consisting of C$_{1-3}$alkoxyl, and —O—CH$_2$—C$_{3-6}$cycloalkyl, or pharmaceutically acceptable salts thereof. In one embodiment, this invention relates to compounds of Formula (I) and any of the above applicable embodiments, wherein $R^9$ is C$_{1-3}$alkoxyl, or pharmaceutically acceptable salts thereof. In yet a further embodiment, this invention relates to compounds of Formula (I) and any of the above applicable embodiments, wherein $R^9$ is —OCH$_2$CH$_3$, or pharmaceutically acceptable salts thereof. In one embodiment, this invention relates to compounds of Formula (I) and any of the above applicable embodiments, wherein $R^9$ is —O—CH$_2$-cyclopropyl, or pharmaceutically acceptable salts thereof.

In one embodiment, the compound of Formula (I) is a compound of any one of Examples E1 to E66, a free base, a free acid, or a salt (e.g., a pharmaceutically acceptable salt) thereof.

In addition to the free base form or free acid form of the compounds described herein, the salt form of the compounds is also within the scope of the present invention. The salts or pharmaceutically-acceptable salts of the compounds described herein may be prepared in situ during the final isolation and purification of the compound, or by separately reacting the purified compound in its free acid form or free base form with a suitable base or acid, respectively. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

In certain embodiments, compounds of the present invention may contain an acidic functional group, which is acidic enough to form salts. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, diethylamine, triethylamine, ethylenediamine, ethanolamine, diethanolamine, and cyclohexylamine.

In certain embodiments, compounds of the present invention may contain a basic group and are therefore capable of forming pharmaceutically-acceptable acid addition salts by treatment with a suitable acid. Suitable acids include pharmaceutically-acceptable inorganic acids and pharmaceutically-acceptable organic acids. These salts may be crystalline or amorphous. Exemplary pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methyl benzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In some embodiments, the pharmaceutically acceptable salts include the L-tartrate, ethanedisulfonate (edisylate), sulfate, phosphate, p-toluenesulfonate (tosylate), hydrochloride salt, methanesulfonate, citrate, fumarate, benzenesulfonate, maleate, hydrobromate, L-lactate, malonate, and S-camphor-10-sulfonate. In certain embodiments, some of these salts form solvates. In certain embodiments, some of these salts are crystalline.

The compounds of Formula (I), salts (e.g., pharmaceutically acceptable salts) thereof may exist in stereoisomeric forms (e.g., it contains one or more asymmetric carbon atoms). The individual stereoisomers (enantiomers and diastereomers) and mixtures of these are included within the scope of the present invention. The invention also covers the individual isomers of the compounds of Formula (I), salts (e.g., pharmaceutically acceptable salts) thereof as mixtures with isomers thereof in which one or more chiral centers are inverted. Likewise, it is understood that the compounds of Formula (I), salts (e.g., pharmaceutically acceptable salts) thereof may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. Also included within the scope of the invention are individual isomers of the compounds of Formula (I), salts (e.g., pharmaceutically acceptable salts) thereof, as well as any wholly or partially equilibrated mixtures thereof. The present invention also includes the individual isomers of the compounds of Formula (I), salts (e.g., pharmaceutically acceptable salts) thereof as well as mixtures with isomers thereof in which one or more chiral centers are inverted. It is to be understood that the present invention includes all combinations and subsets of the particular groups defined hereinabove. The different isomeric forms may be separated or resolved one from the other by conventional methods, or any given isomer may be obtained by conventional synthetic methods or by stereospecific or asymmetric syntheses.

The invention also includes isotopically-labelled compounds and salts, which are identical to compounds of Formula (I) or salts thereof, but for the fact that one or more atoms are replaced by an atom having an atomic mass or mass number different from the atomic mass or mass number most commonly found in nature. Examples of isotopes that can be incorporated into compounds of Formula (I) or salts thereof isotopes of hydrogen, carbon, nitrogen, fluorine, such as $^3$H, $^{11}$C, $^{14}$C and $^{18}$F. Such isotopically-labelled compound of Formula (I) or salts thereof are useful in drug and/or substrate tissue distribution assays. For example, $^{11}$C and $^{18}$F isotopes are useful in PET (positron emission tomography). PET is useful in brain imaging. Isotopically-labelled compounds of Formula (I) and salts thereof can generally be prepared by carrying out the procedures disclosed below, by substituting a readily available isotopically-labelled reagent for a non-isotopically labelled reagent. In one embodiment, compounds of Formula (I) or salts thereof are not isotopically labelled.

Certain compounds of Formula (I) or salts thereof may exist in solid or liquid form. In the solid state, compounds of Formula (I) or salts may exist in crystalline or noncrystalline form, or as a mixture thereof. For compounds of Formula (I) or salts that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of Formula (I), pharmaceutically acceptable salts or solvates thereof that exist in crystalline form, including the various solvates thereof, may exhibit polymorphism (i.e. the capacity to occur in different crystalline structures). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. The invention includes all such polymorphs.

The skilled artisan also appreciates that this invention may contain various deuterated forms of compounds of Formula (I), or pharmaceutically acceptable salts thereof. Each available hydrogen atom attached to a carbon atom may be independently replaced with a deuterium atom. A person of ordinary skill in the art will know how to synthesize deuterated forms of compounds of Formula (I), or pharmaceutically acceptable salts thereof. Commercially available deuterated starting materials may be employed in the preparation of deuterated forms of compounds of Formula (I) or pharmaceutically acceptable salts thereof, or they may be synthesized using conventional techniques employing deuterated reagents (e.g. lithium aluminum deuteride).

The compounds described herein, their salts (e.g., pharmaceutically acceptable salts), deuterated form, solvates or hydrates thereof, may exist in one or more polymorphic form. Therefore, in a further aspect, the invention provides a polymorph of a compound defined herein, their salts (e.g., pharmaceutically acceptable salts), or a polymorph of a solvate or hydrate of a compound described herein or a salt (e.g., pharmaceutically acceptable salt) thereof.

Accordingly, a compound of the invention includes a compound of Formula (I), or a salt thereof, for example a pharmaceutically acceptable salt thereof. Representative compounds of this invention include the specific compounds described.

C. Methods of Use

The compounds of Formula (I) or pharmaceutically acceptable salts thereof are inhibitors of LRRK2 kinase activity and are thus believed to be of potential use in the treatment of or prevention of neurological diseases. Exemplary neurological diseases include, but are not limited to, Parkinson's disease, Alzheimer's disease, dementia (including Lewy body dementia and vascular dementia, HIV-induced dementia), amyotrophic lateral sclerosis (ALS), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), withdrawal symptoms/relapse associated with drug addiction, L-Dopa induced dyskinesia, ischemic stroke, traumatic brain injury, spinal cord injury. Other disorders include, but are not limited to, lysosomal disorders (for example, Niemann-Pick Type C disease, Gaucher disease), Crohn's disease, thyroid, renal (including papillary renal), breast, lung and prostate cancers, leukemias (including acute myelogenous leukemia (AML)), lymphomas, leukemias, multiple sclerosis, rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies.

One aspect of the invention provides a compound of Formula (I) or a pharmaceutically acceptable salt thereof for use in therapy. In one embodiment, the invention provides a compound of Formula (I) or a pharmaceutically acceptable salt thereof for use in the treatment of or prevention of Parkinson's disease. In one embodiment, the invention provides a compound of Formula (I) or a pharmaceutically acceptable salt thereof for use in the treatment of Parkinson's disease.

A further aspect of the invention provides the use of a compound of Formula (I) or a pharmaceutically acceptable salt thereof in the manufacture of a medicament for the treatment of or prevention of Parkinson's disease. A further aspect of the invention provides the use of a compound of Formula (I) or a pharmaceutically acceptable salt thereof in the manufacture of a medicament for the treatment of Parkinson's disease.

A further aspect of the invention provides a method of treatment or prevention of Parkinson's disease, which comprises administering to a subject in need thereof a therapeutically effective amount of a compound of Formula (I) or a pharmaceutically acceptable salt thereof. In an embodiment, the subject is human.

In the context of the present invention, treatment of Parkinson's disease refers to the treatment of sporadic Parkinson's disease, and/or familial Parkinson's disease. In one embodiment, familial Parkinson's disease includes patients expressing LRRK2 kinase bearing the G2019S mutation or the R1441G mutation. In a further embodiment, familial Parkinson's disease includes patients expressing LRRK2 kinase bearing G2019S mutation, N1437H mutation, R1441G mutation, R14410 mutation, R1441H mutation, Y16990 mutation, S1761R mutation, or I2020T mutation for Parkinson's disease. In another embodiment, sporadic Parkinson's disease includes patients expressing LRRK2 kinase bearing G2019S mutation, N1437H mutation, R1441G mutation, R14410 mutation, R1441H mutation, Y16990 mutation, S1761R mutation, or I2020T mutation for Parkinson's disease. In another embodiment, Parkinson's disease includes patients expressing LRRK2 kinase bearing other coding mutations such as G2385R or non-coding single nucleotide polymorphisms at the LRRK2 locus that are associated with Parkinson's disease. In one embodiment, treatment of Parkinson's disease refers to the treatment of familial Parkinson's disease includes patients expressing LRRK2 kinase bearing G2019S mutation. In another embodiment, Parkinson's disease includes patients expressing aberrantly high levels of normal LRRK2 kinase. Treatment of Parkinson's disease may be symptomatic or may be disease modifying. In one embodiment, treatment of Parkinson's disease refers to symptomatic treatment. In one embodiment, treatment of Parkinson's disease refers to disease modifying.

Compounds of the present invention may also be useful in treating patients identified as susceptible to progression to severe Parkinsonism by means of one or more subtle features associated with disease progression such as family history, olfaction deficits, constipation, cognitive defects, gait or biological indicators of disease progression gained from molecular, biochemical, immunological or imaging technologies. In this context, treatment may be symptomatic or disease modifying.

In the context of the present invention, treatment of Alzheimer's disease refers to the treatment of sporadic Alzheimer's disease and/or familial Alzheimer's disease. Treatment of Alzheimer's disease may be symptomatic or may be disease modifying. In one embodiment, treatment of Alzheimer's disease refers to symptomatic treatment. Similarly, treatment of dementia (including Lewy body dementia vascular dementia, and HIV-induced dementia), age related memory dysfunction, mild cognitive impairment argyrophilic grain disease, amyotrophic lateral sclerosis (ALS), Pick's disease, corticobasal degeneration, progressive supranuclear palsy, inherited frontotemporal dementia and parkinsonism linked to chromosome 17 (FTDP-17), ischemic stroke, traumatic brain injury, spinal cord injury, lysosomal disorders (for example, Niemann-Pick Type C disease, Gaucher disease) Crohn's disease, thyroid, renal (including papillary renal), breast, lung and prostate cancers, leukemias (including acute myelogenous leukemia (AML)), lymphomas, leukemias, multiple sclerosis, rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies may be symptomatic or disease modifying. In some embodiments, treatment of dementia (including Lewy body dementia, vascular dementia and HIV-induced dementia), age related memory dysfunction, mild cognitive impairment, argyrophilic grain disease, amyotrophic lateral sclerosis (ALS), Pick's disease, corticobasal degeneration, progressive supranuclear palsy, inherited frontotemporal dementia and parkinsonism linked to chromosome 17 (FTDP-17), ischemic stroke, traumatic brain injury, spinal cord injury, lysosomal disorders (for example, Niemann-Pick Type C disease, Gaucher disease), Crohn's disease, thyroid, renal (including papillary renal), breast, lung and prostate cancers, leukemias (including acute myelogenous leukemia (AML)), lymphomas, leukemias, multiple sclerosis, rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies refers to symptomatic treatment.

In one embodiment, the invention also provides methods of treatment of ankylosing spondylitis and/or leprosy infection, which comprises administering to a subject in need thereof a therapeutically effective amount of a compound of Formula (I) or a pharmaceutically acceptable salt thereof. In some embodiments, the subject is human.

In the context of the present invention, treatment of withdrawal symptoms/relapse associated with drug addiction and L-Dopa induced dyskinesia refers to symptomatic treatment. In a further aspect, the invention provides a compound of Formula (I) or a pharmaceutically acceptable salt thereof for use in the treatment of the above disorders, for example Parkinson's disease. In some embodiments, the invention provides a compound of Formula (I) or a pharmaceutically acceptable salt thereof for use in the prevention of Parkinson's disease, Alzheimer's disease, of dementia (including Lewy body dementia vascular dementia and HIV-induced dementia), age related memory dysfunction, mild cognitive impairment, argyrophilic grain disease, amyotrophic lateral sclerosis (ALS), Pick's disease, corticobasal degeneration, progressive supranuclear palsy, inherited frontotemporal dementia or parkinsonism linked to chromosome 17 (FTDP-17), lysosomal disorders (e.g., Niemann-Pick Type C disease, Gaucher disease) or renal, breast, lung, prostate cancers as well as acute myelogenous leukemia (AML). In one embodiment, the invention provides a compound of Formula (I) or a pharmaceutically acceptable salt thereof for use in the prevention of Parkinson's disease.

The invention further provides a method of treatment of the above disorders, for example Parkinson's disease in mammals including humans, which comprises administering to a subject in need thereof a therapeutically effective amount of a compound of Formula (I) or a pharmaceutically acceptable salt thereof.

The invention also provides the use of a compound of Formula (I) or a pharmaceutically acceptable salt thereof in the manufacture of a medicament for use in the treatment of the above disorders, for example, Parkinson's disease. The invention also provides the use of a compound of Formula (I) or a pharmaceutically acceptable salt thereof in the manufacture of a medicament for use in the prevention of Parkinson's disease, Alzheimer's disease, of dementia (including Lewy body dementia and vascular dementia), age related memory dysfunction, mild cognitive impairment, argyrophilic grain disease, amyotrophic lateral sclerosis (ALS), Pick's disease, corticobasal degeneration, progressive supranuclear palsy, inherited frontotemporal dementia or parkinsonism linked to chromosome 17 (FTDP-17), or renal, breast, lung, prostate cancers as well as acute myelogenous leukemia (AML), lysosomal disorders (for example, Niemann-Pick Type C disease, Gaucher disease). In some embodiments, the invention provides the use of the compound of Formula (I) or a pharmaceutically acceptable salt thereof in the manufacture of a medicament for use in the prevention of Parkinson's disease.

The invention also provides the use of inhibitors of LRRK2 in the production of neuronal progenitor cells in vitro for consequent therapeutic application in cell based-treatment of CNS disorders.

The invention further provides the use of inhibitors of LRRK2 to stimulate restoration of CNS functions following neuronal injury including, but not limited to, ischemic stroke, traumatic brain injury, and spinal cord injury.

The invention also provides the use of inhibitors of LRRK2 to treat aberrant neuroinflammatory mechanisms that contribute a range of neurodegenerative diseases, including Parkinson's disease, Alzheimer's disease, muliltiple sclerosis, HIV-induced dementia, amyotrophic lateral sclerosis, ischemic stroke, traumatic brain injury and spinal cord injury.

When a compound of Formula (I) or a pharmaceutically acceptable salt thereof is intended for use in the treatment of Parkinson's disease, it may be used in combination with medicaments claimed to be useful as symptomatic treatments of Parkinson's disease. Suitable examples of such other therapeutic agents include L-dopa, and dopamine agonists (e.g. pramipexole, ropinirole).

When a compound of Formula (I) or a pharmaceutically acceptable salt thereof is intended for use in the treatment of Alzheimer's disease, it may be used in combination with medicaments claimed to be useful as either disease modifying or symptomatic treatments of Alzheimer's disease. Suitable examples of such other therapeutic agents may be symptomatic agents, for example those known to modify cholinergic transmission such as M1 muscarinic receptor agonists or allosteric modulators, M2 muscarinic antagonists, acetylcholinesterase inhibitors (such as tetrahydroaminoacridine, donepezil hydrochloride and rivastigmine), nicotinic receptor agonists or allosteric modulators (such as α7 agonists or allosteric modulators or α4β2 agonists or allosteric modulators), PPAR agonists (such as PPARγ agonists), 5-HT$_4$ receptor partial agonists, 5-HT$_6$ receptor antagonists or 5HT1A receptor antagonists and NMDA receptor antagonists or modulators, or disease modifying agents such as β or γ-secretase inhibitors, mitochondrial stabilizers, microtubule stabilizers or modulators of Tau pathology such as Tau aggregation inhibitors (e.g. methylene blue and REMBER™).

When a compound of Formula (I) or a pharmaceutically acceptable salt thereof is used in combination with other therapeutic agents, the compound may be administered either sequentially or simultaneously by any convenient route.

The invention also provides, in a further aspect, a combination comprising a compound of Formula (I) or a pharmaceutically acceptable salt thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of Formula (I) or a pharmaceutically acceptable salt thereof is used in combination with a second therapeutic agent active against the same disease state the dose of each compound may differ from that when the compound is used alone. Appropriate doses will be readily appreciated by those skilled in the art.

D. Composition

The compounds of the present invention may be formulated into pharmaceutical compositions prior to administration to a subject. According to one aspect, the invention provides a pharmaceutical composition comprising a compound of the invention and one or more pharmaceutically acceptable excipients. According to another aspect, the invention provides a process for the preparation of a pharmaceutical composition comprising admixing a compound of Formula (I), or salts thereof, or solvates etc thereof, with one or more pharmaceutically acceptable excipient.

Pharmaceutical compositions may be presented in unit dose forms containing a predetermined amount of active ingredient per unit dose. Such a unit may contain, for example, 0.1 mg, 0.5 mg, or 1 mg to 50 mg, 100 mg, 200 mg, 250 mg, 500 mg, 750 mg or 1 g of a compound of the present invention, depending on the disease being treated, the route of administration and the age, weight and condition of the subject, or pharmaceutical compositions may be presented in unit dose forms containing a predetermined amount of active ingredient per unit dose. In other embodiments, the unit dosage compositions are those containing a daily dose or sub-dose as described herein, or an appropriate fraction thereof, of an active ingredient. Furthermore, such pharmaceutical compositions may be prepared by any of the methods well-known to one skilled in the art.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, a therapeutically effective amount of a compound of present invention for the treatment of diseases described in the present invention will generally be in the range of 0.1 to 100 mg/kg body weight of recipient per day and more usually in the range of 1 to 10 mg/kg body weight per day. Thus, for a 70 kg adult mammal, the actual amount per day would usually be from 70 to 700 mg and this amount may be given in a single dose per day or in a number of sub-doses per day as such as two, three, four, five or six doses per day. Or the dosing can be done intermittently, such as once every other day, once a week or once a month. A therapeutically effective amount of a salt or solvate, etc., may be determined as a proportion of the therapeutically effective amount of the compound of Formula (I) per se. It is envisaged that similar dosages would be appropriate for treatment of the other diseases referred to above.

The pharmaceutical compositions of the invention may contain one or more compounds of the invention. In some embodiments, the pharmaceutical compositions may contain more than one compound of the invention. For example, in some embodiments, the pharmaceutical compositions may contain two or more compounds of the invention. In addition, the pharmaceutical compositions may optionally further comprise one or more additional pharmaceutically active compounds.

As used herein, "pharmaceutically acceptable excipient" means a pharmaceutically acceptable material, composition or vehicle involved in giving form or consistency to the pharmaceutical composition. Each excipient may be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided.

The compounds of the invention and the pharmaceutically-acceptable excipient or excipients may be formulated into a dosage form adapted for administration to the subject by the desired route of administration. For example, dosage forms include those adapted for (1) oral administration (including buccal or sublingual) such as tablets, capsules, caplets, pills, troches, powders, syrups, elixers, suspensions, solutions, emulsions, sachets, and cachets; (2) parenteral administration (including subcutaneous, intramuscular, intravenous or intradermal) such as sterile solutions, suspensions, and powders for reconstitution; (3) transdermal administration such as transdermal patches; (4) rectal administration such as suppositories; (5) nasal inhalation such as dry powders, aerosols, suspensions, and solutions; and (6) topical administration (including buccal, sublingual or transdermal) such as creams, ointments, lotions, solutions, pastes, sprays, foams, and gels. Such compositions may be prepared by any methods known in the art of pharmacy, for example by bringing into association a compound of Formula (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Suitable pharmaceutically-acceptable excipients may vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically acceptable excipients may be chosen for their ability to facilitate carrying or transporting the compound or compounds of the invention once administered to the subject from an organ, or a portion of the body, to another organ, or a portion of the body. Certain pharmaceutically-acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a therapeutically effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In certain embodiment, the present invention is directed to a pharmaceutical composition comprising 0.01 to 1000 mg of one or more compounds described herein or a pharmaceutically acceptable salt thereof and 0.01 to 5 g of one or more pharmaceutically acceptable excipients.

E. Process of Preparing Compounds

The process to be utilized in the preparation of the compounds described herein depends upon the desired compounds. Such factors as the selection of the specific substituent and various possible locations of the specific substituent all play a role in the path to be followed in the preparation of the specific compounds of this invention. Those factors are readily recognized by one of ordinary skill in the art.

In general, the compounds of the present invention may be prepared by standard techniques known in the art and by known processes analogous thereto. General methods for preparing compounds of the present invention are set forth below. All starting material and reagents described in the below general experimental schemes are commercially available or can be prepared by methods known to one skilled in the art. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

General Schemes 1-3 provide exemplary processes of synthesis for preparing compounds of the present invention.

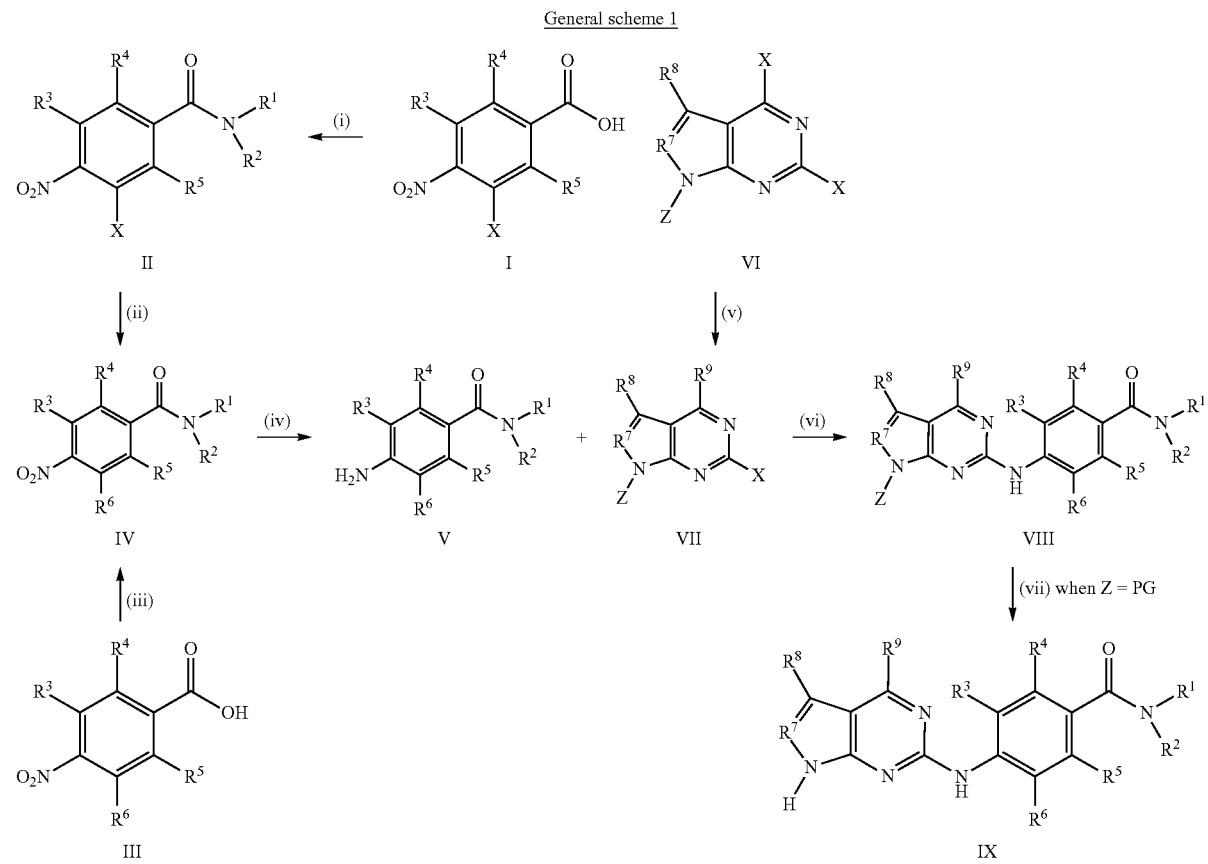

General Scheme 1 provides an exemplary synthesis for preparing compounds VIII and IX. The protecting group can be any suitable protecting group for example, 4-methylbenzene-1-sulfonyl (Ts). In General Scheme 1, $R^1$, $R^2$, $R^3$, $R^4$, $R^5$, $R^6$, $R^7$, and $R^9$ are as defined in Formula (I) and $R^8$ is selected from the group consisting of H, $C_{1-3}$haloalkyl (except $CF_3$) and $C_{1-3}$alkyl.

Intermediates II can be obtained by amino-coupling reaction from intermediates I with amines in step (i) in the presence of condensation reagents such as HATU and suitable bases such as DIPEA in appropriate solvents such as DMF under suitable temperatures such as room temperature. Intermediates IV can be obtained by reacting compound II with suitable reagents such as EtOH in step (ii) in the presence of suitable bases such as NaH in appropriate solvents such as DMF under suitable temperatures such as about 0° C. to 25° C. Intermediates IV can also be obtained by reacting intermediates III with amines in the presence of condensation reagents such as HATU and suitable bases such as DIPEA in appropriate solvents such as DMF under suitable temperatures such as about 0° C. to 25° C. in step (iii).

Amino compounds V can be obtained by reacting intermediates IV with suitable reducing reagents such as hydrogen in the presence of suitable catalysts such Pd/C in polar solvents such as MeOH at appropriate temperatures such as about 25° C. to 80° C. in step (iv).

Step (v) can be carried out by reacting intermediates VI with sodium alkoxy in the presence of suitable polar solvents such as EtOH under suitable temperatures such as about 70° C. to 90° C. to provide intermediates VII.

Step (vi) can be a Buchwald coupling reaction by reacting intermediates VII with intermediates V using appropriate palladium catalysts such as $Pd_2(dba)_3$ in the presence of suitable bases such as $K_2CO_3$ and suitable ligands such as xantphos in appropriate solvents such as 1,4-dioxane under suitable temperatures such as about 90° C. to 120° C. to provide compound VIII.

When Z=PG, compound IX could be obtained by reacting compound VIII with suitable bases such as NaOH in suitable solvents such as isopropanol at suitable temperatures such as 25° C. to 60° C. in step (viii).

General scheme 2

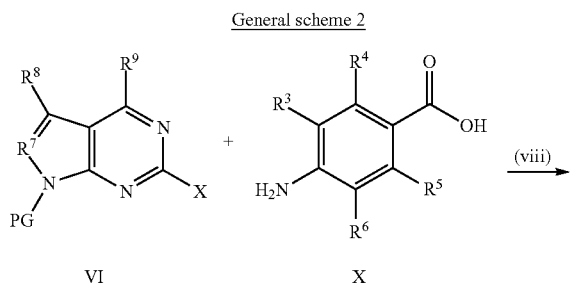

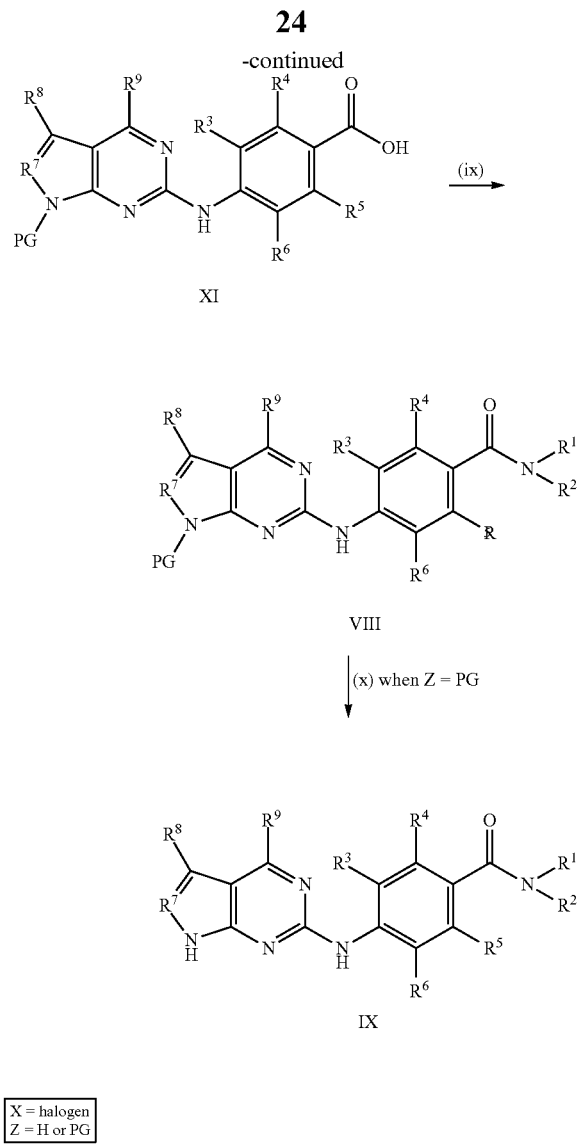

X = halogen
Z = H or PG

General Scheme 2 provides another exemplary synthesis for preparing compounds VIII and IX. The protecting group can be any suitable protecting group for example, 4-methylbenzene-1-sulfonyl (Ts). In General Scheme 2, $R^1$, $R^2$, $R^3$, $R^4$, $R^5$, $R^6$, $R^7$, and $R^9$ are as defined in Formula (I) and $R^8$ is selected from the group consisting of H, $C_{1-3}$haloalkyl (except $CF_3$) and $C_{1-3}$alkyl.

Intermediates XI can be obtained by Buchwald coupling reaction between intermediates VI with intermediates X in step (viii) using appropriate palladium catalysts such as $PdCl_2(dppf)$ in the presence of appropriate bases such as $K_2CO_3$ and appropriate ligands such as X-Phos in appropriate solvents such as 2-butanol under suitable temperatures such as about 90° C. to 120° C.

Intermediates VIII can be obtained in Step (ix) by reacting intermediates XI with amines in the presence of condensation reagents such as HATU and suitable bases such as DIPEA in appropriate solvents such as DMF under suitable temperatures such as about 0° C. to 25° C. When Z=PG, compound IX can be obtained by reacting compound VIII with suitable bases such as NaOH in suitable solvents such as isopropanol at suitable temperatures such as about 25° C. to 60° C. in step (viii).

General scheme 2

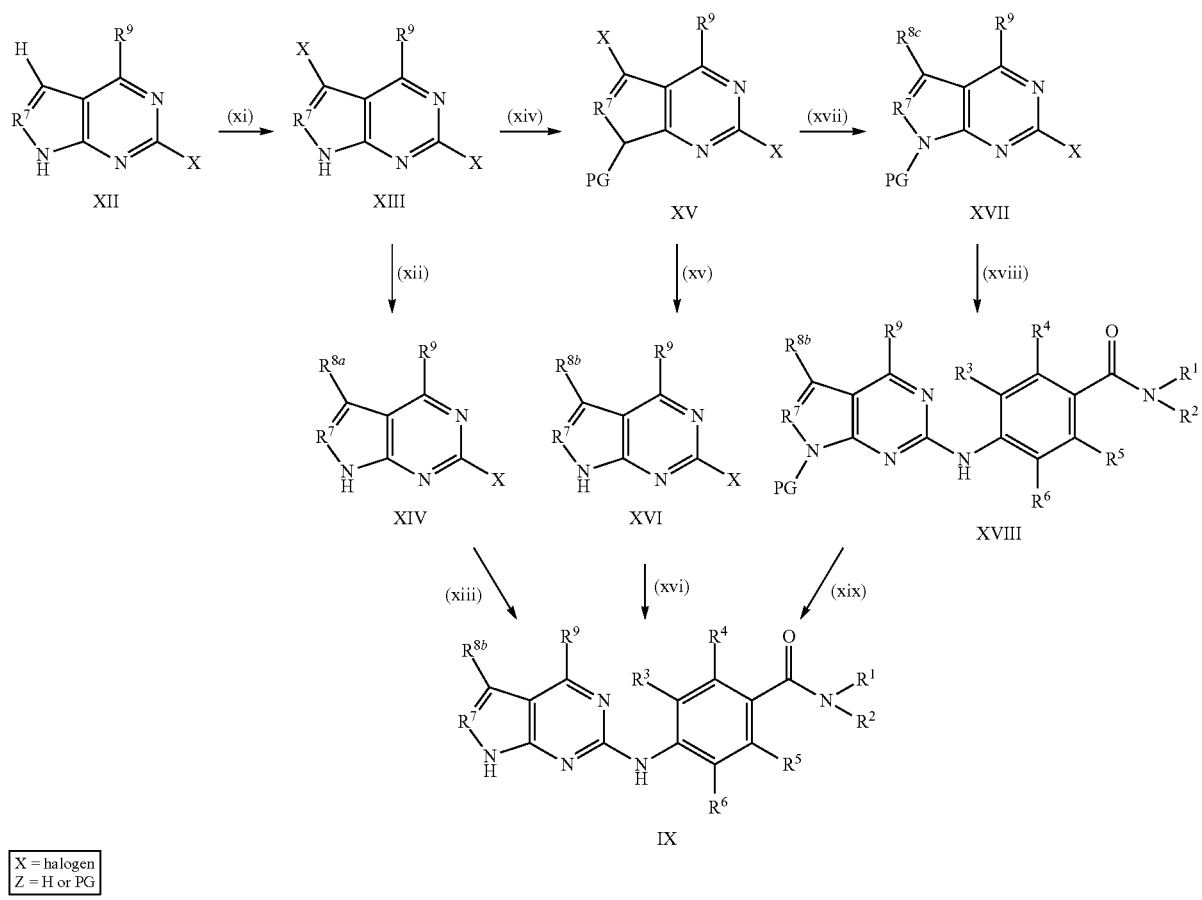

X = halogen
Z = H or PG

General Scheme 3 provides another exemplary synthesis for preparing compounds IX. The protecting group can be any suitable protecting group for example, 4-methylbenzene-1-sulfonyl (Ts). In General Scheme I, $R^1$, $R^2$, $R^3$, $R^4$, $R^5$, $R^6$, $R^7$, $R^8$ and $R^9$ are as defined in Formula (I).

Intermediates XIII can be obtained in Step (xi) by reacting intermediates XII with suitable reagents such as NIS in suitable solvents such as DMF at suitable temperatures such as about 25° C. to 60° C.

Step (xii) can be a cross-coupling reaction between intermediates XIII and suitable reagents such as copper (I) cyanide in suitable solvents under suitable temperatures such as about 90° C. to 130° C. to provide intermediates XIV, which can be reacted with intermediates V in step (xiii) using appropriate palladium catalysts such as $Pd_2(dba)_3$ in the presence of suitable bases such as $K_2CO_3$ and suitable ligands such as X-phos in appropriate solvents such as 2-butanol under suitable temperatures such as about 90° C. to 120° C. to provide compounds IX.

Intermediates XV can be obtained in step (xiv) by reacting intermediates XIII with suitable reagents such as TsCl in the presence of suitable bases such as NaH in appropriate solvents such as DMF under suitable temperatures such as about 0° C. to 25° C. Step (xv) can be a cross-coupling reaction by reacting intermediates XV with suitable reagents such as 2,2-difluoro-2-(fluorosulfonyl)-acetate in the presence of suitable copper catalysts such as CuI in appropriate solvents in suitable temperatures such as about 80° C. to 120° C. to provide intermediates XVI, which can be reacted with intermediates V in step (xvi) using appropriate palladium catalysts such as $Pd_2(dba)_3$ in the presence of suitable bases such as $K_2CO_3$ and suitable ligands such as X-Phos in appropriate solvents such as 2-butanol under suitable temperatures such as about 90° C. to 120° C. to provide compounds IX.

Step (xvii) can be a Suzuki coupling reaction by reacting intermediates XV with a suitable boronic acid or ester using appropriate palladium catalysts such as $Pd(PPh_3)_4$ in the presence of appropriate bases such as $Na_2CO_3$ in appropriate solvents such as 1,4-dioxane under suitable temperatures such as about 80° C. to 120° C. to provide intermediates XVII, which may be reacted with intermediates V in step (xviii) using appropriate palladium catalysts such as $Pd_2(dba)_3$ in the presence of appropriate bases such as $K_2CO_3$ and appropriate ligands in appropriate solvents under suitable temperatures such as about 90° C. to 120° C. to provide intermediates XVIII.

Compounds IX can be obtained by reacting intermediates XVIII with suitable bases such as NaOH in suitable solvents such as methanol at suitable temperatures such as about 25° C. to 60° C. in step (xix).

The starting material and reagents described in the above schemes are either commercially available or may be readily prepared from commercially available compounds using procedures known to a person of ordinary skill in the art.

EXAMPLES

General Experimental Procedures

The following descriptions and examples illustrate the invention. These examples are not intended to limit the scope of the present invention, but rather to provide guidance to the skilled chemist to prepare and use the compounds, compositions and methods of the present invention. While particular embodiments of the present invention are described, the skilled chemist will appreciate that various changes and modifications can be made without departing from the spirit and scope of the invention.

Heating of reaction mixtures with microwave irradiations was carried out on a Smith Creator (purchased from Personal Chemistry, Forboro/MA, now owned by Biotage), an Emrys Optimizer (purchased from Personal Chemistry) or an Explorer (provided by CEM Discover, Matthews/NC) microwave.

Conventional techniques may be used herein for work up of reactions and purification of the products of the Examples.

References in the Examples below relating to the drying of organic layers or phases may refer to drying the solution over magnesium sulfate or sodium sulfate and filtering off the drying agent in accordance with conventional techniques. Products may generally be obtained by removing the solvent by evaporation under reduced pressure.

Purification of the compounds in the examples may be carried out by conventional methods such as chromatography and/or re-crystallization using suitable solvents. Chromatographic methods are known to the skilled person and include e.g. column chromatography, flash chromatography, HPLC (high performance liquid chromatography), and MDAP (mass directed auto-preparation, also referred to as mass directed LCMS purification). MDAP is described in e.g. W. Goetzinger et al, *Int. J. Mass Spectrom.*, 2004, 238, 153-162.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. Preparative HPLC were performed using a Gilson Preparative System using a Luna 5 u C18(2) 100A reverse phase column eluting with a 10-80 gradient (0.1% TFA in acetonitrile/0.1% aqueous TFA) or a 10-80 gradient (acetonitrile/water). The CombiFlash system used for purification in this application was purchased from Isco, Inc. CombiFlash purification was carried out using a pre-packed $SiO_2$ column, a detector with UV wavelength at 254 nm and mixed solvents.

The terms "CombiFlash", "Biotage®", "Biotage 75" and "Biotage SP4®" when used herein refer to commercially available automated purification systems using pre-packed silica gel cartridges.

Final compounds were characterized with LCMS (conditions listed below) or NMR. $^1$H NMR spectra were recorded using a Bruker Avance 400 MHz spectrometer. $CDCl_3$ is deuteriochloroform, DMSO-$d_6$ is hexadeuteriodimethylsulfoxide, and $CD_3OD$ (or MeOD) is tetradeuteriomethanol. Chemical shifts are reported in parts per million (ppm) downfield from the internal standard tetramethylsilane (TMS) or the NMR solvent. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Mass spectra were taken on instruments, using electrospray (ES) ionization techniques. All temperatures are reported in degrees Celsius. All other abbreviations are as described in the ACS Style Guide (American Chemical Society, Washington, D C, 1986).

Absolute stereochemistry can be determined by methods known to one skilled in the art, for example X-ray or Vibrational circular dichroism (VCD).

In the procedures that follow, after each starting material, reference to an intermediate is typically provided. This is provided merely for assistance to the skilled chemist. The starting material may not necessarily have been prepared from the batch referred to.

LCMS Conditions:
Condition 1:
Mobile phase: water containing 0.05% TFA/0.05% acetonitrile
Column: Agilent SB-C18 4.6×30 mm-1.8 microns
Detection: MS and photodiode array detector (PDA)
Condition 2:
Mobile phase: water containing 10 mmol $NH_4HCO_3$/acetonitrile
Column: XBridge™ C18 4.6×50 mm-3.5 microns
Detection: MS and photodiode array detector (PDA)
MDAP Conditions:
1) Acidic conditions:
Instrument: Waters instrument
Column: Sunfire Prep C18 column (5 um, 19×50 mm)
Mobile phase: water containing 0.05% TFA/acetonitrile.
2) Basic conditions:
Instrument: Waters instrument
Column: Xbridge Prep C18 column (5 um, 19×50 mm)
Mobile phase: water containing 0.04% ammonia/acetonitrile.
Prep-HPLC Conditions
Instrument: Waters instrument
Column: Xbridge Prep C18 column OBD (10 um, 19×250 mm)
Mobile phase: water containing 0.08% ammonia/acetonitrile.

Abbreviations and Resource Sources

The following abbreviations and resources are used herein below:
Aq.—aqueous
$Boc_2O$—Di-tert-butyl dicarbonate
DCM—Dichloromethane;
DEA—Diethanolamine
DIPEA—N,N-Diisopropylethylamine
DMA—N,N-dimethylacetamide
DMF—Dimethylformamide;
DMSO—Dimethyl sulfoxide
EA—Ethyl acetate;
EDC—1-ethyl-3-(3-dimethylaminopropyl)carbodiimide hydrochloride
EtOH—ethanol
EtOAc—Ethyl acetate
HATU—2-(1H-7-Azabenzotriazol-1-yl)-1,1,3,3-tetramethyl uranium hexafluorophosphate
HOBT—Hydroxybenzotriazole
NIS—N-Iodosuccinimide
TEA—Triethylamine
TFA—Trifluoroacetic acid
TFAA—Trifluoroacetic anhydride
THF—Tetrahydrofuran;
TsCl—4-Toluenesulfonyl chloride
PE—Petroleum ether;

Description D1

2-chloro-4-ethoxy-7H-pyrrolo-[2,3-d]pyrimidine
(D1)

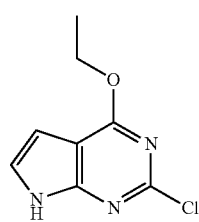

A mixture of 2,4-dichloro-7H-pyrrolo-[2,3-d]pyrimidine (13 g, 69.1 mmol), sodium ethoxide (5.65 g, 83 mmol) and ethanol (100 mL) was heated overnight at 90° C. The mixture was cooled to room temperature and water (500 mL) was then added. The solid formed was filtered and dried to give the title compound D1 (10.0 g, 50.6 mmol, 73.2% yield) as a white solid.

LCMS: 198 [M+1]$^+$. $t_R$=1.348. (LCMS condition 2)

$^1$H NMR (400 MHz, DMSO-d$_6$): δ 12.23 (br. s., 1H), 7.38 (d, J=3.4 Hz, 1H), 6.50 (d, J=3.4 Hz, 1H), 4.51 (q, J=7.1 Hz, 2H), 1.39 (t, J=7.0 Hz, 3H).

Description D2

2-chloro-4-ethoxy-7-tosyl-7H-pyrrolo-[2,3-d]-pyrimidine (D2)

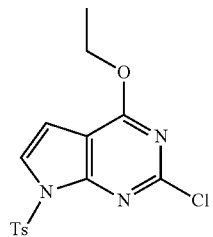 [SMILES: CCOc1nc(Cl)nc2c1ccn2S(=O)(=O)c1ccc(C)cc1]

To a solution of 2-chloro-4-ethoxy-7H-pyrrolo-[2,3-d]-pyrimidine (which may be prepared according to D1) (8 g, 40.5 mmol) in DMF (50 mL) was added sodium hydride (1.619 g, 40.5 mmol). The reaction mixture was stirred for 5 min at room temperature. Then to this mixture was added 4-methylbenzene-1-sulfonyl chloride (7.72 g, 40.5 mmol) and the reaction was left under stirring for further 1 hour at room temperature. The mixture was diluted with water (450 mL) and filtered. The filtered solid was washed with water (90 mL) and dried to give the title compound D2 (10 g, 26.2 mmol, 64.6% yield) as a white solid.

LCMS: 352 [M+H]$^+$. $t_R$=1.871. (LCMS condition 2)

General Procedure 1 for Amino-Coupling Reaction for D3-D21

A mixture of acids (1.0 eq), amine (1.0 eq), DIPEA (1.2 eq), and HATU (1.2 eq) in DMF (2 mL) was stirred overnight at room temperature. The reaction mixture was cooled to room temperature and volatile was removed under vacuum. The residue was evaporated twice with DCM, triturated with ether and eventually purified by chromatography on silica gel (PE:EA=1:2) to give the desired products D3-D21.

| | Structure/name | Acid (starting material) | Amine (Starting material) | [M + H]$^+$ | Yield |
|---|---|---|---|---|---|
| D3 | 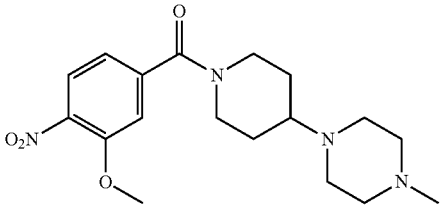<br>(3-methoxy-4-nitrophenyl)(4-(4-methylpiperazin-1-yl)piperidin-1-yl)methanone | 3-methoxy-4-nitro-benzoic acid | 1-methyl-4-(piperidin-4-yl)piperazine | 333 | 98% |
| D4 | 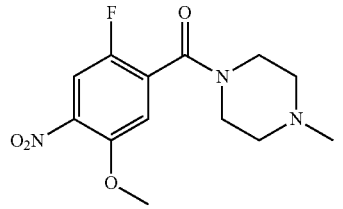<br>(2-fluoro-5-methoxy-4-nitrophenyl)(4-methylpiperazin-1-yl)methanone | 2-fluoro-5-methoxy-4-nitrobenzoic-acid | 1-methyl-piperazine | 298 | 73% |

-continued

| | Structure/name | Acid (starting material) | Amine (Starting material) | [M + H]+ | Yield |
|---|---|---|---|---|---|
| D5 | 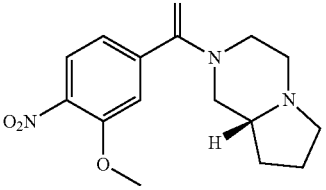<br>(S)-(hexahydropyrrolo[1,2-a]pyrazin-2(1H)-yl)(3-methoxy-4-nitrophenyl)methanone | 3-methoxy-4-nitrobenzoic acid | (S)-octahydropyrrolo-[1,2-a]pyrazine | 306 | 81% |
| D6 | 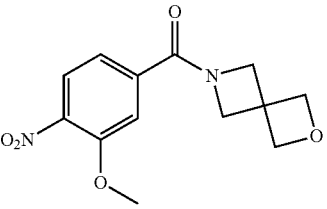<br>(3-methoxy-4-nitrophenyl)(2-oxa-6-azaspiro[3.3]heptan-6-yl)methanone | 3-methoxy-4-nitrobenzoic acid | 2-oxa-6-azaspiro[3.3]heptane | 279 | 65% |
| D7 | 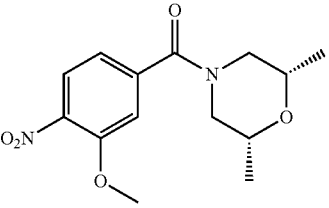<br>((2R,6S)-2,6-dimethylmorpholino)(3-methoxy-4-nitrophenyl)methanone | 3-methoxy-4-nitrobenzoic acid | (2R,6S)-2,6-dimethylmorpholine | 295 | 76% |
| D8 | 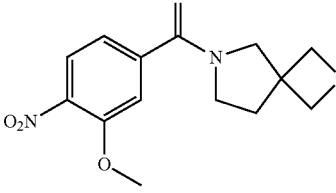<br>(3-methoxy-4-nitrophenyl)(2-oxa-6-azaspiro[3.4]octan-6-yl)methanone | 3-methoxy-4-nitrobenzoic acid and | 2-oxa-6-azaspiro[3.4]octane | 293 | 65% |
| D9 | 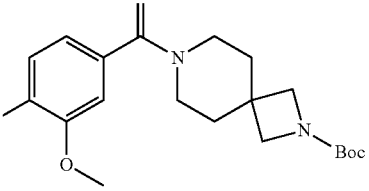<br>tert-butyl 7-(3-methoxy-4-nitrobenzoyl)-2,7-diazaspiro[3.5]nonane-2-carboxylate | 3-methoxy-4-nitrobenzoic acid | tert-butyl 2,7-diazaspiro[3.5]nonane-2-carboxylate | 406 | 86% |

| | Structure/name | Acid (starting material) | Amine (Starting material) | [M + H]+ | Yield |
|---|---|---|---|---|---|
| D10 | 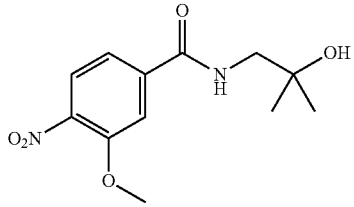<br>N-(2-hydroxy-2-methylpropyl)-3-methoxy-4-nitrobenzamide | 3-methoxy-4-nitrobenzoic acid | 1-amino-2-methylpropan-2-ol | 269 | 65% |
| D11 | 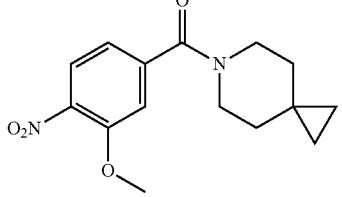<br>(3-methoxy-4-nitrophenyl)(6-azaspiro[2.5]octan-6-yl)methanone | 3-methoxy-4-nitrobenzoic acid | 6-azaspiro[2.5]-octane | 291 | 24% |
| D12 | 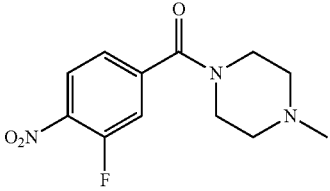<br>(3-fluoro-4-nitrophenyl)(4-methylpiperazin-1-yl)methanone | 3-fluoro-4-nitrobenzoic acid | 1-methylpiperazine | 268 | 59% |
| D13 | 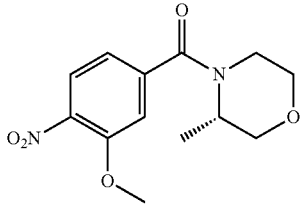<br>(S)-(3-methoxy-4-nitrophenyl)(3-methylmorpholino)methanone | 3-methoxy-4-nitrobenzoic acid and | (S)-3-methylmorpholine | 281 | 54% |
| D14 | 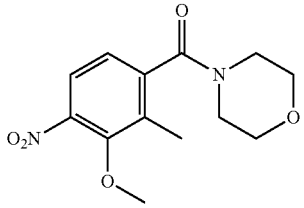<br>(3-methoxy-2-methyl-4-nitrophenyl)(morpholino)methanone | 3-methoxy-2-methyl-4-nitrobenzoic acid | morpholine | 281 | 67% |

-continued

| | Structure/name | Acid (starting material) | Amine (Starting material) | [M + H]+ | Yield |
|---|---|---|---|---|---|
| D15 | 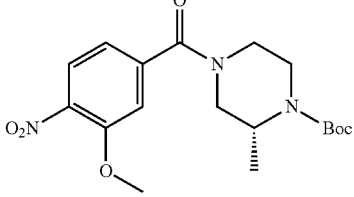<br>(R)-tert-butyl 4-(3-methoxy-4-nitrobenzoyl)-2-methylpiperazine-1-carboxylate | 3-methoxy-4-nitrobenzoic acid | (R)-tert-butyl 2-methylpiperazine-1-carboxylate | 382 | 68% |
| D16 | 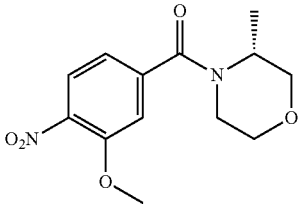<br>(R)-(3-methoxy-4-nitrophenyl)(3-methylmorpholino)methanone | 3-methoxy-4-nitrobenzoic acid | (R)-3-methylmorpholine | 281 | 84% |
| D17 | 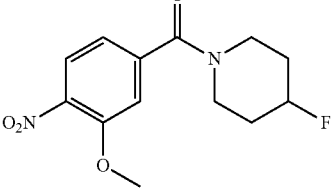<br>(4-fluoropiperidin-1-yl)(3-methoxy-4-nitrophenyl)methanone | 3-methoxy-4-nitrobenzoic acid | 4-fluoropiperidine | 283 | 82% |
| D18 | 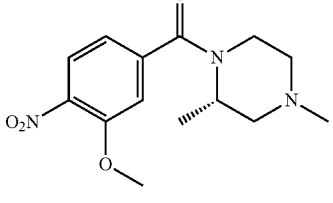<br>(S)-(2,4-dimethylpiperazin-1-yl)(3-methoxy-4-nitrophenyl)methanone | 3-methoxy-4-nitrobenzoic acid | (S)-1,3-dimethylpiperazine | 294 | 51% |
| D19 | 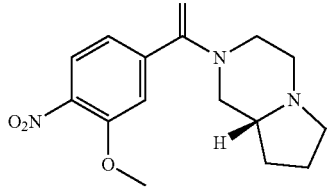<br>(R)-(hexahydropyrrolo[1,2-a]pyrazin-2(1H)-yl)(3-methoxy-4-nitrophenyl)methanone | 3-methoxy-4-nitrobenzoic acid | (R)-octahydro-pyrrolo-[1,2-a]pyrazine | 306 | 48% |

-continued

| Structure/name | Acid (starting material) | Amine (Starting material) | [M + H]+ | Yield |
|---|---|---|---|---|
| D20 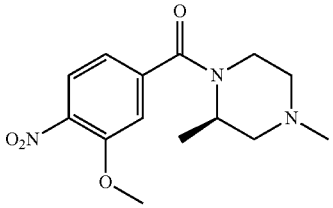<br>(R)-(2,4-dimethylpiperazin-1-yl)(3-methoxy-4-nitrophenyl)methanone | 3-methoxy-4-nitrobenzoic acid | (R)-1,3-dimethylpiperazine | 294 | 45% |
| D21 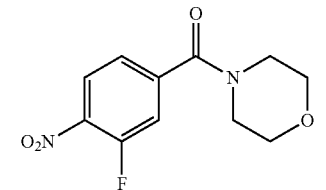<br>(3-fluoro-4-nitrophenyl)(morpholino)methanone | 3-fluoro-4-nitrobenzoic acid | morpholine | 252 | 82% |

Description D22 methyl 3-(difluoromethoxy)-4-nitrobenzoate (D22)

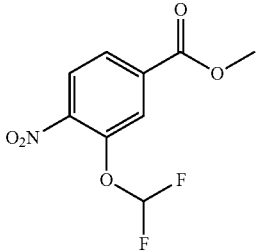 [SMILES: COC(=O)c1ccc([N+](=O)[O-])c(OC(F)F)c1]

To a solution of methyl 3-hydroxy-4-nitrobenzoate (1 g, 5.07 mmol) in DMF (15 mL) was successively added $K_2CO_3$ (1.052 g, 7.61 mmol) and methyl 2-chloro-2,2-difluoroacetate (0.803 mL, 7.61 mmol) at room temperature. Subsequently, the temperature of the mixture was raised to 100° C., and the mixture was stirred for 2 hours. The mixture was cooled to room temperature, and water (10 mL) was added, followed by extraction with EA (40 mL) once. The organic layer was washed with water (20 mL), brine (20 mL), dried over $Na_2SO_4$ and concentrated. The crude was purified by chromatography on silica gel (PE:EA=1:1) to give the title compound D22 (0.69 g, 2.62 mmol, 51.7% yield) as yellow oil.

LCMS: 248[M+H]+. $t_R$=3.154. (LCMS condition 1)

$^1$H NMR (400 MHz, METHANOL-$d_4$): δ 6.75-6.77 (m, 2H), 6.73 (s, 1H), 5.77 (t, 1H), 2.66-2.71 (m, 3H).

Description D23
3-(difluoromethoxy)-4-nitrobenzoic acid (D23)

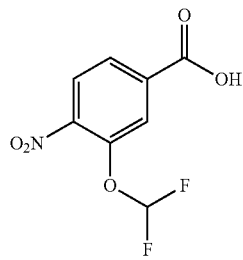 [SMILES: O=C(O)c1ccc([N+](=O)[O-])c(OC(F)F)c1]

To a solution of methyl 3-(difluoromethoxy)-4-nitrobenzoate (which may be prepared according to D22) (690 mg, 2.79 mmol) in methanol (30 mL) and water (30.0 mL) was added sodium hydroxide (893 mg, 22.33 mmol). The mixture was then stirred at 60° C. for 2 hours. Methanol was evaporated, and 2N HCl solution was added to the mixture until pH=3. The solid formed was filtrated and dried to give the title compound D23 (428 mg, 1.836 mmol, 65.8% yield) as a yellow solid.

LCMS: 234[M+H]+. $t_R$=2.302. (LCMS condition 1)

$^1$H NMR (400 MHz, DMSO-$d_6$): δ 13.93 (br. s., 1H), 8.19 (d, J=8.6 Hz, 1H), 7.92-8.02 (m, 2H), 7.30-7.70 (m, 1H).

Description D24
(3-(difluoromethoxy)-4-nitrophenyl)-(4-methylpiperazin-1-yl)methanone (D24)

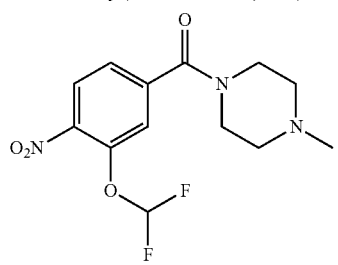

A mixture of 3-(difluoromethoxy)-4-nitrobenzoic acid (which may be prepared according to D23) (318 mg, 1.364 mmol), DIPEA (0.357 mL, 2.046 mmol) and HATU (622 mg, 1.637 mmol) in DMF (10 mL) was stirred at room temperature for 30 min. 1-Methylpiperazine (0.206 mL, 2.046 mmol) was then added. The mixture was stirred overnight at room temperature. The reaction mixture was diluted with ethyl acetate and water, and separated. The organic layer was concentrated in vacuum, and the crude was purified by chromatography on silica gel (PE:EA=1:1) to give the title compound D24 (150 mg, 0.476 mmol, 34.9% yield) as yellow oil.

LCMS: 316[M+H]$^+$. $t_R$=1.845. (LCMS condition 1)

$^1$H NMR (400 MHz, CHLOROFORM-d): δ 7.90 (d, J=8.3 Hz, 1H), 7.28-7.40 (m, 2H), 6.34-6.80 (m, 1H), 3.74 (br. s., 2H), 3.33 (br. s., 2H), 2.44 (br. s., 2H), 2.30 (br. s., 2H), 2.27 (s, 3H).

Description D25 methyl 3-(cyclopropylmethoxy)-4-nitrobenzoate (D25)

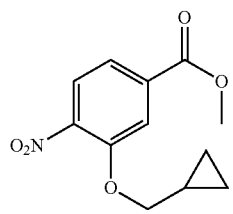 [SMILES: COC(=O)c1ccc([N+](=O)[O-])c(OCC2CC2)c1]

To a solution of methyl 3-hydroxy-4-nitrobenzoate (1 g, 5.07 mmol) in DMF (15 mL) was added sodium hydride (0.304 g, 7.61 mmol) at 0° C. After stirred at room temperature for 30 min, (bromomethyl)cyclopropane (0.738 mL, 7.61 mmol) was then added. The mixture was stirred overnight at room temperature. The mixture was diluted with EA, washed with water. The organic layer was dried and concentrated. The crude was purified by chromatography on silica gel (PE:EA=1:1) to give the title compound D25 (360 mg, 1.333 mmol, 26.3% yield) as a yellow solid.

LCMS: 250[M−H]$^-$. $t_R$=4.191. (LCMS condition 1)

$^1$H NMR (400 MHz, METHANOL-d$_4$): δ 7.79-7.87 (m, 2H), 7.69 (dd, J=1.5, 8.3 Hz, 1H), 4.08 (d, J=6.8 Hz, 2H), 3.95 (s, 3H), 1.27-1.32 (m, 1H), 0.61-0.71 (m, 2H), 0.36-0.45 (m, 2H).

Description D26

3-(cyclopropylmethoxy)-4-nitrobenzoic acid (D26)

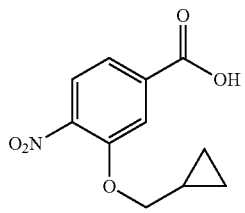 [SMILES: O=C(O)c1ccc([N+](=O)[O-])c(OCC2CC2)c1]

To a solution of methyl 3-(cyclopropyl-methoxy)-4-nitrobenzoate (which may be prepared according to D25) (360 mg, 1.433 mmol) in methanol (30 mL) and water (30.0 mL) was added NaOH (459 mg, 11.46 mmol). The mixture was then stirred at 60° C. for 1.5 hours. Methanol was evaporated, and then 2N HCl solution was added to the mixture until pH=3. The solid formed was filtrated and dried to give the title compound D26 (250 mg, 1.054 mmol, 73.6% yield) as a yellow solid.

LCMS: 238[M+H]$^+$. $t_R$=2.940. (LCMS condition 1)

$^1$H NMR (400 MHz, METHANOL-d$_4$): δ 7.80-7.86 (m, 2H), 7.72 (d, J=1.2 Hz, 1H), 4.09 (d, J=6.8 Hz, 2H), 1.32-1.37 (m, 1H), 0.63-0.70 (m, 2H), 0.43 (q, J=4.9 Hz, 2H).

Description D27

(3-(cyclopropylmethoxy)-4-nitrophenyl)(4-methyl-piperazin-1-yl)-methanone (D27)

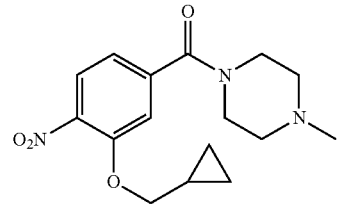 [SMILES: CN1CCN(C(=O)c2ccc([N+](=O)[O-])c(OCC3CC3)c2)CC1]

A mixture of 3-(cyclopropylmethoxy)-4-nitrobenzoic acid (which may be prepared according to D26) (252 mg, 1.062 mmol), DIPEA (0.278 mL, 1.594 mmol) and HATU (485 mg, 1.275 mmol) in DMF (10 mL) was stirred at room temperature for 30 min. 1-Methylpiperazine (0.267 mL, 2.66 mmol) was then added. The mixture was stirred overnight at room temperature. The reaction mixture was diluted with ethyl acetate and washed with water. The organic layer was concentrated in vacuum, and the crude was purified by chromatography on silica gel (PE:EA=1:1) to give the title compound D27 (480 mg, 0.812 mmol, 76% yield) as yellow oil.

LCMS: 320.1[M+H]$^+$. $t_R$=2.068. (LCMS condition 1)

$^1$H NMR (400 MHz, CHLOROFORM-d): δ 7.76 (d, J=8.1 Hz, 1H), 7.03 (s, 1H), 6.84-6.96 (m, 1H), 3.93 (d, J=6.8 Hz, 2H), 3.74 (br. s., 2H), 3.34 (br. s., 2H), 2.46 (br. s., 2H), 2.29-2.35 (m, 2H), 2.29 (s, 3H), 1.60-1.62 (m, 1H), 1.34-1.45 (m, 2H), 1.14-1.30 (m, 2H).

Description D28

(3-methoxy-4-nitrophenyl)(oxazolidin-3-yl)-methanone (D28)

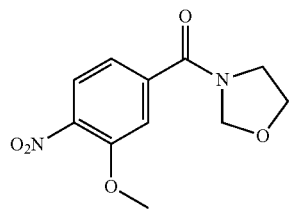 [SMILES: COc1cc(C(=O)N2CCOC2)ccc1[N+](=O)[O-]]

A solution of 2-aminoethanol (0.310 g, 5.07 mmol) and formaldehyde (0.210 mL, 7.61 mmol) in EtOH (5 mL) was heated at 60° C. for 2 hours. The mixture was concentrated and the residue was added to a mixture of DIPEA (1.311 g, 10.14 mmol), HATU (3.86 g, 10.14 mmol) and 3-methoxy-4-nitrobenzoic acid (1.0 g, 5.07 mmol) in DMF (10 mL). The reaction was then stirred overnight at room temperature. The mixture was concentrated and directly purified by pre-HPLC to give the title compound D28 (700 mg, 0.916 mmol, 18.06% yield) as yellow oil.

LCMS: 253[M+H]$^+$. $t_R$=1.057. (LCMS condition 2)

Description D29

(3-(dimethylamino)-4-nitrophenyl)(morpholino)-methanone (D29)

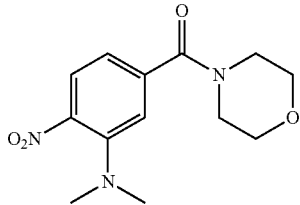 [SMILES: CN(C)c1cc(C(=O)N2CCOCC2)ccc1[N+](=O)[O-]]

To a solution of (3-fluoro-4-nitrophenyl)(morpholino)methanone (which may be prepared according to D21) (600 mg, 2.360 mmol) and di-methylamine hydrochloride (231 mg, 2.83 mmol) in DMF (5.0 mL) was added cesium carbonate (2307 mg, 7.08 mmol). The mixture was stirred overnight at 90° C. The reaction was quenched with water and extracted with DCM (20 mL×3). The combined extracts were dried over Na$_2$SO$_4$, filtered and concentrated in vacuum. The crude was purified by column chromatography on silica gel (DCM:CH$_3$OH=20:1) to give the title compound D29 (500 mg, 1.762 mmol, 74.7% yield) as yellow oil.

LCMS: 280.1 [M+H]$^+$. $t_R$=1.07. (LCMS condition 2)

Description D30

(3-ethoxy-4-nitrophenyl)(morpholino)-methanone (D30)

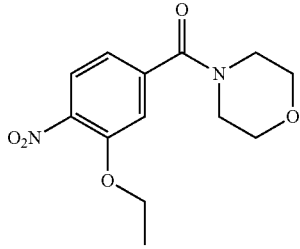 [SMILES: CCOc1cc(C(=O)N2CCOCC2)ccc1[N+](=O)[O-]]

To a solution of (3-fluoro-4-nitrophenyl)(morpholino)methanone (which may be prepared according to D21) (600 mg, 2.360 mmol) in THF (10 mL) was added sodium hydride (104 mg, 2.60 mmol) at 0° C. After stirred at 0° C. for 30 min, ethanol (120 mg, 2.60 mmol) was added. The mixture was then stirred overnight at room temperature. The reaction was quenched with aqueous NaHCO$_3$ and extracted with DCM (20 mL×3). The combined extracts were dried over Na$_2$SO$_4$, filtered and concentrated in vacuum. The crude was purified by column chromatography on silica gel (DCM:CH$_3$OH=20:1) to give the title compound D30 (500 mg, 1.701 mmol, 72.1% yield) as yellow oil.

LCMS: 281.1[M+H]$^+$. $t_R$=1.09. (LCMS condition 2)

Description D31

(3-isopropoxy-4-nitrophenyl)(morpholino)-methanone (D31)

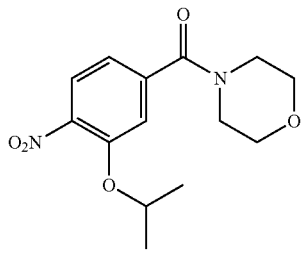 [SMILES: CC(C)Oc1cc(C(=O)N2CCOCC2)ccc1[N+](=O)[O-]]

To a solution of (3-fluoro-4-nitrophenyl)(morpholino)methanone (which may be prepared according to D21) (600 mg, 2.360 mmol) in THF (10 mL) was added sodium hydride (104 mg, 2.60 mmol) at 0° C. After stirred at 0° C. for 30 min, propan-2-ol (156 mg, 2.60 mmol) was added. The mixture was then stirred overnight at 25° C. The reaction was quenched with aqueous NaHCO$_3$ and extracted with DCM (20 mL×3). The organic layers were combined and dried by Na$_2$SO$_4$. The solution was filtered and concentrated in vacuum. The crude was purified by column chromatography on silica gel (DCM:CH$_3$OH=20:1) to give the title compound D31 (400 mg, 1.029 mmol, 43.6% yield) as yellow oil.

LCMS: 295.1 [M+H]$^+$. $t_R$=1.65. (LCMS condition 2)

Description D32

(3-isopropoxy-4-nitrophenyl)(4-methylpiperazin-1-yl)-methanone (D32)

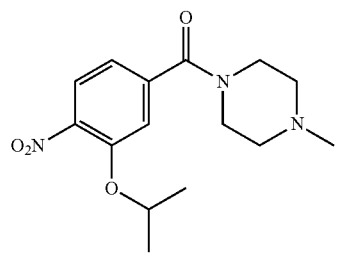 [SMILES: CC(C)Oc1cc(C(=O)N2CCN(C)CC2)ccc1[N+](=O)[O-]]

To a solution of (3-fluoro-4-nitrophenyl)(4-methylpiperazin-1-yl)methanone (which may be prepared according to D12) (400 mg, 1.497 mmol) in THF (10 mL) was added propan-2-ol (0.228 mL, 2.99 mmol) and cesium carbonate (975 mg, 2.99 mmol). The reaction was stirred overnight at room temperature. The mixture was poured into EtOAc (25 mL) and washed with water (30 mL×3). The organic layer was dried and evaporated in vacuum to give the title compound D32 (500 mg, 0.732 mmol, 48.9% yield) as yellow oil.

LCMS: 308 [M+H]$^+$. $t_R$=1.47. (LCMS condition 2)

Description D33

(3-ethoxy-4-nitrophenyl)(4-methylpiperazin-1-yl)-methanone (D33)

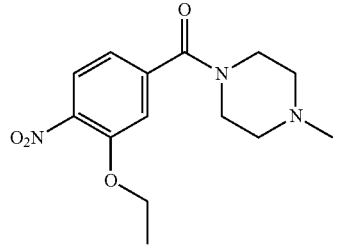 [SMILES: CCOc1cc(C(=O)N2CCN(C)CC2)ccc1[N+](=O)[O-]]

To a solution of (3-fluoro-4-nitrophenyl)(4-methylpiperazin-1-yl)methanone (which may be prepared according to D12) (400 mg, 1.497 mmol) in THF (10 mL) was added EtOH (0.874 mL, 14.97 mmol) and cesium carbonate (975 mg, 2.99 mmol). The mixture was stirred overnight at room temperature. The reaction mixture was poured into EtOAc (25 mL) and washed with water (30 mL×3). The organic layer was dried and evaporated in vacuum to give the title compound D33 (300 mg, 1.023 mmol, 68.3% yield) as yellow oil.

LCMS: 294 [M+H]$^+$. $t_R$=1.41. (LCMS condition 2)

Description D34

(3-(dimethylamino)-4-nitrophenyl)(4-methylpiperazin-1-yl)-methanone (D34)

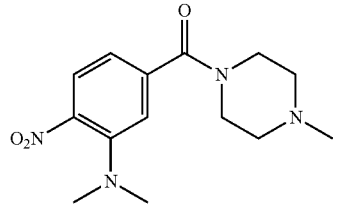 [SMILES: CN1CCN(C(=O)c2ccc([N+](=O)[O-])c(N(C)C)c2)CC1]

To a solution of (3-fluoro-4-nitrophenyl)(4-methylpiperazin-1-yl)methanone (which may be prepared according to D12) (400 mg, 1.497 mmol) in THF (10 mL) was added dimethylamine, hydrochloride (122 mg, 1.497 mmol) and cesium carbonate (975 mg, 2.99 mmol). The mixture was stirred overnight at room temperature. The reaction mixture was poured into EtOAc (25 mL) and washed with water (30 mL×3). The organic layer was dried by Na$_2$SO$_4$ and evaporated in vacuum to give the title compound D34 (380 mg, 1.300 mmol, 87% yield) as yellow oil.

LCMS: 293 [M+H]$^+$. $t_R$=1.38. (LCMS condition 2)

Description D35

6-carboxy-2-hydroxy-3-nitrobenzenediazonium (D35)

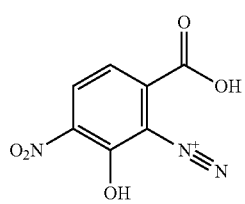 [SMILES: N#[N+]c1c(C(=O)O)ccc([N+](=O)[O-])c1O]

To a solution of 2-amino-4-nitrobenzoic acid (5 g, 27.5 mmol) in sulfuric acid (10 ml, 188 mmol) was added nitric acid (0.8 mL, 18.79 mmol) at −10° C. The mixture was stirred until the precipitate was formed. The mixture was poured into ice and extracted with ether. The ether solution was washed with water and dried over Na$_2$SO$_4$, evaporated to give the title compound D35 (7.0 g, 24.27% yield), which was used in the next step directly.

LCMS: 211 [M+H]$^+$. $t_R$=0.389. (LCMS condition 2)

Description D36

2-chloro-3-hydroxy-4-nitrobenzoic acid (D36)

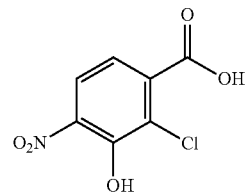 [SMILES: O=C(O)c1ccc([N+](=O)[O-])c(O)c1Cl]

To a solution of 6-carboxy-2-hydroxy-3-nitrobenzenediazonium (which may be prepared according to D35) (1.2 g, 5.71 mmol) and hydrogen chloride (10 ml, 120 mmol) was added copper (I) chloride (0.594 g, 6.00 mmol). The reaction mixture was stirred at 70° C. for 4 hours. Solvent was evaporated and the residue was purified by Biotage to give the title compound D36 (400 mg, 1.839 mmol, 32.2% yield) as a yellow solid.

LCMS: 218 [M+H]$^+$. $t_R$=0.669. (LCMS condition 2)

Description D37 methyl 2-chloro-3-methoxy-4-nitrobenzoate (D37)

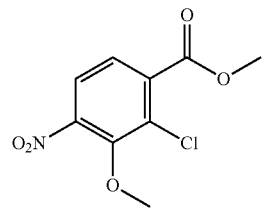 [SMILES: COC(=O)c1ccc([N+](=O)[O-])c(OC)c1Cl]

To a solution of 2-chloro-3-hydroxy-4-nitrobenzoic acid (which may be prepared according to D36) (150 mg, 0.689 mmol) in DMF (3 mL) was added sodium hydride (66.2 mg, 2.76 mmol) under nitrogen. The reaction mixture was stirred at 20° C. for 0.5 hour. Then iodomethane (391 mg, 2.76 mmol) was added and the mixture was stirred at room temperature for further 3 hours. The mixture was partitioned between ethyl acetate and water. The organic layer was dried by Na$_2$SO$_4$ and evaporated to give the title compound D37 (120 mg, 0.342 mmol, 49.6% yield).

LCMS: 246 [M+H]$^+$. $t_R$=1.332. (LCMS condition 1)

Description D38

2-chloro-3-methoxy-4-nitrobenzoic acid (D38)

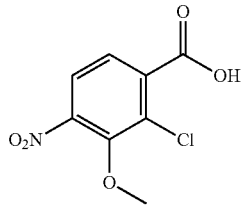

A solution of methyl 2-chloro-3-methoxy-4-nitrobenzoate (which may be prepared according to D37)(130 mg, 0.529 mmol), sodium hydroxide (1 mL, 2.0 mmol, 2M in water) in methanol (3 mL) was stirred for 3 hours at room temperature. Solvent was evaporated and the crude product was dissolved in water, washed with ethyl acetate. The water layer was adjusted to pH=3 and extracted with ethyl acetate. The organic layer was dried and evaporated to give the title compound D38 (126 mg, 0.506 mmol, 96% yield) as a yellow solid.

LCMS: 232 [M+H]$^+$. $t_R$=0.857. (LCMS condition 2)

Description D39

(2-chloro-3-methoxy-4-nitrophenyl)(4-methylpiperazin-1-yl)-methanone (D39)

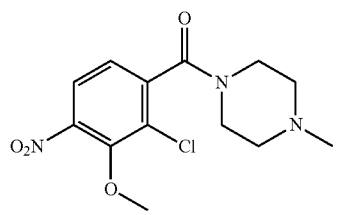 [SMILES: COc1c([N+](=O)[O-])ccc(C(=O)N2CCN(C)CC2)c1Cl]

To a solution of 2-chloro-3-methoxy-4-nitrobenzoic acid (which may be prepared according to D38) (200 mg, 0.864 mmol), N-ethyl-N-isopropylpropan-2-amine (112 mg, 0.864 mmol) and 1-methylpiperazine (86 mg, 0.864 mmol) in THF (5 mL) was added HATU (328 mg, 0.864 mmol). The reaction mixture was stirred at room temperature for 3 hours. The mixture was purified by Biotage column to give the title compound D39 (200 mg, 0.637 mmol, 73.8% yield) as a white solid.

LCMS: 314 [M+H]$^+$. $t_R$=0.701. (LCMS condition 2)

Description D40

(3-methoxy-4-nitrophenyl)(2,7-diazaspiro-[3.5]-nonan-7-yl)-methanone (D40)

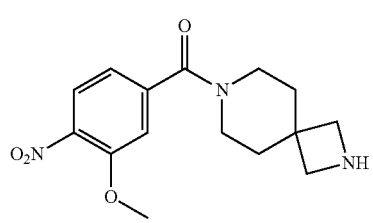 [SMILES: COc1cc(C(=O)N2CCC3(CC2)CNC3)ccc1[N+](=O)[O-]]

To the solution of tert-butyl 7-(3-methoxy-4-nitrobenzoyl)-2,7-diazaspiro[3.5]nonane-2-carboxylate (which may be prepared according to D9) (250 mg, 0.617 mmol) in DCM (10 mL) was added TFA (0.238 mL, 3.08 mmol) at room temperature. The mixture was stirred overnight at room temperature. DCM was removed under vacuum. The residue was dissolved in water and adjusted pH=9 with 1M NaOH solution. The mixture was then extracted with EA twice. The combined organic layer was then washed with water and brine, dried over Na$_2$SO$_4$ and concentrated to give the title compound D40 (157 mg, 0.514 mmol, 83% yield), which was used directly in next step without further purification.

LCMS: 306[M+H]$^+$. $t_R$=1.643. (LCMS condition 1)

Description D41

(3-methoxy-4-nitrophenyl)(2-methyl-2,7-diazaspiro-[3.5]-nonan-7-yl)methanone (D41)

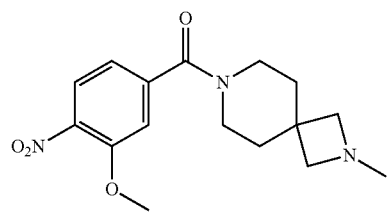 [SMILES: COc1cc(C(=O)N2CCC3(CC2)CN(C)C3)ccc1[N+](=O)[O-]]

To a solution of (3-methoxy-4-nitrophenyl)(2,7-diazaspiro-[3.5]-nonan-7-yl)-methanone (which may be prepared according to D40) (157 mg, 0.514 mmol) in DMF (5 mL) was added acetic acid (0.029 mL, 0.514 mmol). The reaction was stirred at room temperature for 1 hour. Then to this mixture was added sodium triacetoxyborohydride (218 mg, 1.028 mmol) portionwise. The mixture was stirred overnight at room temperature. The reaction was quenched with sat NH$_4$Cl solution and evaporated. The crude product was purified directly via reverse phase chromatography (Biotage SNAP Cartridge, KP-C18-HS 120 g, 5%~95% MeCN/H$_2$O (0.05% ammonia)) to give the title compound D41 (69 mg, 0.216 mmol, 42.0% yield) as yellow oil.

LCMS: 320[M+H]$^+$. $t_R$=1.630. (LCMS condition 1)

Description D42

(S)-tert-butyl 4-(3-methoxy-4-nitrobenzoyl)-2-methylpiperazine-1-carboxylate (D42)

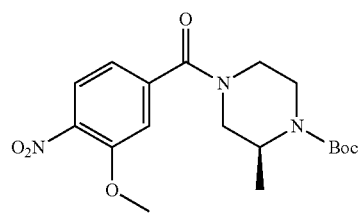 [SMILES: COc1cc(C(=O)N2CCN(C(=O)OC(C)(C)C)[C@@H](C)C2)ccc1[N+](=O)[O-]]

To a solution of HOBT (0.777 g, 5.07 mmol), EDC (0.972 g, 5.07 mmol), TEA (0.707 mL, 5.07 mmol) and 3-methoxy-4-nitrobenzoic acid (1 g, 5.07 mmol) in DMF (20 mL) was added (S)-tert-butyl 2-methylpiperazine-1-carboxylate (1.016 g, 5.07 mmol). The reaction was stirred at room temperature for 3 hours. The mixture was partitioned between ethyl acetate (50 mL) and water (25 mL). The organic layer was washed with water (25 mL), saturated NaHCO$_3$ (25 mL) and brine (25 mL), dried over Na$_2$SO$_4$ and evaporated in vacuum to give the title compound D42 (1.78 g, 3.61 mmol, 71.2% yield) as orange oil.

LCMS: 380[M+H]$^+$. t$_R$=1.325. (LCMS condition 2)

Description D43

(S)-(3-methoxy-4-nitrophenyl)-(3-methylpiperazin-1-yl)-methanone (D43)

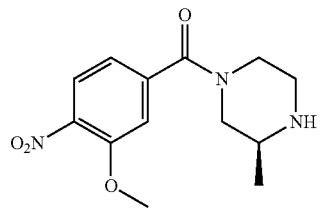 [SMILES: COc1cc(C(=O)N2CCN[C@@H](C)C2)ccc1[N+](=O)[O-]]

To a solution of (S)-tert-butyl 4-(3-methoxy-4-nitrobenzoyl)-2-methylpiperazine-1-carboxylate (which may be prepared according to D42) (1.78 g, 4.69 mmol) in DCM (20 mL) was added TFA (2 mL). The reaction was stirred overnight at room temperature. The mixture was partitioned between DCM (25 mL) and water (20 mL). The organic layer was washed with water (20 mL), dried over Na$_2$SO$_4$ and evaporated in vacuum to give the title compound D43 (700 mg, 1.679 mmol, 75% yield) as a white solid.

LCMS: 280[M+H]$^+$. t$_R$=1.095. (LCMS condition 1)

Description D44

(S)-(3,4-dimethylpiperazin-1-yl)-(3-methoxy-4-nitrophenyl)-methanone (D44)

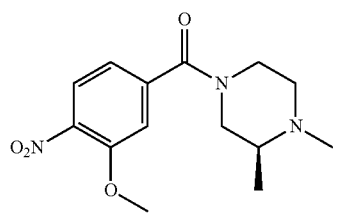 [SMILES: COc1cc(C(=O)N2CCN(C)[C@@H](C)C2)ccc1[N+](=O)[O-]]

To a solution of K$_2$CO$_3$ (129 mg, 2.148 mmol), (S)-(3-methoxy-4-nitrophenyl)-(3-methylpiperazin-1-yl)-methanone (which may be prepared according to D43) in acetonitrile (20 mL) was added iodomethane (0.067 mL, 1.074 mmol) dropwise. The reaction was stirred at room temperature for 3 hours. The mixture was filtered and solution was partitioned between ethyl acetate (25 mL) and water (10 mL). The organic layer was dried over Na$_2$SO$_4$ and evaporated in vacuum to give the title compound D44 (200 mg, 0.682 mmol, 63.5% yield) as yellow oil.

LCMS: 294[M+H]$^+$. t$_R$=1.054. (LCMS condition 2)

$^1$H NMR (400 MHz, METHANOL-d$_4$): δ 7.88 (d, J=8.0 Hz, 1H), 7.34 (s, 1H), 7.11 (d, J=8.0 Hz, 1H), 4.42 (br. s., 1H), 3.99 (s, 3H), 3.49 (m, 1H), 3.35-3.40 (m, 1H), 2.90-3.22 (m, 1H), 2.79 (d, J=11.3 Hz, 1H), 2.09-2.42 (m, 5H), 0.82-1.27 (m, 3H).

Description D45

(R)-(3-methoxy-4-nitrophenyl)-(3-methylpiperazin-1-yl)methanone (D45)

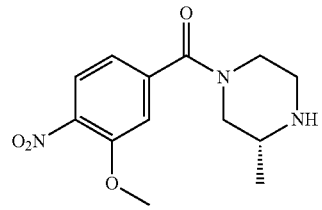 [SMILES: COc1cc(C(=O)N2CCN[C@H](C)C2)ccc1[N+](=O)[O-]]

A mixture of (R)-tert-butyl 4-(3-methoxy-4-nitrobenzoyl)-2-methyl piperazine-1-carboxylate (which may be prepared according to D15) (1.5 g, 3.95 mmol) and HCl (5 mL, 20.00 mmol, 4M in dioxane) in methanol (5 mL) was heated at 60° C. for 2 hours. The mixture was concentrated to give the title compound D45 (1.0 g, 3.44 mmol, 87% yield).

LCMS: 280[M+H]$^+$. t$_R$=1.272. (LCMS condition 2)

Description D46

(R)-(3,4-dimethylpiperazin-1-yl)-(3-methoxy-4-nitrophenyl)methanone (D46)

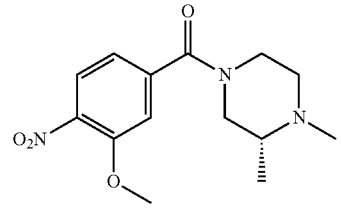 [SMILES: COc1cc(C(=O)N2CCN(C)[C@H](C)C2)ccc1[N+](=O)[O-]]

A mixture of formaldehyde (0.108 g, 3.58 mmol) and (R)-(3-methoxy-4-nitrophenyl)-(3-methylpiperazin-1-yl) methanone (which may be prepared according to D45) (1.0 g, 3.58 mmol) in methanol was stirred at 60° C. for 1 hour. The mixture was then cooled to 0° C. and NaCNBH$_4$ (0.225 g, 3.58 mmol) was added. The reaction was stirred overnight at room temperature. The mixture was concentrated and directly purified by pre-HPLC to give the title compound D46 (600 mg, 2.046 mmol, 57.1% yield) as oil.

LCMS: 294 [M+H]$^+$. t$_R$=1.371. (LCMS condition 2)

Description D47

(±)-3-azabicyclo-[3.1.0]-hexan-1-ylmethanol, trifluoroacetic acid salt (D47)

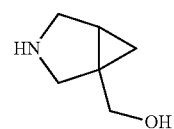

To a solution of tert-butyl 1-(hydroxymethyl)-3-azabicyclo[3.1.0]hexane-3-carboxylate (220 mg, 1.032 mmol) (which could be prepared following the procedures described in Korean Journal of Medicinal Chemistry, 4(2), 119-25; 1994) in DCM (20 mL) was added TFA (0.397 mL, 5.16 mmol). The mixture was stirred overnight at room temperature. The mixture was then concentrated to give the title compound D47 (235 mg, 1.034 mmol, 100% yield) as yellow oil, which used in next step without further purification.

LCMS: 114 [M+H]$^+$. $t_R$=0.247 (LCMS condition 1)

$^1$H NMR (400 MHz, CHLOROFORM-d): δ 3.80-3.89 (m, 1H), 3.67-3.73 (m, 1H), 2.86-3.10 (m, 4H), 1.27-1.34 (m, 1H), 0.65 (dd, J=7.8, 5.1 Hz, 1H), 0.49-0.56 (m, 1H).

Description D48

(±)-6-azaspiro-[2.5]-octan-5-ylmethanol (D48)

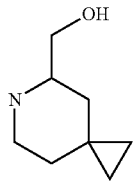

To a solution of tert-butyl 5-(hydroxymethyl)-6-azaspiro-[2.5]-octane-6-carboxylate (450 mg, 1.865 mmol) (which could be prepared following the procedures described in PCT Int. Appl., 2011006960) in DCM (10.0 mL) was added TFA (1063 mg, 9.32 mmol). The mixture was stirred at room temperature for 3 hours. The reaction was quenched with water and extracted with DCM (20 mL×3). The combined organic layer was dried over Na$_2$SO$_4$, filtered and concentrated in vacuum. The crude was purified by column chromatography on silica gel (PE:EA=4:1) to give the title compound D48 (250 mg, 1.770 mmol, 95% yield) as oil.

LCMS: 142 [M+H]$^+$. $t_R$=0.819 (LCMS condition 2)

$^1$H NMR (400 MHz, DMSO-d$_6$): δ 4.62 (s, 1H), 3.27 (m, 3H), 2.94 (m, 1H), 2.66 (m, 2H), 1.74 (m, 1H), 1.45 (m, 1H), 0.77 (m, 2H), 0.26 (m, 4H).

Description D49

(±)-6-azaspiro-[2.5]-octan-1-ylmethanol (D49)

To a solution of ethyl 6-azaspiro-[2.5]-octane-1-carboxylate (3 g, 16.37 mmol) (which could be prepared following the procedures described in PCT Int. Appl., 2008147314) in THF (3 mL) was added LiAlH$_4$ (0.932 g, 24.56 mmol). The mixture was stirred at room temperature for 2 hours. Sat. Na$_2$SO$_4$ solution (1 mL) was added. The mixture was filtered and the solution washed with EA, dried with Na$_2$SO$_4$, evaporated in vacuum to give the title compound D49 (2.5 g, 10.27 mmol, 62.7% yield) as yellow oil.

LCMS: 142.2 [M+H]$^+$. $t_R$=0.46 (LCMS condition 2)

Description D50

(±)-(1-(hydroxymethyl)-6-azaspiro-[2.5]-octan-6-yl)-(3-methoxy-4-nitrophenyl)methanone (D50)

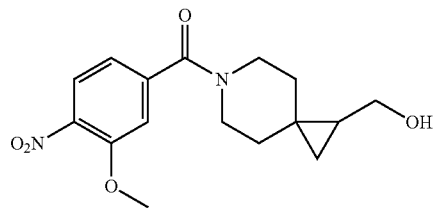 [SMILES: COc1cc(C(=O)N2CCC3(CC2)CC3CO)ccc1[N+](=O)[O-]]

To a solution of (±)-6-azaspiro-[2.5]-octan-1-ylmethanol (which may be prepared according to D49)(2.5 g, 17.70 mmol) and 3-methoxy-4-nitrobenzoic acid (3.14 g, 15.93 mmol) in DMF (15 mL) was added HATU (13.46 g, 35.4 mmol) and DIPEA (4.58 g, 35.4 mmol). The reaction was stirred at 0° C. for 1 hour. The mixture was poured into water (50 mL) and extracted with EtOAc (40 mL) twice. The organic layers were combined, dried and evaporated in vacuum. The crude was purified by prep-HPLC to give the title compound D50 (370 mg, 1.074 mmol, 6.07% yield) as yellow oil.

LCMS: 321 [M+H]$^+$. $t_R$=1.466 (LCMS condition 2)

$^1$H NMR (400 MHz, CHLOROFORM-d): δ 7.87 (d, J=8.0 Hz, 1H), 7.14 (s, 1H), 7.01 (d, J=8.0 Hz, 1H), 5.30 (s, 1H), 3.26-4.10 (m, 9H), 1.67-1.84 (m, 1H), 1.18-1.51 (m, 3H), 0.54-0.73 (m, 1H), 0.21-0.39 (m, 1H).

Description D51

(±)-(3-methoxy-4-nitrophenyl)(1-(methoxymethyl)-6-azaspiro-[2.5]-octan-6-yl)methanone(D51)

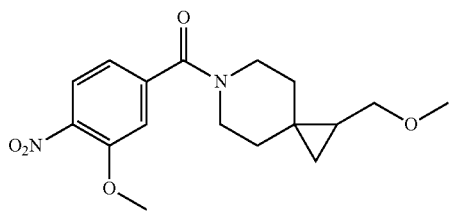 [SMILES: COCC1CC12CCN(C(=O)c1ccc([N+](=O)[O-])c(OC)c1)CC2]

To a solution of (±)-(1-(hydroxymethyl)-6-azaspiro-[2.5]-octan-6-yl)-(3-methoxy-4-nitrophenyl)methanone (which may be prepared according to D50) (350 mg, 1.093 mmol) in THF (3 mL) was added sodium hydride (52.4 mg, 1.311 mmol) at 0° C. under nitrogen atmosphere. After stirring under 0° C. for 10 min, iodomethane (775 mg, 5.46 mmol) was added. The mixture was then stirred overnight at room temperature. The reaction was quenched with ice water and diluted with ethyl acetate (50 mL). The ethyl acetate layer was washed with water (30 mL×2), brine (30 mL) and dried over Na$_2$SO$_4$. Solvent was evaporated in vacuum to give the title compound D51 (150 mg, 0.426 mmol, 39.0% yield) as yellow oil.

LCMS: 335 [M+H]$^+$. $t_R$=1.668 (LCMS condition 2)

General Procedure 2 for Nitro Reduction (D52-D79)

To a solution of nitro-product (1.0 eq) in methanol (20 mL) was added Pd/C (0.03 eq), the mixture was stirred overnight at room temperature under hydrogen. The mixture was filtered and the solution was concentrated in vacuum to give the crude product amine D52-D79, which was used in the next step without further purification.

| | Structure/name | Starting material | [M + H]$^+$ | Yield (%) |
|---|---|---|---|---|
| D52 | 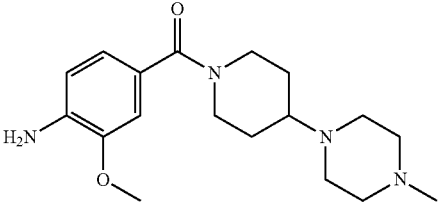<br>(4-amino-3-methoxyphenyl)(4-(4-methylpiperazin-1-yl)piperidin-1-yl)methanone | D3 | 333 | 98 |
| D53 | 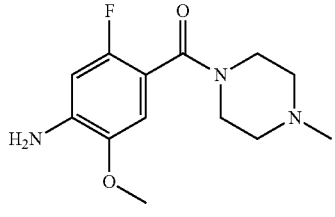<br>(4-amino-2-fluoro-5-methoxyphenyl)(4-methylpiperazin-1-yl)methanone | D4 | 268 | 65 |
| D54 | 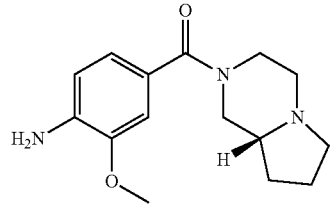<br>(S)-(4-amino-3-methoxyphenyl)(hexahydropyrrolo[1,2-a]pyrazin-2(1H)-yl)methanone | D5 | 276 | 58 |
| D55 | 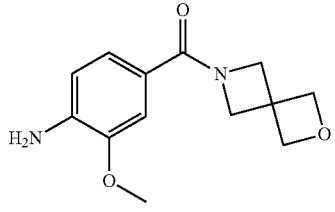<br>(4-amino-3-methoxyphenyl)(2-oxa-6-azaspiro[3.3]heptan-6-yl)methanone | D6 | 249 | 100 |
| D56 | 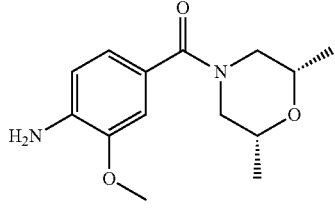<br>(4-amino-3-methoxyphenyl)((2R,6S)-2,6-dimethylmorpholino)methanone | D7 | 265 | 94 |

| | Structure/name | Starting material | [M + H]+ | Yield (%) |
|---|---|---|---|---|
| D57 | 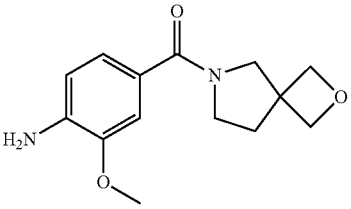<br>(4-amino-3-methoxyphenyl)(2-oxa-6-azaspiro[3.4]octan-6-yl)methanone | D8 | 263 | 85 |
| D58 | 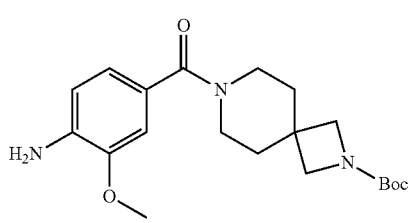<br>tert-butyl 7-(4-amino-3-methoxybenzoyl)-2,7-diazaspiro[3.5]nonane-2-carboxylate | D9 | 376 | 77 |
| D59 | 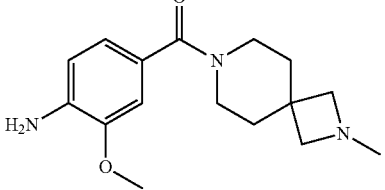<br>(4-amino-3-methoxyphenyl)(2-methyl-2,7-diazaspiro[3.5]nonan-7-yl)methanone | D41 | 290 | 90 |
| D60 | 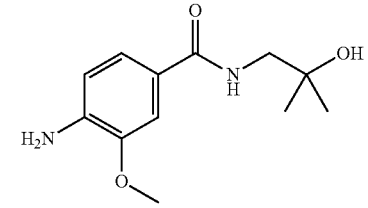<br>4-amino-N-(2-hydroxy-2-methylpropyl)-3-methoxybenzamide | D10 | 239 | 79 |
| D61 | 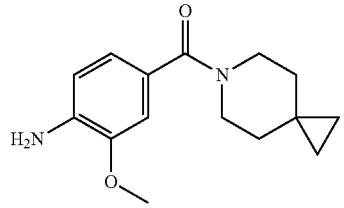<br>(4-amino-3-methoxyphenyl)(6-azaspiro[2.5]octan-6-yl)methanone | D11 | 261 | 82 |

-continued

| | Structure/name | Starting material | [M + H]+ | Yield (%) |
|---|---|---|---|---|
| D62 | 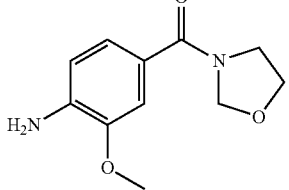<br>(4-amino-3-methoxyphenyl)(oxazolidin-3-yl)methanone | D28 | 223 | 45 |
| D63 | 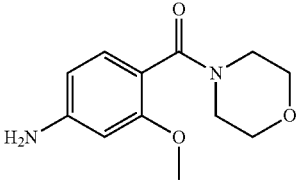<br>(4-amino-2-methoxyphenyl)(morpholino)methanone | (2-methoxy-4-nitro-phenyl)(morpholino)-methanone | 237 | 99 |
| D64 | 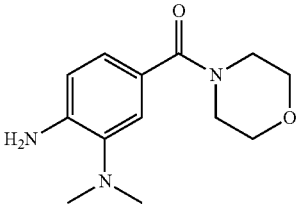<br>(4-amino-3-(dimethylamino)phenyl)(morpholino)methanone | D29 | 250 | 90 |
| D65 | 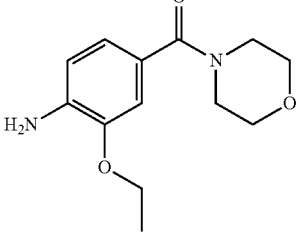<br>(4-amino-3-ethoxyphenyl)(morpholino)methanone | D30 | 251 | 88 |
| D66 | 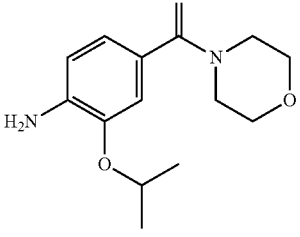<br>(4-amino-3-isopropoxyphenyl)(morpholino)methanone | D31 | 265 | 65 |

|     | Structure/name | Starting material | [M + H]+ | Yield (%) |
| --- | --- | --- | --- | --- |
| D67 | (4-amino-3-fluorophenyl)(4-methylpiperazin-1-yl)methanone | D12 | 238 | 46 |
| D68 | (4-amino-3-isopropoxyphenyl)(4-methylpiperazin-1-yl)methanone | D32 | 278 | 89 |
| D69 | (4-amino-3-ethoxyphenyl)(4-methylpiperazin-1-yl)methanone | D33 | 264 | 93 |
| D70 | (4-amino-3-(dimethylamino)phenyl)(4-methylpiperazin-1-yl)methanone | D34 | 263 | 59 |
| D71 | (S)-(4-amino-3-methoxyphenyl)(3-methylmorpholino)methanone | D13 | 251 | 97 |

-continued

| | Structure/name | Starting material | [M + H]+ | Yield (%) |
|---|---|---|---|---|
| D72 | 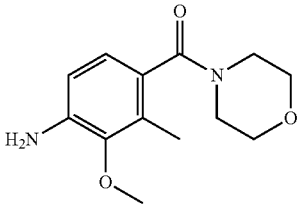<br>(4-amino-3-methoxy-2-methylphenyl)(morpholino)methanone | D14 | 251 | 98 |
| D73 | 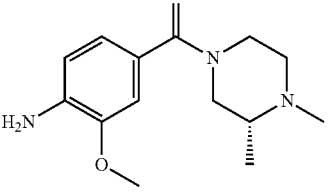<br>(R)-(4-amino-3-methoxyphenyl)(3,4-dimethylpiperazin-1-yl)methanone | D46 | 264 | 77 |
| D74 | 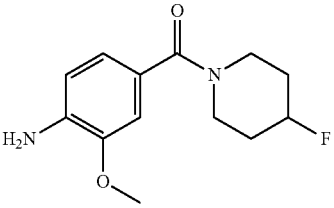<br>(4-amino-3-methoxyphenyl)(4-fluoropiperidin-1-yl)methanone | D17 | 253 | 86 |
| D75 | 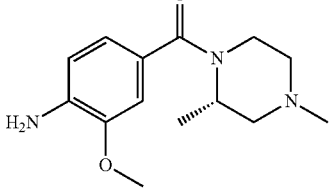<br>(S)-(4-amino-3-methoxyphenyl)(2,4-dimethylpiperazin-1-yl)methanone | D18 | 264 | 48 |
| D76 | 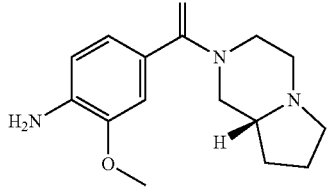<br>(R)-(4-amino-3-methoxyphenyl)(hexahydropyrrolo[1,2-a]pyrazin-2(1H)-yl)methanone | D19 | 276 | 92 |

| | Structure/name | Starting material | [M + H]⁺ | Yield (%) |
|---|---|---|---|---|
| D77 | 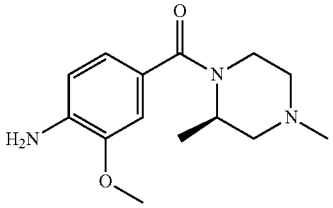<br>(R)-(4-amino-3-methoxyphenyl)(2,4-dimethylpiperazin-1-yl)methanone | D20 | 264 | 95 |
| D78 | 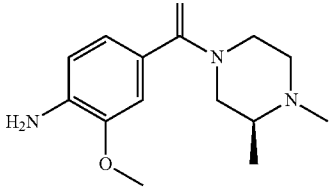<br>(S)-(4-amino-3-methoxyphenyl)(3,4-dimethylpiperazin-1-yl)methanone | D44 | 264 | 67 |
| D79 | 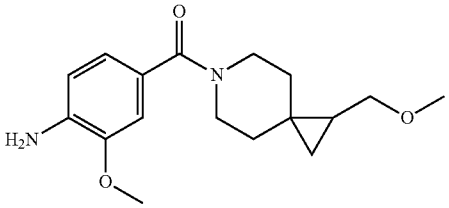<br>(4-amino-3-methoxyphenyl)(1-(methoxymethyl)-6-azaspiro[2.5]octan-6-yl)methanone | D51 | 305 | 68 |

Description D80

(4-amino-3-(difluoromethoxy)-phenyl)(4-methylpiperazin-1-yl)-methanone (D80)

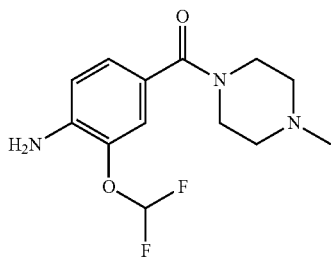 [SMILES: CN1CCN(C(=O)c2ccc(N)c(OC(F)F)c2)CC1]

A solution of (3-(difluoromethoxy)-4-nitrophenyl)-(4-methylpiperazin-1-yl)methanone (which may be prepared according to D24) (150 mg, 0.476 mmol), iron (80 mg, 1.427 mmol) in acetic acid (2 mL) was stirred at 70° C. for 2 hours. The mixture was diluted with EA (10 mL) and filtered. The solution was then washed with saturated NaHCO₃ solution and brine. The organic layer was dried over Na₂SO₄ and concentrated to give the title product D80 (100 mg, 0.351 mmol, 73.7% yield) as yellow oil.

LCMS: 286[M+H]⁺. $t_R$=1.024 (LCMS condition 1)

¹H NMR (400 MHz, METHANOL-d₄): δ 6.97-7.08 (m, 2H), 6.42-6.86 (m, 2H), 3.56 (br. s., 4H), 2.40 (d, J=4.4 Hz, 4H), 2.24 (s, 3H).

Description D81

(4-amino-3-(cyclopropylmethoxy)-phenyl)(4-methylpiperazin-1-yl)-methanone (D81)

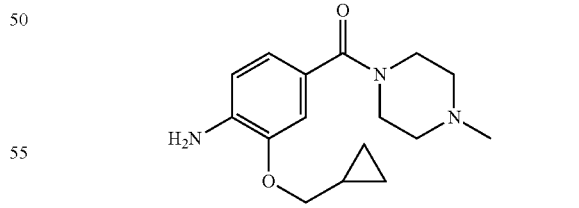

A solution of (3-(cyclopropylmethoxy)-4-nitrophenyl)(4-methylpiperazin-1-yl)-methanone (which may be prepared according to D27) (480 mg, 0.812 mmol), iron (136 mg, 2.435 mmol) in acetic acid (2 mL) was stirred at 70° C. for 2 hours. The reaction was diluted with EA (10 mL) and filtered. The solution was then washed with saturated NaHCO₃ solution and brine. The organic layer was dried over Na₂SO₄ and concentrated to give the title compound D81 (210 mg, 0.726 mmol, 89% yield) as yellow oil.

LCMS: 290[M+H]⁺. $t_R$=1.435 (LCMS condition 1)

Description D82

(R)-(4-amino-3-methoxyphenyl)(3-methylmorpholino)-methanone (D82)

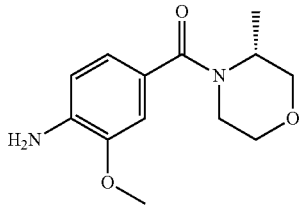 [SMILES: COc1cc(C(=O)N2CCOC[C@H]2C)ccc1N]

A mixture of (R)-(3-methoxy-4-nitrophenyl)(3-methylmorpholino)methanone (which may be prepared according to D16) (50 mg, 0.178 mmol), ammonia hydrochloride (9.54 mg, 0.178 mmol) and iron (49.8 mg, 0.892 mmol) in ethanol (10 mL) was stirred overnight at 70° C. under nitrogen. The mixture was filtered and the solution was concentrated. The crude was purified by chromatography on silica gel (DCM: MeOH=10:1) to give the title compound D82 (30 mg, 0.120 mmol, 67.2% yield) as oil.

LCMS: 251[M+H]$^+$. $t_R$=1.248 (LCMS condition 2)

Description D83

(4-amino-2-chloro-3-methoxyphenyl)(4-methylpiperazin-1-yl)-methanone (D83)

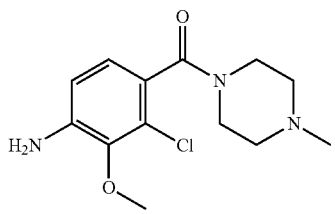

A mixture of (2-chloro-3-methoxy-4-nitrophenyl)(4-methylpiperazin-1-yl)-methanone (which may be prepared according to D39) (108 mg, 0.344 mmol) and iron (96 mg, 1.721 mmol) in ethanol (2.0 mL) and water (2.0 mL) was stirred overnight at 65° C. under nitrogen. The mixture was concentrated and the residue was dissolved in EtOH and filtered. The solution was evaporated to give the title compound D83 (100 mg, 0.247 mmol, 71.7% yield) as yellow oil, which was used in the next step directly.

LCMS: 284[M+H]$^+$. $t_R$=1.24 (LCMS condition 1)

Description D84

2-chloro-4-ethoxy-5-iodo-7H-pyrrolo-[2,3-d]-pyrimidine (D84)

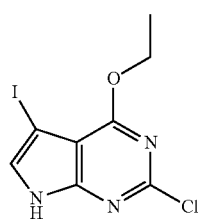

To a solution of 2-chloro-4-ethoxy-7H-pyrrolo-[2,3-d] pyrimidine (which may be prepared according to D1) (600 mg, 3.04 mmol) in DCM (50 mL) was added NIS (751 mg, 3.34 mmol). The mixture was stirred at 25° C. for 3 hours. The reaction was quenched with water (30 mL) and extracted with DCM (80 mL). The organic layer was washed with 10% Na$_2$SO$_4$ solution (80 mL) and concentrated in vacuum to get the title compound D84 (700 mg, 1.861 mmol, 61.3% yield) as a yellow solid.

LCMS: 324 [M+H]$^+$. $t_R$=1.400 (LCMS condition 1)
$^1$H NMR (400 MHz, DMSO-d$_6$): δ 7.59 (d, J=2.4 Hz, 1H), 4.51 (q, J=7.1 Hz, 2H), 1.40 (t, 3H).

Description D85

2-chloro-4-ethoxy-5-iodo-7-tosyl-7H-pyrrolo-[2,3-d]-pyrimidine (D85)

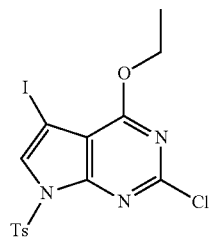 [SMILES: CCOc1nc(Cl)nc2c1c(I)cn2S(=O)(=O)c1ccc(C)cc1]

To a solution of 2-chloro-4-ethoxy-5-iodo-7H-pyrrolo-[2,3-d]-pyrimidine (which may be prepared according to D84) (600 mg, 1.855 mmol) in DMF (30 mL) was added NaH (89 mg, 3.71 mmol) at 0° C. The mixture was stirred for 30 min, and then TsCl (707 mg, 3.71 mmol) was added. The mixture was warmed to room temperature and stirred for further 4 hours. The reaction was quenched with water (30 mL) extracted with EtOAc. The organic layer was washed with brine, dried over Na$_2$SO$_4$, concentrated in vacuum to give the title compound D85 (800 mg, 1.574 mmol, 85% yield) as a yellow solid.

LCMS: 478 [M+H]$^+$. $t_R$=1.733 (LCMS condition 2)

Description D86

2-chloro-4-ethoxy-5-methyl-7-tosyl-7H-pyrrolo-[2,3-d]-pyrimidine (D86)

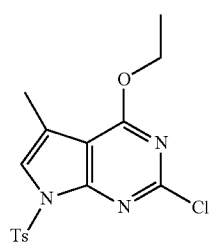 [SMILES: CCOc1nc(Cl)nc2c1c(C)cn2S(=O)(=O)c1ccc(C)cc1]

To a solution of 2-chloro-4-ethoxy-5-iodo-7-tosyl-7H-pyrrolo-[2,3-d]-pyrimidine (which may be prepared according to D85) (800 mg, 1.675 mmol), methylboronic acid (200 mg, 3.35 mmol), K$_2$CO$_3$ (694 mg, 5.02 mmol) in 1,4-dioxane (100 mL) and water (10.00 mL) was added Pd(Ph$_3$P)$_4$ (194 mg, 0.167 mmol). The mixture was stirred overnight at 90° C. under nitrogen. The mixture was cooled to room temperature and added H$_2$O (80 mL), extracted with EtOAc. The organic layer was concentrated and purified by column chromatography on silica gel (PE:EA=5:1) to give the title compound D86 (40 mg, 0.109 mmol, 6.53% yield) as a yellow solid.

LCMS: 366[M+H]$^+$. t$_R$=1.687 (LCMS condition 2)

Description D87

2-chloro-4-(cyclopropylmethoxy)-7H-pyrrolo-[2,3-d]-pyrimidine (D87)

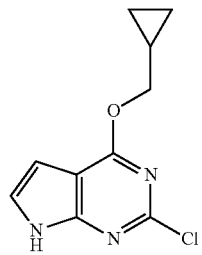 [SMILES: Clc1nc(OCC2CC2)c2cc[nH]c2n1]

To a solution of cyclopropylmethanol (1.151 g, 15.96 mmol) in THF (50 mL) was added sodium hydride (0.638 g, 15.96 mmol) at 0° C. The mixture was stirred at 0° C. for 30 min. 2,4-dichloro-7H-pyrrolo[2,3-d]pyrimidine (3.00 g, 15.96 mmol) was then added. The mixture was stirred overnight at 70° C. and then concentrated in vacuum. The residue was poured into water and extracted with DCM (20 mL×3). The combined organic layers were dried over Na$_2$SO$_4$, filtered and concentrated in vacuum. The crude was purified by column chromatography on silica gel (PE:EA=4:1) to give the title compound D87 (3.2 g, 13.84 mmol, 87% yield).

LCMS: 224.2[M+H]$^+$. t$_R$=1.44 (LCMS condition 2)
$^1$H NMR (400 MHz, DMSO-d$_6$): δ 12.20 (s, 1H), 7.37 (d, J=4.0 Hz, 1H), 6.51 (d, J=4.5 Hz, 1H), 4.29 (d, J=9.0 Hz, 2H), 1.29 (m, 1H), 0.57 (m, 2H), 0.40 (m, 2H).

Description D88

2-chloro-4-(cyclopropylmethoxy)-5-iodo-7H-pyrrolo-[2,3-d]-pyrimidine (D88)

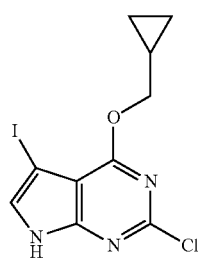 [SMILES: Clc1nc(OCC2CC2)c2c(I)c[nH]c2n1]

To the solution of 2-chloro-4-(cyclopropylmethoxy)-7H-pyrrolo-[2,3-d]-pyrimidine (which may be prepared according to D87) (700 mg, 3.13 mmol) in DCM (50 mL) was added NIS (775 mg, 3.44 mmol). The resulting mixture was stirred for 3 hours at 25° C. The mixture was quenched with water (30 mL) and extracted the aqueous layer with DCM (80 mL). The organic layer was washed with 10% Na$_2$SO$_4$ solution (80 mL) and concentrated in vacuum to give the title compound D88 (1 g, 2.60 mmol, 83% yield) as a yellow solid.

LCMS: 350[M+H]$^+$. t$_R$=1.572 (LCMS condition 2)

Description D89

2-chloro-4-(cyclopropylmethoxy)-5-iodo-7-tosyl-7H-pyrrolo-[2,3-d]-pyrimidine (D89)

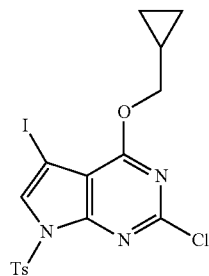 [SMILES: Cc1ccc(S(=O)(=O)n2cc(I)c3c(OCC4CC4)nc(Cl)nc32)cc1]

To an ice-cold solution of 2-chloro-4-(cyclopropylmethoxy)-5-iodo-7H-pyrrolo-[2,3-d]-pyrimidine (which may be prepared according to D88) (1 g, 2.86 mmol) in DMF (20 mL) was added sodium hydride (0.137 g, 5.72 mmol). The mixture was stirred for 30 min, and then TsCl (707 mg, 3.71 mmol) was added. The mixture was stirred for 3 hours at room temperature. The reaction was quenched with water (30 mL) and extracted with EtOAc. The organic layer was washed with brine and concentrated. The crude was purified via chromatography on silica gel (PE:EA=15:1) to give the title compound D89 (600 mg, 1.191 mmol, 41.6% yield) as a yellow solid.

LCMS: 504[M+H]$^+$. t$_R$=1.815 (LCMS condition 2)

Description D90

2-chloro-4-(cyclopropylmethoxy)-5-methyl-7-tosyl-7H-pyrrolo-[2,3-d]-pyrimidine (D90)

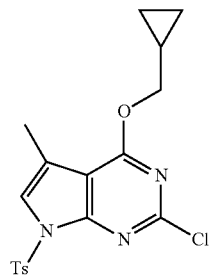 [SMILES: Cc1ccc(S(=O)(=O)n2cc(C)c3c(OCC4CC4)nc(Cl)nc32)cc1]

To a solution of 2-chloro-4-(cyclopropylmethoxy)-5-iodo-7-tosyl-7H-pyrrolo-[2,3-d]-pyrimidine (which may be prepared according to D89) (1 g, 1.985 mmol), methylboronic acid (0.238 g, 3.97 mmol) and K$_2$CO$_3$ (0.823 g, 5.96 mmol) in 1, 4-dioxane (100 mL) and water (10.00 mL) was added Pd(Ph$_3$P)$_4$ (194 mg, 0.167 mmol). The mixture was stirred overnight at 90° C. under nitrogen. Solvent was evaporated, the residue was purified by column chromatography on silica gel (PE:EA=20:1) and further purified by pre-HPLC to give the title compound D90 (28 mg, 0.071 mmol, 3.60% yield) as a yellow solid.

LCMS: 392[M+H]⁺. $t_R$=1.795 (LCMS condition 2)

Description D91

6-chloro-4-ethoxy-1H-pyrazolo-[3,4-d]-pyrimidine (D91)

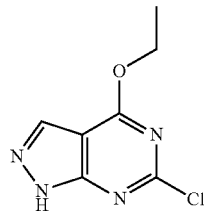

To a solution of ethanol (100 mg, 2.180 mmol) in THF (50 mL) in ice bath was added sodium hydride (134 mg, 3.35 mmol). After stirred for 15 min, 4, 6-dichloro-1H-pyrazolo-[3,4-d]-pyrimidine (317 mg, 1.677 mmol) was added. The mixture was gradually allowed to room temperature and stirred overnight. The reaction was quenched with water (5 mL), filtered, concentrated to remove solvent, diluted with ethyl acetate (80 mL) and washed with water (30 mL). The organic layer was dried over Na₂SO₄, filtered and concentrated. The residue was purified by column chromatography on silica gel (PE:EA=20:1) to give the title compound D91 (229 mg, 52.4% yield) as a white solid.

LCMS: 199[M+H]⁺. $t_R$=2.487 (LCMS condition 1)

Description D92

6-chloro-4-ethoxy-3-methyl-1H-pyrazolo-[3,4-d]-pyrimidine (D92)

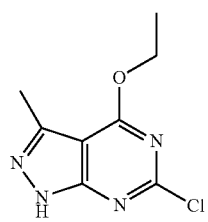

To a solution of ethanol (0.227 g, 4.93 mmol) in THF (60 mL) was added sodium hydride in ice bath. After stirred for 20 min, 4, 6-dichloro-3-methyl-1H-pyrazolo [3,4-d]pyrimidine (1 g, 4.93 mmol) was added. The mixture was gradually allowed to room temperature and stirred overnight at room temperature. The mixture was then diluted with water (20 mL), concentrated to remove solvent and diluted with ethyl acetate (220 mL). The organic layer was washed with water (60 mL×2), dried over Na₂SO₄, filtered and concentrated. The crude product (900 mg, 86% yield) was directly used into next step.

LCMS: 213[M+H]⁺. $t_R$=2.775 (LCMS condition 1)

Description D93

6-chloro-4-(cyclopropylmethoxy)-1H-pyrazolo-[3,4-d]-pyrimidine (D93)

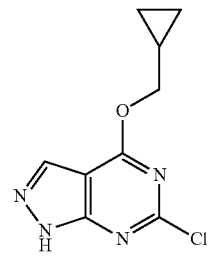 [SMILES: Clc1nc(OCC2CC2)c2cn[nH]c2n1]

To a solution of cyclopropylmethanol (1.908 g, 26.5 mmol) in THF (200 mL) was added sodium hydride (3.17 g, 79 mmol) in an ice bath. After stirred for 30 min, 4,6-dichloro-1H-pyrazolo[3,4-d]pyrimidine (5 g, 26.5 mmol). The reaction mixture was gradually allowed to room temperature and stirred overnight. Then the mixture was diluted with water (80 mL), concentrated to remove solvent and diluted with ethyl acetate (220 mL). The organic layer was washed with water (80 mL×2), dried over Na₂SO₄, filtered and concentrated. The crude (5 g, 84% yield) was directly used into next step.

LCMS: 225[M+H]⁺. $t_R$=2.918 (LCMS condition 1)

Description D94

2-chloro-4-ethoxy-7H-pyrrolo-[2,3-d]-pyrimidine-5-carbonitrile (D94)

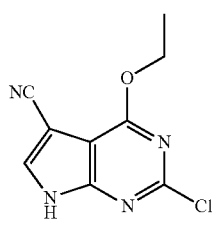

To a solution of 2-chloro-4-ethoxy-5-iodo-7H-pyrrolo-[2,3-d]-pyrimidine (which may be prepared according to D84) (610 mg, 1.886 mmol) in DMA (5 mL) was added copper(I) cyanide (507 mg, 5.66 mmol). The reaction mixture was irradiated by microwave at 120° C. for 2 hours. The mixture was diluted with ethyl acetate and water was added. The organic layer was washed with brine, dried over Na₂SO₄, filtered, and concentrated in vacuum. The crude was purified by column chromatography on silica gel (PE:EA=3:2) to give the title compound D94 (200 mg, 0.898 mmol, 47.6% yield) as a yellow solid.

LCMS: 223[M+H]⁺. $t_R$=2.777 (LCMS condition 1)

Description D95

2-chloro-4-ethoxy-5-(trifluoromethyl)-7H-pyrrolo-[2,3-d]-pyrimidine (D95)

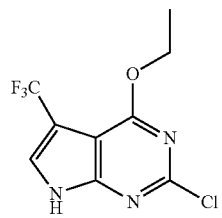 [SMILES: CCOc1nc(Cl)nc2[nH]cc(C(F)(F)F)c12]

Under a positive pressure of dry $N_2$, to a dried three-necked round-bottomed flask were added 2-chloro-4-ethoxy-7-tosyl-7H-pyrrolo-[2,3-d]-pyrimidine (which may be prepared according to D2)(800 mg, 1.675 mmol) and DMF (20 mL). Then copper (I) iodide (63.8 mg, 0.335 mmol) and methyl 2,2-difluoro-2-(fluorosulfonyl)acetate (643 mg, 3.35 mmol) were added. The reaction mixture was stirred at 80° C. for 1.5 hours. LCMS showed no reaction. Then, further copper (I) iodide (63.8 mg, 0.335 mmol) and methyl 2,2-difluoro-2-(fluorosulfonyl)-acetate (643 mg, 3.35 mmol) were added. The mixture was stirred at 100° C. for 2 hours. Then further copper (I) iodide (63.8 mg, 0.335 mmol) was added and the mixture was stirred at 100° C. for another 1.5 hours. The reaction was quenched by saturated $NH_4Cl$ solution. Then water (50 mL) was added to the mixture and extracted with EA (15 mL×3). The combined organic layer was washed with brine and dried over $Na_2SO_4$. After filtration and concentration, the residue was purified by column chromatography on silica gel (PE:EA=3:1) to give the title compound D95 (245.3 mg, 0.924 mmol, 55.1% yield) as a white solid.

LCMS: 266[M+H]$^+$. $t_R$=3.483 (LCMS condition 1)

$^1$H NMR (400 MHz, DMSO-d$_6$): δ 12.96 (br. s., 1H), 8.06 (s, 1H), 4.53 (q, J=7.1 Hz, 2H), 1.37 (t, 3H)

General Procedure 3 for Buchwald Reactions (D96-D121)

To a solution of 2-chloro-4-ethoxy-7-tosyl-7H-pyrrolo-[2,3-d]pyrimidine (which may be prepared according to D2) (1.0 eq), amines (1.0 eq) and xantphos (0.1 eq) in 1,4-dioxane (2.0 mL) and water (0.2 mL) was added potassium carbonate (2.0 eq) and PdCl$_2$(pddf) (0.1 eq). The reaction mixture was stirred overnight at 90° C. The reaction was quenched with water and extracted with EtOAc (20 mL×3). The combined organic layer was dried over $Na_2SO_4$, filtered and concentrated in vacuum. The crude was purified by column chromatography on silica gel (DCM:MeOH=25:1) to give the desired products D96-D121.

| | Structure/name | Starting material | [M + H] | Yield (%) |
|---|---|---|---|---|
| D96 | 4-((4-ethoxy-7-tosyl-7H-pyrrolo[2,3-d]pyrimidin-2-yl)amino)-N-(2-hydroxy-2-methylpropyl)-3-methoxybenzamide | D2 and D60 | 554 | 48 |
| D97 | (4-((4-ethoxy-7-tosyl-7H-pyrrolo[2,3-d]pyrimidin-2-yl)amino)phenyl)(4-methylpiperazin-1-yl)methanone | D2 and (4-aminophenyl)-(4-methylpiperazin-1-yl)-methanone | 535 | 75 |

-continued

| | Structure/name | Starting material | [M + H] | Yield (%) |
|---|---|---|---|---|
| D98 | (4-((4-ethoxy-7-tosyl-7H-pyrrolo[2,3-d]pyrimidin-2-yl)amino)-3-methoxyphenyl)(6-azaspiro[2.5]octan-6-yl)methanone | D2 and D61 | 576 | 42 |
| D99 | (4-((4-ethoxy-7-tosyl-7H-pyrrolo[2,3-d]pyrimidin-2-yl)amino)-3-methoxyphenyl)(oxazolidin-3-yl)methanone | D2 and D62 | 538 | 60 |
| D100 | (4-((4-ethoxy-7-tosyl-7H-pyrrolo[2,3-d]pyrimidin-2-yl)amino)-2-methoxyphenyl)(morpholino)methanone | D2 and D63 | 552 | 62 |
| D101 | (3-(dimethylamino)-4-((4-ethoxy-7-tosyl-7H-pyrrolo[2,3-d]pyrimidin-2-yl)amino)phenyl)(morpholino)methanone | D2 and D64 | 565 | 78 |

-continued

| | Structure/name | Starting material | [M + H] | Yield (%) |
|---|---|---|---|---|
| D102 | 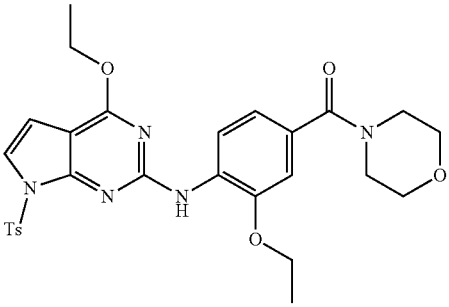<br>(3-ethoxy-4-((4-ethoxy-7-tosyl-7H-pyrrolo[2,3-d]pyrimidin-2-yl)amino)phenyl)(morpholino)methanone | D2 and D65 | 566 | 62 |
| D103 | 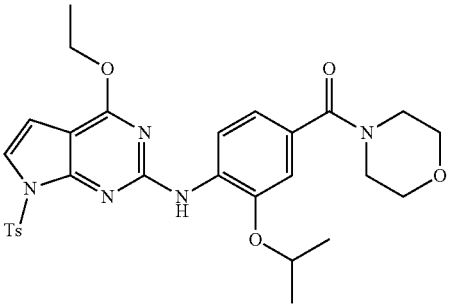<br>(4-((4-ethoxy-7-tosyl-7H-pyrrolo[2,3-d]pyrimidin-2-yl)amino)-3-isopropoxyphenyl)(morpholino)methanone | D2 and D66 | 580 | 40 |
| D104 | 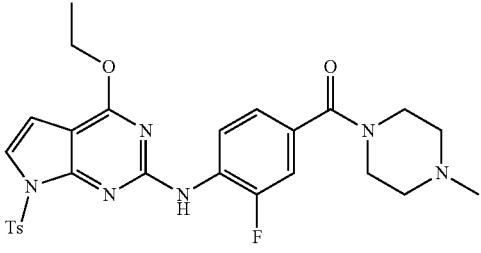<br>(4-((4-ethoxy-7-tosyl-7H-pyrrolo[2,3-d]pyrimidin-2-yl)amino)-3-fluorophenyl)(4-methylpiperazin-1-yl)methanone | D2 and D67 | 553 | 24 |
| D105 | 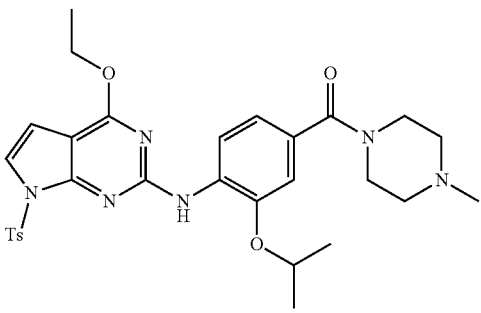<br>(4-((4-ethoxy-7-tosyl-7H-pyrrolo[2,3-d]pyrimidin-2-yl)amino)-3-isopropoxyphenyl)(4-methylpiperazin-1-yl)methanone | D2 and D68 | 593 | 44 |

-continued

| | Structure/name | Starting material | [M + H] | Yield (%) |
|---|---|---|---|---|
| D106 | 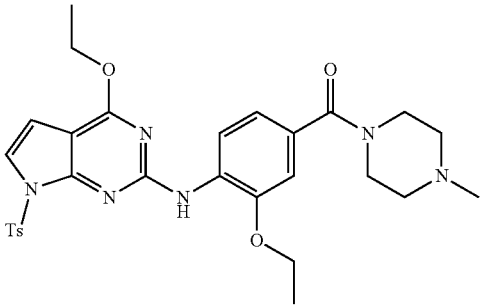<br>(3-ethoxy-4-((4-ethoxy-7-tosyl-7H-pyrrolo[2,3-d]pyrimidin-2-yl)amino)phenyl)(4-methylpiperazin-1-yl)methanone | D2 and D69 | 579 | 46 |
| D107 | 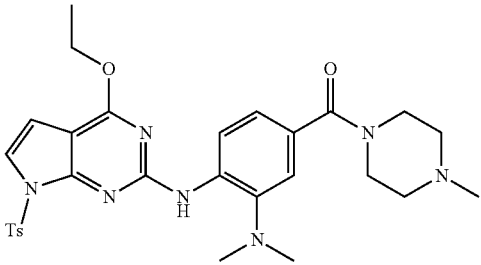<br>(3-(dimethylamino)-4-((4-ethoxy-7-tosyl-7H-pyrrolo[2,3-d]pyrimidin-2-yl)amino)phenyl)(4-methylpiperazin-1-yl)methanone | D2 and D70 | 578 | 49 |
| D108 | 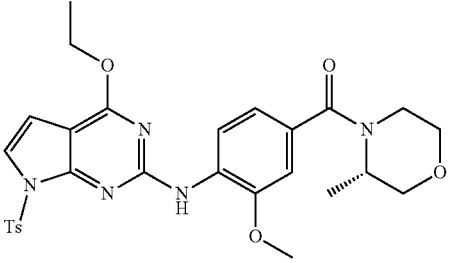<br>(S)-(4-((4-ethoxy-7-tosyl-7H-pyrrolo[2,3-d]pyrimidin-2-yl)amino)-3-methoxyphenyl)(3-methylmorpholino)methanone | D2 and D71 | 566 | 78 |
| D109 | 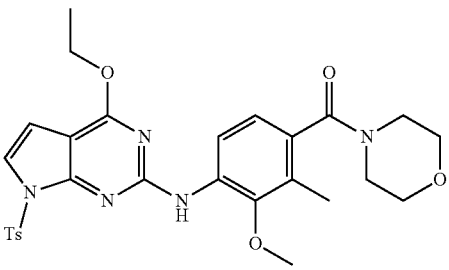<br>(4-((4-ethoxy-7-tosyl-7H-pyrrolo[2,3-d]pyrimidin-2-yl)amino)-3-methoxy-2-methylphenyl)(morpholino)methanone | D2 and D72 | 566 | 78 |

| | Structure/name | Starting material | [M + H] | Yield (%) |
|---|---|---|---|---|
| D110 | (R)-(3,4-dimethylpiperazin-1-yl)(4-((4-ethoxy-7-tosyl-7H-pyrrolo[2,3-d]pyrimidin-2-yl)amino)-3-methoxyphenyl)methanone | D2 and D73 | 579 | 41 |
| D111 | (R)-(4-((4-ethoxy-7-tosyl-7H-pyrrolo[2,3-d]pyrimidin-2-yl)amino)-3-methoxyphenyl)(3-methylmorpholino)methanone | D2 and D82 | 566 | 76 |
| D112 | (4-((4-ethoxy-5-methyl-7-tosyl-7H-pyrrolo[2,3-d]pyrimidin-2-yl)amino)-3-methoxyphenyl)(morpholino)methanone | (4-amino-3-methoxyphenyl)(morpholino)methanone and D86 | 566 | 84 |
| D113 | (4-((4-ethoxy-5-methyl-7-tosyl-7H-pyrrolo[2,3-d]pyrimidin-2-yl)amino)-3-methoxyphenyl)(4-methylpiperazin-1-yl)methanone | (4-amino-3-methoxyphenyl)(4-methylpiperazin-1-yl)methanone and D86 | 579 | 34 |

-continued

| | Structure/name | Starting material | [M + H] | Yield (%) |
|---|---|---|---|---|
| D114 | (S)-(2,4-dimethylpiperazin-1-yl)(4-((4-ethoxy-7-tosyl-7H-pyrrolo[2,3-d]pyrimidin-2-yl)amino)-3-methoxyphenyl)methanone | D2 and D75 | 579 | 18 |
| D115 | (2-chloro4-((4-ethoxy-7-tosyl-7H-pyrrolo[2,3-d]pyrimidin-2-yl)amino)-3-methoxyphenyl)(4-methylpiperazin-1-yl)methanone | D2 and D83 | 599 | 31 |
| D116 | (R)-(4-((4-ethoxy-7-tosyl-7H-pyrrolo[2,3-d]pyrimidin-2-yl)amino)-3-methoxyphenyl)(hexahydropyrrolo[1,2-a]pyrazin-2(1H)-yl)methanone | D2 and D76 | 591 | 74 |
| D117 | (R)-(2,4-dimethylpiperazin-1-yl)(4-((4-ethoxy-7-tosyl-7H-pyrrolo[2,3-d]pyrimidin-2-yl)amino)-3-methoxyphenyl)methanone | D2 and D77 | 579 | 23 |

| | Structure/name | Starting material | [M + H] | Yield (%) |
|---|---|---|---|---|
| D118 | (S)-(3,4-dimethylpiperazin-1-yl)(4-((4-ethoxy-7-tosyl-7H-pyrrolo[2,3-d]pyrimidin-2-yl)amino)-3-methoxyphenyl)methanone | D2 and D78 | 579 | 47 |
| D119 | (4-((4-ethoxy-7-tosyl-7H-pyrrolo[2,3-d]pyrimidin-2-yl)amino)-3-methoxyphenyl)(1-(methoxymethyl)-6-azaspiro[2.5]octan-6-yl)methanone | D2 and D79 | 619 | 66 |
| D120 | (R)-(4-((4-(cyclopropylmethoxy)-5-methyl-7-tosyl-7H-pyrrolo[2,3-d]pyrimidin-2-yl)amino)-3-methoxyphenyl)(2,4-dimethylpiperazin-1-yl)methanone | D90 and D77 | 619 | 67 |
| D121 | (4-((4-(cyclopropylmethoxy)-5-methyl-7-tosyl-7H-pyrrolo[2,3-d]pyrimidin-2-yl)amino)-3-methoxyphenyl)(4-methylpiperazin-1-yl)methanone | (4-amino-3-methoxyphenyl)(4-methylpiperazin-1-yl)methanone and D90 | 605 | 73 |

Description D122

(3-chloro-4-((4-ethoxy-7-tosyl-7H-pyrrolo-[2,3-d]-pyrimidin-2-yl)amino)phenyl)(4-methylpiperazin-1-yl)-methanone (D122)

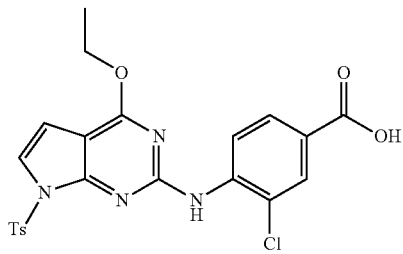 [SMILES: CCOc1nc(Nc2ccc(C(=O)O)cc2Cl)nc2c1ccn2S(=O)(=O)c1ccc(C)cc1]

To a solution of potassium carbonate (140 mg, 1.012 mmol), 2-chloro-4-ethoxy-7-tosyl-7H-pyrrolo[2,3-d]pyrimidine (which may be prepared according to D2) (178 mg, 0.506 mmol) and 4-amino-3-chlorobenzoic acid (104 mg, 0.607 mmol) in 1,4-dioxane (3 mL) and water (0.300 mL) stirred under nitrogen at room temperature was added PdCl$_2$(dppf)-CH$_2$Cl$_2$ adduct (41.3 mg, 0.051 mmol) and xantphos (36.2 mg, 0.076 mmol). The reaction vessel was sealed and heated in Biotage Initiator at 90° C. for 2 hours. After cooling, the crude product was purified by prep-HPLC to give the title product D122 (150 mg, 0.308 mmol, 60.9% yield) as a yellow solid.

LCMS: 487[M+H]$^+$. t$_R$=1.49. (LCMS condition 2)

Description D123

(3-chloro-4-((4-ethoxy-7-tosyl-7H-pyrrolo-[2,3-d]pyrimidin-2-yl)amino)phenyl)(4-methylpiperazin-1-yl)-methanone (D123)

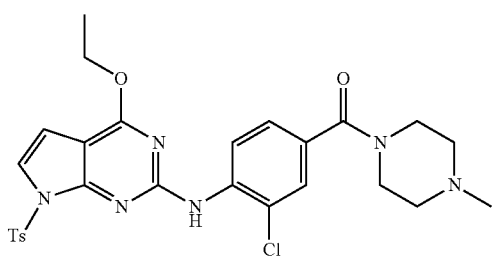 [SMILES: CCOc1nc(Nc2ccc(C(=O)N3CCN(C)CC3)cc2Cl)nc2c1ccn2S(=O)(=O)c1ccc(C)cc1]

To a solution of (3-chloro-4-((4-ethoxy-7-tosyl-7H-pyrrolo-[2,3-d]-pyrimidin-2-yl)amino)phenyl)(4-methylpiperazin-1-yl)-methanone (which may be prepared according to D122)(200 mg, 0.411 mmol), DIPEA (106 mg, 0.821 mmol) and 1-methylpiperazine (49.4 mg, 0.493 mmol) in THF (5 mL) was added HATU (187 mg, 0.493 mmol). The reaction mixture was stirred at room temperature for 3 hours. The mixture was directly purified with Biotage to give the title compound D123 (200 mg, 0.351 mmol, 86% yield) as a white solid.

LCMS: 570[M+H]$^+$. t$_R$=1.585. (LCMS condition 2)

Description D124

4-((4-ethoxy-7-tosyl-7H-pyrrolo-[2,3-d]pyrimidin-2-yl)amino)-3-methoxybenzoic acid (D124)

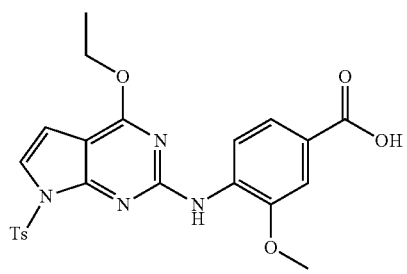 [SMILES: CCOc1nc(Nc2ccc(C(=O)O)cc2OC)nc2c1ccn2S(=O)(=O)c1ccc(C)cc1]

To a solution of 2-chloro-4-ethoxy-7-tosyl-7H-pyrrolo[2,3-d]pyrimidine (which may be prepared according to D2) (2.0 g, 5.68 mmol) and 4-amino-3-methoxybenzoic acid (1.140 g, 6.82 mmol) in 1,4-dioxane (1.5 mL) and water (0.2 mL) was added xantphos (0.493 g, 0.853 mmol), K$_2$CO$_3$ (2.357 g, 17.05 mmol) and PdCl$_2$(dppf)-CH$_2$Cl$_2$ adduct (0.464 g, 0.568 mmol). The mixture was stirred overnight at 90° C. The reaction was quenched with water and extracted with DCM (20 mL×3). The combined organic layer was dried over Na$_2$SO$_4$, filtered and concentrated in vacuum. The crude was purified by column chromatography on silica gel (DCM:CH$_3$OH=20:1) to give the title compound D124 (2.60 g, 5.39 mmol, 95% yield) as a yellow solid.

LCMS: 483[M+H]$^+$. t$_R$=1.13. (LCMS condition 2)

$^1$H NMR (400 MHz, DMSO-d$_6$): δ 12.74 (s, 1H), 8.64 (d, J=10.0 Hz, 1H), 8.11 (s, 1H), 7.69 (m, 2H), 7.69 (d, J=12.0 Hz, 1H), 7.53 (m, 3H), 7.38 (m, 2H), 6.66 (d, J=5.0 Hz, 1H), 4.49 (dd, J=9.0 Hz, 2H), 3.95 (s, 3H), 2.31 (s, 3H), 1.35 (t, J=9.0 Hz, 3H).

General Procedure 4 for the Amide Coupling Reactions (D125-D129)

To a solution of 4-((4-ethoxy-7-tosyl-7H-pyrrolo-[2,3-d]pyrimidin-2-yl)amino)-3-methoxybenzoic acid (which may be prepared according to D124) (1 eq), HATU (1 eq) and DIPEA (2 eq) in DMF (3 mL) was added amines (2 eq). The mixture was stirred overnight at room temperature. The mixture was diluted with EA, washed with water. The organic layer was dried and concentrated. The crude product was purified via chromatography on silica gel (DCM:CH$_3$OH=20:1) to give the desired products D125-D129.

|  | Structure/name | Amine (starting material) | [M + H]+ | Yield (%) |
|---|---|---|---|---|
| D125 | (R)-(4-((4-ethoxy-7-tosyl-7H-pyrrolo[2,3-d]pyrimidin-2-yl)amino)-3-methoxyphenyl)(2-(methoxymethyl)pyrrolidin-1-yl)methanone | (R)-2-(methoxymethyl) pyrrolidine | 580 | 72 |
| D126 | (S)-(4-((4-ethoxy-7-tosyl-7H-pyrrolo[2,3-d]pyrimidin-2-yl)amino)-3-methoxyphenyl)(2-(methoxymethyl)pyrrolidin-1-yl)methanone | (S)-2-(methoxymethyl) pyrrolidine | 580 | 59 |
| D127 | (4-((4-ethoxy-7-tosyl-7H-pyrrolo[2,3-d]pyrimidin-2-yl)amino)-3-methoxyphenyl)(4-(methoxymethyl)piperidin-1-yl)methanone | 4-(methoxymethyl) piperidine | 594 | 69 |
| D128 | (4-((4-ethoxy-7-tosyl-7H-pyrrolo[2,3-d]pyrimidin-2-yl)amino)-3-methoxyphenyl)(1-(hydroxymethyl)-3-azabicyclo[3.1.0]hexan-3-yl)methanone | D47 | 578 | 80 |

-continued

| Structure/name | Amine (starting material) | [M + H]+ | Yield (%) |
|---|---|---|---|
| D129 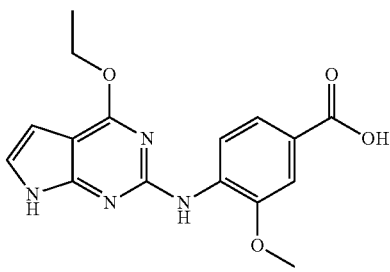 [SMILES: CCOc1nc(Nc2ccc(C(=O)O)cc2OC)nc2[nH]ccc12] (4-((4-ethoxy-7-tosyl-7H-pyrrolo[2,3-d]pyrimidin-2-yl)amino)-3-methoxyphenyl)(2-oxa-6-azaspiro[3.5]nonan-6-yl)methanone | 2-oxa-6-azaspiro[3.5]nonane | 591 | 45 |

Description D130

4-((4-ethoxy-7H-pyrrolo-[2,3-d]-pyrimidin-2-yl)amino)-3-methoxybenzoic acid (D129)

To a solution of 4-((4-ethoxy-7-tosyl-7H-pyrrolo-[2, 3-d]pyrimidin-2-yl)amino)-3-methoxybenzoic acid (which may be prepared according to D124) (250 mg, 0.518 mmol) in isopropanol (3.0 mL) was added sodium hydroxide (0.518 mL, 1.036 mmol). The reaction mixture was stirred overnight at 60° C. 2N HCl was added to until pH=3. The mixture was extracted with EtOAc (20 mL×2). The combined organic layers were dried over Na$_2$SO$_4$ and concentrated in vacuum. The crude was purified by chromatography on silica gel (DCM:MeOH=15:1) to give the title compound E130 (166 mg, 0.506 mmol, 98% yield) as a yellow solid.

LCMS: 329[M+H]+. t$_R$=1.089. (LCMS condition 2)

Description D131 tert-butyl-7-(4-((4-ethoxy-7H-pyrrolo-[2,3-d]-pyrimidin-2-yl)amino)-3-methoxybenzoyl)-2,7-diazaspiro-[3.5]-nonane-2-carboxylate (D131)

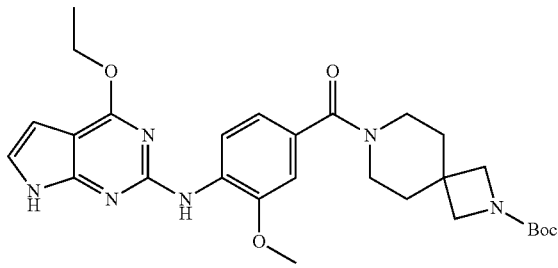 [SMILES: CCOc1nc(Nc2ccc(C(=O)N3CCC4(CC3)CN(C(=O)OC(C)(C)C)C4)cc2OC)nc2[nH]ccc12]

A solution of 2-chloro-4-ethoxy-7H-pyrrolo-[2,3-d]-pyrimidine (which may be prepared according to D1) (80 mg, 0.405 mmol), tert-butyl 7-(4-amino-3-methoxybenzoyl)-2,7-diazaspiro[3.5]nonane-2-carboxylate (which may be prepared according to D58) (167 mg, 0.445 mmol), dicyclohexyl(2',4',6'-triisopropyl-[1,1'-biphenyl]-2-yl)phosphine (20.07 mg, 0.042 mmol), Pd$_2$(dba)$_3$ (18.53 mg, 0.020 mmol) and potassium carbonate (168 mg, 1.214 mmol) in 2-butanol (6 mL) was stirred at 120° C. under microwave for 45 min. The mixture was filtrated with Celite and the solution was concentrated. The crude was purified via MDAP (base mobile phase) to give the title compound D131 (142 mg, 0.265 mmol, 65.4% yield) as a yellow solid.

LCMS: 564[M+H]+. t$_R$=3.637. (LCMS condition 1)

Description D132

(1-(hydroxymethyl)-3-azabicyclo-[3.1.0]-hexan-3-yl)(3-methoxy-4-nitro-phenyl)-methanone (D132)

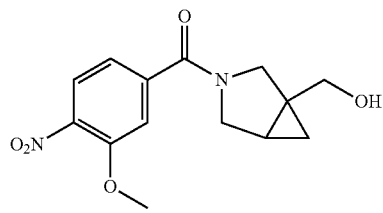 [SMILES: COc1cc(C(=O)N2CC3CC3(CO)C2)ccc1[N+](=O)[O-]]

To a solution of 3-methoxy-4-nitrobenzoic acid (523 mg, 2.65 mmol), HATU (1210 mg, 3.18 mmol) and DIPEA (0.708 mL, 3.98 mmol) in DMF (5 mL) was added (±)-3-azabicyclo-[3.1.0]-hexan-1-ylmethanol, trifluoroacetic acid salt (which may be prepared according to D47) (0.097 mL, 2.65 mmol). The mixture was stirred overnight at room temperature. The mixture was diluted with EA, washed with water. The organic layer was dried and concentrated. The crude was purified via chromatography on silica gel (DCM: CH$_3$OH=14:1) to give the title compound D132 (487.6 mg, 1.568 mmol, 59.1% yield) as yellow oil.

LCMS: 293[M+H]+. t$_R$=2.139. (LCMS condition 1)
$^1$H NMR (400 MHz, DMSO-d$_6$): δ 7.96 (s, 1H), 7.39 (d, J=2.0 Hz, 1H), 7.08-7.19 (m, 1H), 4.56-4.80 (m, 1H), 3.84-3.98 (m, 4H), 3.37-3.72 (m, 4H), 1.37-1.54 (m, 1H), 0.68-0.81 (m, 1H), 0.27-0.44 (m, 1H).

Description D133

(3-methoxy-4-nitrophenyl)(1-(methoxymethyl)-3-azabicyclo-[3.1.0]-hexan-3-yl)methanone (D133)

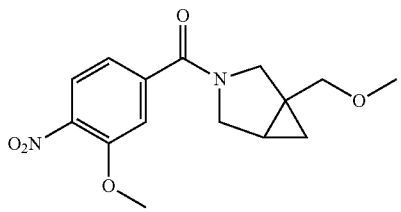

To a solution of (1-(hydroxymethyl)-3-azabicyclo-[3.1.0]-hexan-3-yl)(3-methoxy-4-nitro-phenyl)-methanone (which may be prepared according to D132) (483 mg, 1.652 mmol) in THF (10 mL) was added NaH (99 mg, 2.479 mmol). After stirring for 30 min, iodomethane (0.310 mL, 4.96 mmol) was then added. The mixture was then stirred at room temperature for 3 hours. Methanol was added and the solvent was evaporated. The crude was diluted with EA, washed with water. The organic layer was concentrated and purified via chromatography on silica gel (DCM:CH$_3$OH=14:1) to give the title compound D133 (340 mg, 0.877 mmol, 53.1% yield) as yellow oil.

LCMS: 307 [M+H]$^+$. t$_R$=2.662. (LCMS condition 1)

$^1$H NMR (400 MHz, DMSO-d$_6$): δ 7.92 (dd, J=4.0, 8.2 Hz, 1H), 7.39 (s, 1H), 7.15 (d, J=8.1 Hz, 1H), 4.10 (q, J=5.2 Hz, 1H), 3.95 (s, 3H), 3.84-3.92 (m, 1H), 3.58-3.75 (m, 1H), 3.40-3.50 (m, 2H), 3.25 (d, J=12.0 Hz, 1H), 3.17 (d, 3H), 1.40-1.59 (m, 1H), 0.71-0.81 (m, 1H), 0.39-0.52 (m, 1H).

Description D134

(4-amino-3-methoxyphenyl)(1-(methoxymethyl)-3-azabicyclo-[3.1.0]hexan-3-yl)methanone (D134)

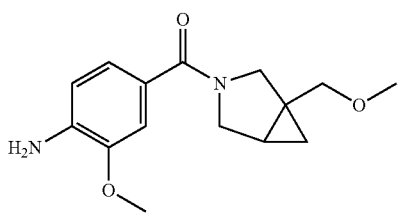 [SMILES: COCC12CC1CN(C(=O)c1ccc([N+](=O)[O-])c(OC)c1)C2]

A solution of (3-methoxy-4-nitrophenyl)(1-(methoxymethyl)-3-azabicyclo-[3.1.0]-hexan-3-yl)methanone (which may be prepared according to D133) (340 mg, 0.877 mmol), iron (147 mg, 2.63 mmol) in acetic acid (2 mL) was stirred at 70° C. for 2 hours. The reaction was dissolved in EA (10 mL) and filtrated. The solution was then extracted with saturated NaHCO$_3$ solution and brine. The organic phase was dried over Na$_2$SO$_4$ and concentrated to give the title compound D134 (240 mg, 0.521 mmol, 59.4% yield) as yellow oil.

LCMS: 277 [M+H]$^+$. t$_R$=1.752. (LCMS condition 1)

$^1$H NMR (400 MHz, DMSO-d$_6$): δ 6.83-6.93 (m, 2H), 6.59 (d, J=8.1 Hz, 1H), 5.15 (s, 1H), 3.83-3.98 (m, 1H), 3.77 (s, 3H), 3.45-3.54 (m, 2H), 3.39 (m, 1H), 3.13-3.28 (m, 5H), 0.72 (dd, J=4.9, 7.6 Hz, 1H), 0.28 (t, J=4.4 Hz, 1H).

Description D135

(1 S,3S,5S)-tert-butyl 3-cyano-2-azabicyclo-[3.1.0]-hexane-2-carboxylate (D135)

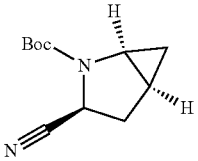 [SMILES: CC(C)(C)OC(=O)N1[C@H](C#N)C[C@@H]2C[C@@H]21]

To a solution of (1 S,3S,5S)-tert-butyl 3-carbamoyl-2-azabicyclo[3.1.0]hexane-2-carboxylate (1.6 g, 7.07 mmol) in anhydrous pyridine (20 mL) under −20° C. was added TFAA (4.00 mL, 28.3 mmol) dropwise. The mixture was then stirred at −20° C. for about 1 hour and warmed to room temperature for further 8 hours. Water was added and the mixture was stirred for 30 minutes. Then the mixture was extracted with ethyl acetate and the organic layer was washed with 1M HCl solution, water and brine, dried over Na$_2$SO$_4$ and concentrated to give the title compound D136 (1.473 g, 7.07 mmol, 100% yield) as yellow oil.

LCMS: 209 [M+H]$^+$. t$_R$=2.817. (LCMS condition 1)

Description D136

(1 S,3S,5S)-2-azabicyclo-[3.1.0]-hexane-3-carbonitrile (D136)

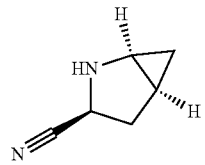

A solution of (1 S,3S,5S)-tert-butyl 3-cyano-2-azabicyclo-[3.1.0]-hexane-2-carboxylate (which may be prepared according to D135) (1.473 g, 7.07 mmol) and 1M hydrochloric acid in diethyl ether (14.15 ml, 14.15 mmol) was stirred overnight at room temperature. Precipitate was formed, and then the solvent was removed under reduced pressure. The residue was re-dissolved in dry diethyl ether, and then filtered. The solid was washed with dry diethyl ether, dried over under vacuum to give the title compound D136 (620 mg, 4.29 mmol, 60.6% yield) as a white solid.

$^1$H NMR (400 MHz, DMSO-d$_6$): δ 5.02 (dd, J=2.2, 9.8 Hz, 1H), 3.42 (td, J=2.8, 6.1 Hz, 1H), 2.58-2.53 (m, 0H), 2.30 (dd, J=2.1, 13.8 Hz, 1H), 1.82-1.97 (m, 1H), 0.88-1.06 (m, 2H).

Description D137

(4-((4-ethoxy-7-tosyl-7H-pyrrolo-[2,3-d]-pyrimidin-2-yl)amino)-3-methoxyphenyl)(4-methylpiperazin-1-yl)-methanone (D137)

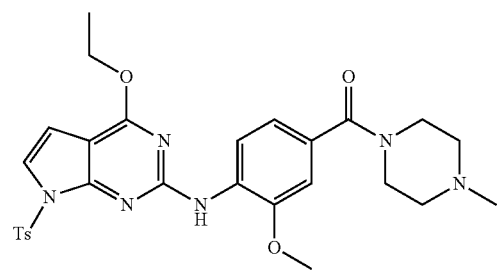 [SMILES: CCOc1nc(Nc2ccc(C(=O)N3CCN(C)CC3)cc2OC)nc2c1ccn2S(=O)(=O)c1ccc(C)cc1]

To a solution of 2-chloro-4-ethoxy-7-tosyl-7H-pyrrolo-[2,3-d]-pyrimidine (which may be prepared according to D2) (200 mg, 0.568 mmol), potassium carbonate (157 mg, 1.137 mmol), (9,9-dimethyl-9H-xanthene-4,5-diyl)bis(diphenylphosphine) (49.3 mg, 0.085 mmol), and PdCl$_2$(dppf)-CH$_2$Cl$_2$ adduct (46.4 mg, 0.057 mmol) in 1,4-dioxane (0.8 mL) and water (0.2 mL) under nitrogen was added (4-amino-3-methoxyphenyl)(4-methylpiperazin-1-yl)methanone (170 mg, 0.682 mmol). The reaction mixture was stirred overnight at 90° C. The reaction mixture was partitioned between ethyl acetate (25 mL) and water (10 mL). The organic phase was washed with water, NaHCO$_3$ solution and brine, dried over Na$_2$SO$_4$ and evaporated in vacuum to give the title compound D137 (100 mg, 0.131 mmol, 23.05% yield) as a yellow oil.

LCMS: 565 [M+H]$^+$. $t_R$=1.482 mins. (LCMS condition 1)

General Procedure 5 for Buchwald Reaction

To a tube was added 2-chloro-4-ethoxy-7H-pyrrolo-[2,3-d]pyrimidine D1 (1.0 eq), amines (1.2 eq) and Xphos (0.1 eq), 2-butanol (3.0 mL), Pd$_2$(dba)$_3$ (0.05 eq) and K$_2$CO$_3$ (3 eq). The tube was sealed, and bobbled with nitrogen for 2 min. The reaction mixture was stirred with under microwave at 120° C. for 45 min. After cooling, the mixture was filtered, concentrated, and purified by MDAP (base mobile phase) to give the title products.

Example 1

(4-((4-ethoxy-7H-pyrrolo-[2,3-d]-pyrimidin-2-yl)amino)-3-methoxyphenyl)(morpholino)methanone (E1)

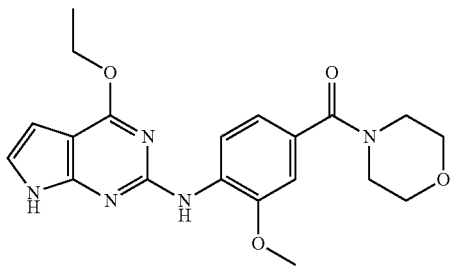 [SMILES: CCOc1nc(Nc2ccc(C(=O)N3CCOCC3)cc2OC)nc2[nH]ccc12]

The title compound E1 was prepared according to the general procedures 5 for Buchwald reaction starting from 2-chloro-4-ethoxy-7H-pyrrolo-[2,3-d]pyrimidine (which can be prepared according to D1) and (4-amino-3-methoxyphenyl)(morpholino)methadone (which can be prepared following procedures described in PCT Int. Appl., WO2012097682) as 810 mg of an off-white solid. Yield: 35.4%.

LCMS: 398 [M+H]$^+$. $t_R$=3.420 mins. (LCMS condition 1)
$^1$H NMR (400 MHz, DMSO-d$_6$): δ 8.62 (d, J=8.0 Hz, 1H), 7.63 (s, 1H), 6.93-7.15 (m, 3H), 6.34 (d, J=3.5 Hz, 1H), 4.52 (q, J=7.0 Hz, 2H), 3.94 (s, 3H), 3.45-3.70 (m, 8H), 1.41 (t, J=7.0 Hz, 3H).

Example 2

(4-((4-ethoxy-7H-pyrrolo-[2,3-d]-pyrimidin-2-yl)amino)-2-fluoro-5-methoxyphenyl)(morpholino)methanone (E2)

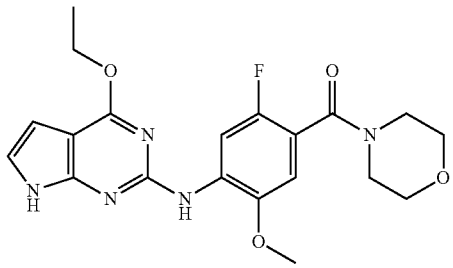 [SMILES: CCOc1nc(Nc2cc(F)c(C(=O)N3CCOCC3)cc2OC)nc2[nH]ccc12]

The title compound E2 was prepared according to the general procedures 5 for Buchwald reaction starting from 2-chloro-4-ethoxy-7H-pyrrolo-[2,3-d]pyrimidine (which can be prepared according to D1) and (4-amino-2-fluoro-5-methoxyphenyl)(morpholino)methanone (which can be prepared following the procedures described in Journal of Medicinal Chemistry, 55(22), 9416-9433; 2012) as 125 mg of an off-white solid. Yield: 47.1%.

LCMS: 416 [M+H]$^+$. $t_R$=2.999 mins. (LCMS condition 1)
$^1$H NMR (400 MHz, DMSO-d$_6$): δ 11.50-11.83 (m, 1H), 8.59 (d, J=12.5 Hz, 1H), 7.72 (s, 1H), 7.10 (br. s., 1H), 7.01 (d, J=6.1 Hz, 1H), 6.36 (br. s., 1H), 4.52 (q, J=7.1 Hz, 2H), 3.93 (s, 3H), 3.50-3.70 (m, 6H), 3.37-3.43 (m, 2H), 1.41 (t, J=7.0 Hz, 3H).

Example 3

(4-((4-ethoxy-7H-pyrrolo-[2,3-d]-pyrimidin-2-yl)amino)-3-methoxyphenyl)(4-methylpiperazin-1-yl)-methanone (E3)

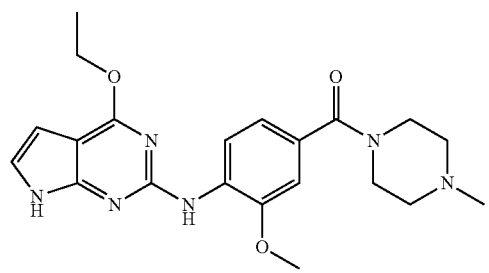 [SMILES: CCOc1nc(Nc2ccc(C(=O)N3CCN(C)CC3)cc2OC)nc2[nH]ccc12]

A solution of (4-((4-ethoxy-7-tosyl-7H-pyrrolo-[2,3-d]-pyrimidin-2-yl)amino)-3-methoxyphenyl)(4-methylpiperazin-1-yl)-methanone (which can be prepared according to D137) (100 mg, 0.177 mmol) and sodium hydroxide (2 mL, 4.00 mmol, 2M in water) in isopropanol (5 mL) was stirred overnight at 60° C. The mixture was evaporated and 2N HCl was added until pH=7. The mixture was extracted with EA. The organic layer was dried with MgSO$_4$ and evaporated. The residue was purified by prep-HPLC to give the title compound E3 (25 mg, 0.061 mmol, 34.4% yield) as a white solid.

LCMS: 411 [M+H]$^+$. $t_R$=1.259. (LCMS condition 2)

¹H NMR (400 MHz, DMSO-d₆): δ 11.58 (br. s., 1H), 8.60 (d, J=8.3 Hz, 1H), 7.63 (s, 1H), 6.93-7.13 (m, 3H), 6.33 (br. s., 1H), 4.51 (d, J=7.0 Hz, 2H), 3.93 (s, 3H), 3.52 (br. s., 4H), 2.33 (br. s., 4H), 2.20 (s, 3H), 1.40 (t, J=6.9 Hz, 3H).

Example 4

(4-((4-ethoxy-7H-pyrrolo-[2,3-d]pyrimidin-2-yl)amino)-3-methoxyphenyl)(4-(4-methylpiperazin-1-yl)-piperidin-1-yl)-methanone (E4)

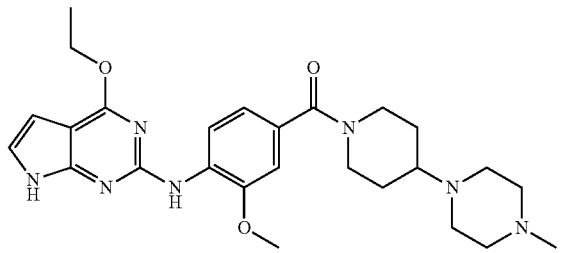 [SMILES: CCOc1nc(Nc2ccc(C(=O)N3CCC(N4CCN(C)CC4)CC3)cc2OC)nc2[nH]ccc12]

The title compound E4 was prepared according to the general procedure 5 for Buchwald reaction starting from 2-chloro-4-ethoxy-7H-pyrrolo-[2,3-d]pyrimidine (which can be prepared according to D1) and (4-amino-3-methoxyphenyl)(4-(4-methylpiperazin-1-yl)piperidin-1-yl)methanone (which can be prepared according to D52) as 16 mg of a white solid. Yield: 8.01%.

LCMS: 494[M+H]⁺. $t_R$=2.139. (LCMS condition 1)

¹H NMR (400 MHz, CHLOROFORM-d): δ 8.62-8.70 (m, 1H), 8.27-8.38 (m, 1H), 7.59-7.65 (m, 1H), 6.97-7.07 (m, 2H), 6.88 (dd, J=2.2, 3.4 Hz, 1H), 6.46 (dd, J=2.2, 3.4 Hz, 1H), 4.58 (q, J=7.1 Hz, 2H), 3.95 (s, 3H), 2.77-3.05 (m, 2H), 2.56-2.72 (m, 4H), 2.39-2.54 (m, 4H), 2.29 (s, 3H), 1.78-2.00 (m, 2H), 1.46-1.51 (m, 3H).

Example 5

(4-((4-ethoxy-7H-pyrrol-[2,3-d]pyrimidin-2-yl)amino)-2-fluoro-5-methoxyphenyl)(4-methylpiperazin-1-yl)-methanone (E5)

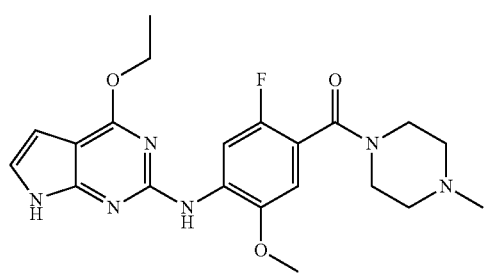 [SMILES: CCOc1nc(Nc2cc(F)c(C(=O)N3CCN(C)CC3)cc2OC)nc2[nH]ccc12]

The title compound E5 was prepared according to the general procedure 5 for Buchwald reaction starting from 2-chloro-4-ethoxy-7H-pyrrolo-[2,3-d]pyrimidine (which can be prepared according to D1) and (4-amino-2-fluoro-5-methoxyphenyl)(4-methylpiperazin-1-yl)methanone (which can be prepared according to D53) as 39 mg of a white solid. Yield: 3.95%.

LCMS: 429[M+H]⁺. $t_R$=1.148. (LCMS condition 1)

¹H NMR (400 MHz, DMSO-d₆): δ 11.68 (br. s., 1H), 8.57 (d, J=12.5 Hz, 1H), 7.71 (s, 1H), 7.09 (br. s., 1H), 6.97 (d, J=6.0 Hz, 1H), 6.36 (br. s., 1H), 4.52 (q, J=7.0 Hz, 2H), 3.92 (s, 3H), 3.63 (br. s., 2H), 3.29-3.31 (m, 2H), 2.23-2.41 (m, 4H), 2.20 (s, 3H), 1.40 (t, 3H).

Example 6

(S)-(4-((4-ethoxy-7H-pyrrolo-[2,3-d]-pyrimidin-2-yl)amino)-3-methoxyphenyl)(hexahydropyrrolo-[1,2-a]-pyrazin-2(1H)-yl)methanone (E6)

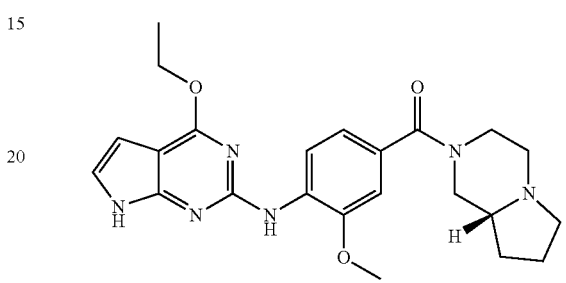

The title compound E6 was prepared according to the general procedure 5 for Buchwald reaction starting from 2-chloro-4-ethoxy-7H-pyrrolo-[2,3-d]pyrimidine (which can be prepared according to D1) and (S)-(4-amino-3-methoxyphenyl)(hexahydropyrrolo[1,2-a]pyrazin-2(1H)-yl)methanone (which can be prepared according to D54) as 39 mg of a white solid. Yield: 25.2%.

LCMS: 437[M+H]⁺. $t_R$=2.301. (LCMS condition 1)

¹H NMR (400 MHz, CHLOROFORM-d): δ 8.66 (d, J=8.8 Hz, 1H), 8.49-8.60 (m, 1H), 7.67-7.57 (m, 1H), 7.04 (s, 2H), 6.86 (dd, J=2.2, 3.4 Hz, 1H), 6.46 (dd, J=2.2, 3.4 Hz, 1H), 4.58 (q, J=7.1 Hz, 2H), 3.95 (s, 3H), 3.12 (t, J=8.3 Hz, 3H), 2.18 (d, J=9.0 Hz, 2H), 2.04-1.59 (m, 7H), 1.49 (t, J=7.1 Hz, 3H), 1.31-1.45 (m, 1H).

Example 7

(3-(difluoromethoxy)-4-((4-ethoxy-7H-pyrrolo-[2,3-d]-pyrimidin-2-yl)amino)phenyl)(4-methylpiperazin-1-yl)-methanone (E7)

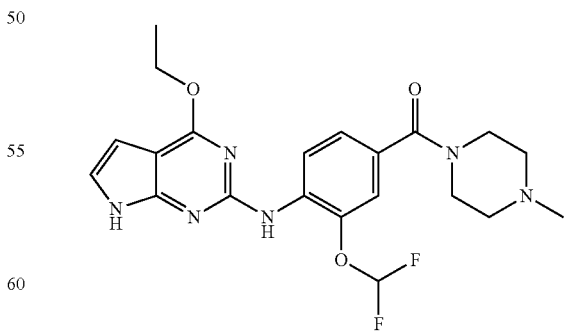

The title compound E7 was prepared according to the general procedures 5 for Buchwald reaction starting from 2-chloro-4-ethoxy-7H-pyrrolo-[2,3-d]pyrimidine (which can be prepared according to D1) and (4-amino-3-(difluoromethoxy)-phenyl)(4-methylpiperazin-1-yl)-methanone (which can be prepared according to D80) as 41 mg of a white solid. Yield: 30.2%.

LCMS: 447[M+H]+. $t_R$=2.519. (LCMS condition 1)

$^1$H NMR (400 MHz, METHANOL-d$_4$): δ 8.74 (d, J=8.3 Hz, 1H), 7.16-7.27 (m, 2H), 6.63-7.07 (m, 2H), 6.29 (d, J=3.4 Hz, 1H), 4.43-4.50 (m, 2H), 3.47-3.71 (m, 4H), 2.40 (br. s., 4H), 2.24 (s, 3H), 1.37 (t, 3H).

Example 8

(3-(cyclopropylmethoxy)-4-((4-ethoxy-7H-pyrrolo-[2,3-d]-pyrimidin-2-yl)amino)phenyl)(4-methylpiperazin-1-yl)-methanone (E8)

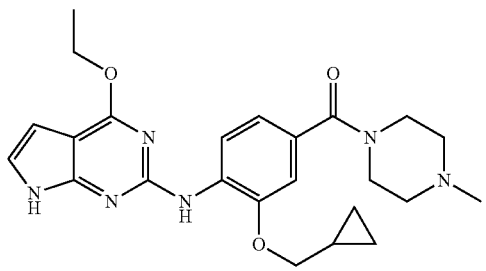 [SMILES: CCOc1nc(Nc2ccc(C(=O)N3CCN(C)CC3)cc2OCC2CC2)nc2[nH]ccc12]

The title compound E8 was prepared according to the general procedures 5 for Buchwald reaction starting from 2-chloro-4-ethoxy-7H-pyrrolo-[2,3-d]pyrimidine (which can be prepared according to D1) and (4-amino-3-(cyclopropylmethoxy)-phenyl)(4-methylpiperazin-1-yl)-methanone (which can be prepared according to D81) as 41 mg of a white solid. Yield: 22.48%.

LCMS: 451[M+H]+. $t_R$=2.710. (LCMS condition 1)

$^1$H NMR (400 MHz, METHANOL-d$_4$): δ 8.65 (d, J=8.1 Hz, 1H), 6.90-7.00 (m, 2H), 6.85 (d, J=3.7 Hz, 1H), 6.28 (d, J=3.4 Hz, 1H), 4.48 (q, J=7.1 Hz, 2H), 3.89 (d, J=7.1 Hz, 2H), 3.59 (br. s., 4H), 2.39 (br. s., 4H), 2.24 (s, 3H), 1.39 (t, J=7.1 Hz, 3H), 1.27-1.34 (m, 1H), 0.60 (q, 2H), 0.30-0.37 (m, 2H).

Example 9

(4-((4-ethoxy-7H-pyrrolo-[2,3-d]pyrimidin-2-yl)amino)phenyl)(morpholino)methanone (E9)

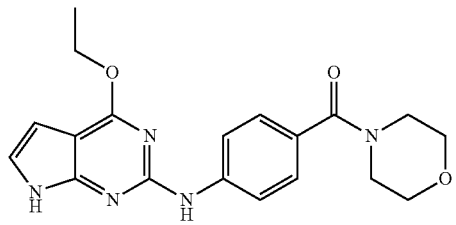 [SMILES: CCOc1nc(Nc2ccc(C(=O)N3CCOCC3)cc2)nc2[nH]ccc12]

The title compound E9 was prepared according to the general procedures 5 for Buchwald reaction starting from 2-chloro-4-ethoxy-7H-pyrrolo-[2,3-d]pyrimidine (which can be prepared according to D1) and (4-aminophenyl)(morpholino)-methanone (which can be prepared following procedures described in PCT Int. Appl., WO2008018426) as 52 mg of a white solid. Yield: 20.44%.

LCMS: 368[M+H]+. $t_R$=2.511. (LCMS condition 1)

$^1$H NMR (400 MHz, DMSO-d$_6$): δ 9.33 (s, 1H), 7.92 (d, J=8.3 Hz, 2H), 7.35 (d, J=8.3 Hz, 2H), 7.02 (d, J=3.4 Hz, 1H), 6.32 (d, J=3.2 Hz, 1H), 4.55 (q, J=7.1 Hz, 2H), 3.61 (br. s., 4H), 3.52 (br. s., 4H), 1.42 (t, J=7.1 Hz, 3H).

Example 10

(4-((4-ethoxy-7H-pyrrolo-[2,3-d]-pyrimidin-2-yl)amino)-3-methoxyphenyl)(2-oxa-6-azaspiro-[3.3]heptan-6-yl)methanone (E10)

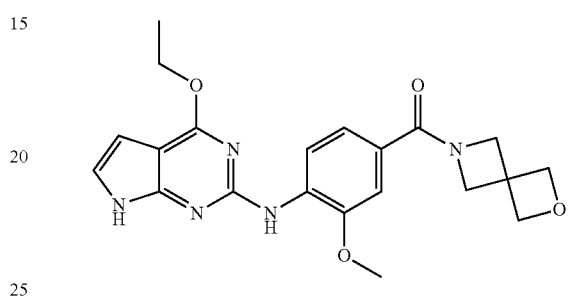

The title compound E10 was prepared according to the general procedures 5 for Buchwald reaction starting from 2-chloro-4-ethoxy-7H-pyrrolo-[2,3-d]pyrimidine (which can be prepared according to D1) and (4-amino-3-methoxyphenyl)(2-oxa-6-azaspiro[3.3]heptan-6-yl)methanone (which can be prepared according to D55) as 20.4 mg of a white solid. Yield: 15.75%.

LCMS: 410[M+H]+. $t_R$=2.38. (LCMS condition 1)

$^1$H NMR (400 MHz, DMSO-d$_6$): δ 11.63 (br. s., 1H), 8.65 (d, J=8.3 Hz, 1H), 7.69 (s, 1H), 7.21-7.28 (m, 2H), 6.98-7.11 (m, 1H), 6.35 (dd, J=3.2, 2.0 Hz, 1H), 4.67-4.73 (m, 4H), 4.52 (q, J=7.1 Hz, 4H), 4.13-4.27 (m, 2H), 3.95 (s, 3H), 1.36-1.46 (m, 3H).

Example 11

((2R,6S)-2,6-dimethyl morpholino)(4-((4-ethoxy-7H-pyrrolo[2,3-d]pyrimidin-2-yl)amino)-3-methoxyphenyl)methanone (E11)

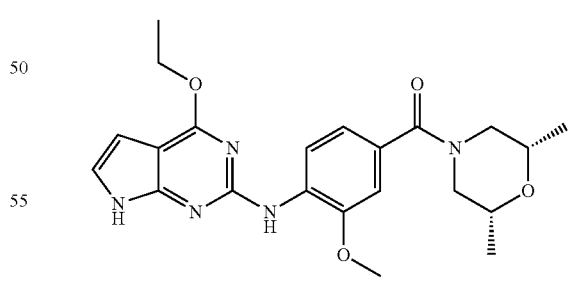

The title compound E11 was prepared according to the general procedures 5 for Buchwald reaction starting from 2-chloro-4-ethoxy-7H-pyrrolo-[2,3-d]pyrimidine (which can be prepared according to D1) and (4-amino-3-methoxyphenyl)((2R,6S)-2,6-dimethylmorpholino)methanone (which can be prepared according to D56) as 49 mg of a white solid. Yield: 18.97%.

LCMS: 426[M+H]+. $t_R$=3.025. (LCMS condition 1)

¹H NMR (400 MHz, CHLOROFORM-d): δ 8.62-8.72 (m, 1H), 8.41-8.55 (m, 1H), 7.57-7.70 (m, 1H), 6.97-7.07 (m, 2H), 6.90-6.80 (m, 1H), 6.40-6.53 (m, 1H), 4.58 (q, J=6.9 Hz, 2H), 3.96 (s, 3H), 3.47-3.71 (m, 2H), 2.39-2.96 (m, 2H), 1.61-1.64 (m, 2H), 1.49 (t, J=7.1 Hz, 3H), 0.97-1.35 (m, 6H).

Example 12

(4-((4-ethoxy-7H-pyrrolo-[2,3-d]pyrimidin-2-yl)amino)-3-methoxyphenyl)(2-oxa-6-azaspiro-[3.4]-octan-6-yl)-methanone (E12)

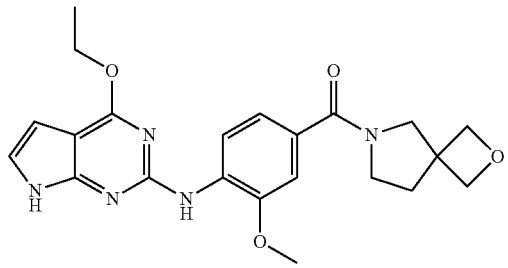 [SMILES: CCOc1nc(Nc2ccc(C(=O)N3CCC4(COC4)C3)cc2OC)nc2[nH]ccc12]

The title compound E12 was prepared according to the general procedures 5 for Buchwald reaction starting from 2-chloro-4-ethoxy-7H-pyrrolo-[2,3-d]pyrimidine (which can be prepared according to D1) and (4-amino-3-methoxyphenyl)(2-oxa-6-azaspiro[3.4]octan-6-yl)methanone (which can be prepared according to D57) as 15.3 mg of a white solid. Yield: 11.33%.

LCMS: 424[M+H]⁺. $t_R$=2.38. (LCMS condition 1)
¹H NMR (400 MHz, DMSO-d₆): δ 11.53 (br. s., 1H), 8.49-8.60 (m, 1H), 7.51-7.62 (m, 1H), 7.05-7.14 (m, 2H), 6.94-7.01 (m, 1H), 6.27 (br. s., 1H), 4.56 (br. s., 1H), 4.31-4.49 (m, 5H), 3.89 (s, 3H), 3.58-3.73 (m, 2H), 3.35-3.53 (m, 2H), 2.03-2.16 (m, 2H), 1.33 (t, 3H).

Example 13

(4-((4-ethoxy-7H-pyrrolo-[2,3-d]-pyrimidin-2-yl)amino)-3-methoxyphenyl)(2-methyl-2,7-diazaspiro-[3.5]-nonan-7-yl)methanone (E13)

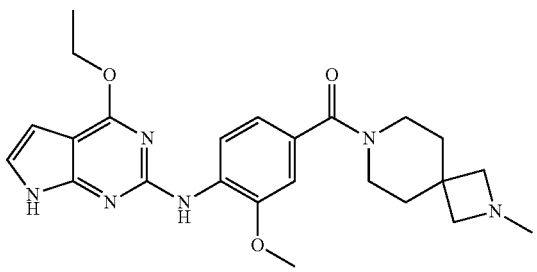 [SMILES: CCOc1nc(Nc2ccc(C(=O)N3CCC4(CC3)CN(C)C4)cc2OC)nc2[nH]ccc12]

The title compound E13 was prepared according to the general procedures 5 for Buchwald reaction starting from 2-chloro-4-ethoxy-7H-pyrrolo-[2,3-d]pyrimidine (which can be prepared according to D1) and tert-butyl 7-(4-amino-3-methoxybenzoyl)-2,7-diazaspiro[3.5]nonane-2-carboxylate (which can be prepared according to D58) as 24.3 mg of a white solid. Yield: 29.2%.

LCMS: 451[M+H]⁺. $t_R$=2.06. (LCMS condition 1)
¹H NMR (400 MHz, DMSO-d₆): δ 11.59 (br. s., 1H), 8.59 (d, J=8.3 Hz, 1H), 7.63 (s, 1H), 6.96-7.07 (m, 3H), 6.33 (dd, J=3.3, 1.8 Hz, 1H), 4.51 (q, J=7.1 Hz, 2H), 3.92 (s, 3H), 3.40-3.50 (m, 4H), 3.01 (s, 4H), 2.51 (s, 8H), 2.26 (s, 3H), 1.69 (br. s., 4H), 1.40 (t, 3H).

Example 14

4-((4-ethoxy-7H-pyrrolo-[2,3-d]pyrimidin-2-yl)amino)-N-(2-hydroxy-2-methylpropyl)-3-methoxybenzamide (E14)

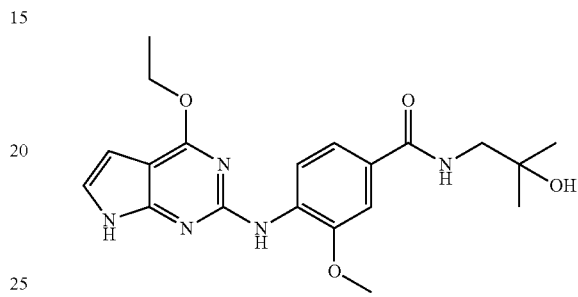

A solution of 4-((4-ethoxy-7-tosyl-7H-pyrrolo[2,3-d]pyrimidin-2-yl)amino)-N-(2-hydroxy-2-methylpropyl)-3-methoxybenzamide (which can be prepared according to D96) (150 mg, 0.271 mmol) and sodium hydroxide (0.558 mL, 1.116 mmol, 2M in water) in isopropanol (5 mL) was stirred overnight at 60° C. The mixture was concentrated and 2N HCl was added until pH=7. The mixture was then extracted with EA. The organic layer was dried and concentrated. The crude was purified by prep-HPLC to give the title compound E14 (77 mg, 0.193 mmol, 71.1% yield) as a white solid.

LCMS: 400[M+H]⁺. $t_R$=1.251. (LCMS condition 2)
¹H NMR (400 MHz, DMSO-d₆): δ 11.60 (br. s., 1H), 8.64 (d, J=8.3 Hz, 1H), 8.18 (t, J=5.9 Hz, 1H), 7.68 (s, 1H), 7.44-7.61 (m, 2H), 7.07 (d, J=3.0 Hz, 1H), 6.34 (d, J=1.8 Hz, 1H), 4.60 (s, 1H), 4.52 (q, J=7.0 Hz, 2H), 3.98 (s, 3H), 3.27 (d, J=6.0 Hz, 2H), 1.41 (t, J=7.0 Hz, 3H), 1.12 (s, 6H).

Example 15

(4-((4-ethoxy-7H-pyrrolo-[2,3-d]-pyrimidin-2-yl)amino)phenyl)(4-methylpiperazin-1-yl)methanone (E15)

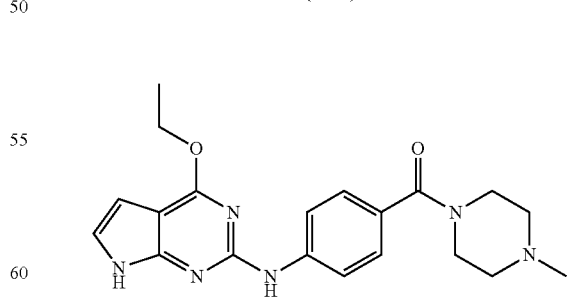

A solution of (4-((4-ethoxy-7-tosyl-7H-pyrrolo[2,3-d]pyrimidin-2-yl)amino)phenyl)(4-methylpiperazin-1-yl)methanone (which can be prepared according to D97) (250 mg, 0.468 mmol) and sodium hydroxide (0.23 mL, 0.47 mmol, 2M in water) in isopropanol (5 mL) was stirred overnight at 60° C. The reaction mixture was concentrated in vacuum. The residue was poured into water and extracted with DCM (20 mL×3). The combined organic layer was dried over Na$_2$SO$_4$, filtered and concentrated in vacuum. The crude was purified by column chromatography on silica gel (DCM: MeOH=20:1) to give the title compound E15 (56 mg, 0.147 mmol, 31.5% yield) as a white solid.

LCMS: 381.1[M+H]$^+$. t$_R$=1.148. (LCMS condition 2)

$^1$HNMR (400 MHz, DMSO-d$_6$): δ 11.49 (s, 1H), 9.37 (s, 1H), 7.91 (d, 2H), 7.31 (d, 2H), 7.01 (d, 1H), 6.31 (d, 1H), 4.53 (dd, J=9.0 Hz, 2H), 3.49 (s, 3H), 2.30 (s, 4H), 2.18 (s, 3H), 1.40 (t, J=9.0 Hz, 3H).

Example 16

(4-((4-ethoxy-7H-pyrrolo-[2,3-d]-pyrimidin-2-yl)amino)-3-methoxyphenyl)(6-azaspiro-[2.5]octan-6-yl)methanone (E16)

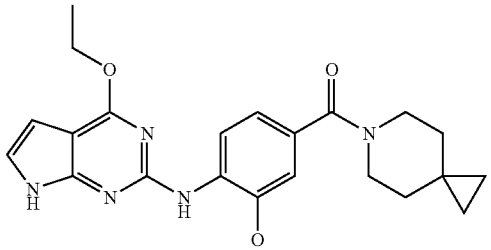 [SMILES: CCOc1nc(Nc2ccc(C(=O)N3CCC4(CC3)CC4)cc2O)nc2[nH]ccc12]

A solution of (4-((4-ethoxy-7-tosyl-7H-pyrrolo[2,3-d]pyrimidin-2-yl)amino)-3-methoxyphenyl)(6-azaspiro[2.5]octan-6-yl)methanone (which can be prepared according to D98) (150 mg, 0.261 mmol) and sodium hydroxide (0.558 mL, 1.116 mmol, 2M in water) in isopropanol (5 mL) was stirred overnight at 60° C. The mixture was concentrated and 2N HCl was added until pH=7. The mixture was then extracted with EA. The organic layer was dried and concentrated. The crude was purified by prep-HPLC to give the title compound E16 (90 mg, 0.214 mmol, 82% yield) as a white solid.

LCMS: 422[M+H]$^+$. t$_R$=1.456. (LCMS condition 2)

$^1$H NMR (400 MHz, DMSO-d$_6$): δ 11.58 (br. s., 1H), 8.59 (d, J=8.3 Hz, 1H), 7.62 (s, 1H), 6.92-7.11 (m, 3H), 6.33 (s, 1H), 4.51 (d, J=7.0 Hz, 2H), 3.93 (s, 3H), 3.39-3.74 (m, 4H), 1.10-1.60 (m, 7H), 0.36 (s, 4H).

Example 17

(4-((4-ethoxy-7H-pyrrolo-[2,3-d]-pyrimidin-2-yl)amino)-3-methoxyphenyl)(oxazolidin-3-yl) methanone (E17)

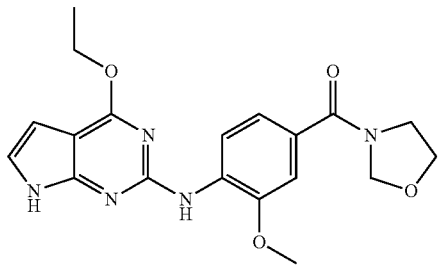 [SMILES: CCOc1nc(Nc2ccc(C(=O)N3CCOC3)cc2OC)nc2[nH]ccc12]

A solution of (4-((4-ethoxy-7-tosyl-7H-pyrrolo[2,3-d]pyrimidin-2-yl)amino)-3-methoxyphenyl)(oxazolidin-3-yl)methanone (which can be prepared according to D99) (200 mg, 0.372 mmol) and sodium hydroxide (0.558 mL, 1.116 mmol, 2M in water) in isopropanol (5 mL) was stirred overnight at 60° C. The mixture was concentrated and 2N HCl was added until pH=7. The mixture was then extracted with EA. The organic layer was dried and concentrated. The crude was purified by prep-HPLC to give the title compound E17 (33 mg, 0.082 mmol, 22.09% yield) as a white solid.

LCMS: 384[M+H]$^+$. t$_R$=1.572. (LCMS condition 2)

$^1$H NMR (400 MHz, DMSO-d$_6$): δ 11.62 (br. s., 1H), 8.65 (d, J=8.8 Hz, 1H), 7.67 (s, 1H), 7.13-7.32 (m, 2H), 7.06 (d, J=1.8 Hz, 1H), 6.33 (d, J=2.8 Hz, 1H), 4.98 (s, 2H), 4.51 (q, J=7.0 Hz, 2H), 4.00 (t, J=6.4 Hz, 2H), 3.95 (s, 3H), 3.55-3.73 (m, 2H), 1.40 (t, J=7.0 Hz, 3H).

Example 18

(4-((4-ethoxy-7H-pyrrolo-[2,3-d]-pyrimidin-2-yl)amino)-2-methoxyphenyl)(morpholino)methanone (E18)

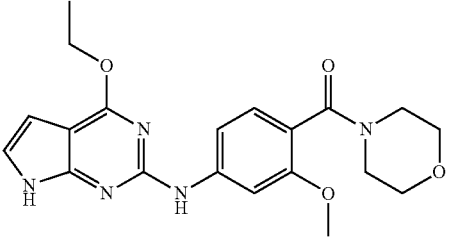 [SMILES: CCOc1nc(Nc2ccc(C(=O)N3CCOCC3)c(OC)c2)nc2[nH]ccc12]

A solution of (4-((4-ethoxy-7-tosyl-7H-pyrrolo[2,3-d]pyrimidin-2-yl)amino)-2-methoxyphenyl)(morpholino)methanone (which can be prepared according to D100) (170 mg, 0.308 mmol) and sodium hydroxide (0.770 mL, 1.541 mmol, 2M in water) in isopropanol (5.0 mL) was stirred overnight at 60° C. The reaction mixture was concentrated in vacuum. The residue was poured into water and extracted with EtOAc (20 mL×3). The combined extracts were dried over Na$_2$SO$_4$, filtered and concentrated in vacuum. The crude was purified by prep-HPLC to give the title compound E18 (20 mg, 0.050 mmol, 16.13% yield) as a white solid.

LCMS: 398[M+H]$^+$. t$_R$=1.497. (LCMS condition 2)

$^1$H NMR (400 MHz, DMSO-d$_6$): δ 11.47 (br. s., 1H), 9.30 (s, 1H), 7.82 (s, 1H), 7.30-7.49 (m, 1H), 6.94-7.14 (m, 2H), 6.31 (d, J=1.3 Hz, 1H), 4.55 (q, J=7.2 Hz, 2H), 3.82 (s, 3H), 3.60 (br. s., 6H), 3.19 (br. s., 2H), 1.40 (t, J=7.0 Hz, 3H).

Example 19

(3-(dimethylamino)-4-((4-ethoxy-7H-pyrrolo-[2,3-d]-pyrimidin-2-yl)amino)phenyl)-(morpholino)methanone (E19)

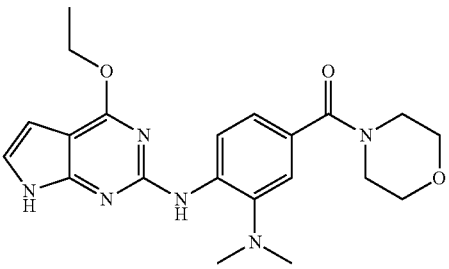 [SMILES: CCOc1nc(Nc2ccc(C(=O)N3CCOCC3)cc2N(C)C)nc2[nH]ccc12]

A solution of (3-(dimethylamino)-4-((4-ethoxy-7-tosyl-7H-pyrrolo[2,3-d]pyrimidin-2-yl)amino)phenyl)(morpholino)methanone (which can be prepared according to D101) (250 mg, 0.443 mmol) and sodium hydroxide (0.221 mL, 0.442 mmol, 2M in water) in isopropanol (5.0 mL) was stirred overnight at 60° C. The reaction mixture was quenched with water and extracted with DCM (20 mL×3). The combined organic layer was dried over Na₂SO₄, filtered and concentrated in vacuum. The crude was purified by column chromatography on silica gel (DCM:CH₃OH=20:1) to give the title compound E19 ((62 mg, 0.151 mmol, 34.1% yield) as a white solid.

LCMS: 411[M+H]⁺. $t_R$=1.32. (LCMS condition 2)

¹H NMR (400 MHz, DMSO-d₆): δ 11.57 (s, 1H), 8.64 (d, 1H, J=10.5 Hz, 1H), 8.06 (s, 1H), 7.28 (s, 1H), 7.19 (d, J=8.5 Hz, 1H), 7.04 (s, 1H), 6.33 (s, 1H), 4.51 (dd, J=8.5 Hz, 9.0 Hz, 2H), 0.59 (s, 4H), 3.52 (s, 4H), 2.65 (s, 6H), 1.39 (t, J=9.0 Hz, 3H).

Example 20

(3-ethoxy-4-((4-ethoxy-7H-pyrrolo-[2,3-d]pyrimidin-2-yl)amino)phenyl)(morpholino)methanone (E20)

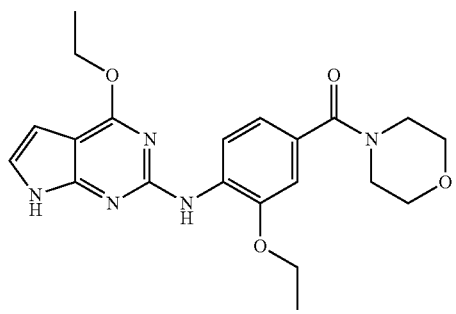 [SMILES: CCOc1cc(C(=O)N2CCOCC2)ccc1Nc1nc(OCC)c2cc[nH]c2n1]

A solution of (3-ethoxy-4-((4-ethoxy-7-tosyl-7H-pyrrolo[2,3-d]pyrimidin-2-yl)amino)phenyl)(morpholino)methanone (which can be prepared according to D102) (250 mg, 0.442 mmol) and sodium hydroxide (0.221 mL, 0.442 mmol, 2M in water) in isopropanol (5.0 mL) was stirred overnight 60° C. The reaction mixture was quenched with water and extracted with DCM (20 mL×3). The combined organic layer was dried over Na₂SO₄, filtered and concentrated in vacuum. The crude was purified by column chromatography on silica gel (DCM:CH₃OH=20:1) to give the title compound E20 (96 mg, 0.233 mmol, 52.8% yield) as a white solid.

LCMS: 412.1[M+H]⁺. $t_R$=1.31. (LCMS condition 2)

¹H NMR (400 MHz, DMSO-d₆): δ 11.57 (s, 1H), 8.61 (d, J=10.0 Hz, 1H), 7.60 (s, 1H), 7.04 (m, 3H), 6.32 (s, 1H), 4.53 (dd, J=8.0 Hz, 9.0 Hz, 2H), 4.17 (dd, J=8.0 Hz, 9.0 Hz, 2H), 3.59 (s, 4H), 3.51 (s, 4H), 1.41 (m, 6H).

Example 21

(4-((4-ethoxy-7H-pyrrolo-[2,3-d]-pyrimidin-2-yl)amino)-3-isopropoxyphenyl)(morpholino)methanone (E21)

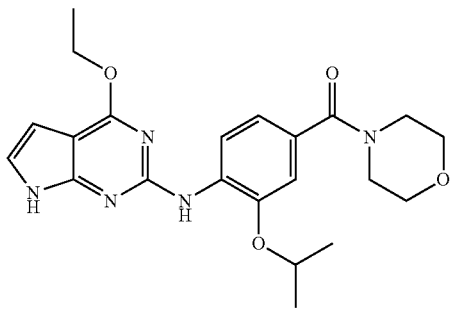 [SMILES: CCOc1nc(Nc2ccc(C(=O)N3CCOCC3)cc2OC(C)C)nc2[nH]ccc12]

A solution of (4-((4-ethoxy-7-tosyl-7H-pyrrolo[2,3-d]pyrimidin-2-yl)amino)-3-isopropoxyphenyl)(morpholino)methanone (which can be prepared according to D103) (200 mg, 0.345 mmol) and sodium hydroxide (0.173 mL, 0.345 mmol, 2M in water) in isopropanol (5.0 mL) was stirred overnight at 60° C. The reaction mixture was quenched with water and extracted with DCM (20 mL×3). The combined organic layer was dried over Na₂SO₄, filtered and concentrated in vacuum. The crude was purified by column chromatography on silica gel (DCM:CH₃OH=20:1) to give the title compound E21 (67 mg, 0.157 mmol, 45.6% yield) as a white solid.

LCMS: 426.2[M+H]⁺. $t_R$=1.36. (LCMS condition 2)

¹H NMR (400 MHz, DMSO-d₆): δ 11.57 (s, 1H), 8.63 (d, J=10.0 Hz, 1H), 7.57 (s, 1H), 7.04 (m, 3H), 6.32 (s, 1H), 4.73 (m, 1H), 4.51 (dd, J=8.0 Hz, 9.0 Hz, 2H), 3.59 (s, 4H), 3.51 (s, 4H), 1.39 (t, J=8.5 Hz, 3H), 1.35 (d, J=7.5 Hz, 6H).

Example 22

(4-((4-ethoxy-7H-pyrrolo-[2,3-d]-pyrimidin-2-yl)amino)-3-fluorophenyl)(4-methylpiperazin-1-yl)methanone (E22)

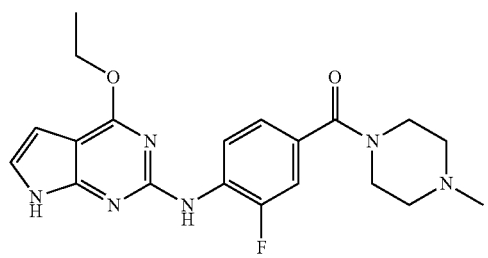 [SMILES: CCOc1nc(Nc2ccc(C(=O)N3CCN(C)CC3)cc2F)nc2[nH]ccc12]

A solution of (4-((4-ethoxy-7-tosyl-7H-pyrrolo[2,3-d]pyrimidin-2-yl)amino)-3-fluorophenyl)(4-methylpiperazin-1-yl)methanone (which can be prepared according to D104) (100 mg, 0.181 mmol) and sodium hydroxide (0.181 mL, 0.362 mmol, 2M in water) in THF (10 mL) was stirred overnight at 50° C. The reaction mixture was poured into EtOAc (20 mL) and extracted with water (3×30 mL). The organic layer was evaporated in vacuum and the crude was purified by prep-HPLC to give the title compound E22 (16 mg, 0.039 mmol, 21.30% yield) as a white solid.

LCMS: 399[M+H]$^+$. $t_R$=1.513. (LCMS condition 2)

$^1$H NMR (400 MHz, DMSO-d$_6$): δ 11.51 (br. s., 1H), 8.55 (s, 1H), 8.22 (s, 1H), 7.26 (d, J=11.3 Hz, 1H), 7.20 (d, J=8.5 Hz, 1H), 6.98-7.04 (m, 1H), 6.27-6.34 (m, 1H), 4.46-4.53 (m, 2H), 3.50 (br. s., 4H), 2.32 (br. s., 4H), 2.20 (s, 3H), 1.38 (t, J=7.1 Hz, 3H).

Example 23

(3-chloro-4-((4-ethoxy-7H-pyrrolo-[2,3-d]pyrimidin-2-yl)amino)phenyl)(4-methylpiperazin-1-yl)methanone (E23)

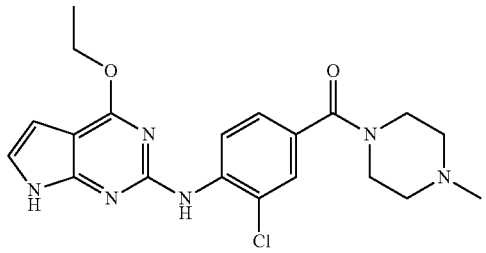 [SMILES: CCOc1nc(Nc2ccc(C(=O)N3CCN(C)CC3)cc2Cl)nc2[nH]ccc12]

A solution of (3-chloro-4-((4-ethoxy-7-tosyl-7H-pyrrolo-[2,3-d]pyrimidin-2-yl)amino)phenyl)(4-methylpiperazin-1-yl)-methanone (which can be prepared according to D123) (40 mg, 0.070 mmol) and sodium hydroxide (1 mL, 2.0 mmol, 2M in water) in methanol (3 mL) was stirred at 20° C. for 2 hours. The mixture was extracted with ethyl acetate. The organic layer was dried with Na$_2$SO$_4$ and concentrated. The crude was purified by prep-HPLC to give the title compound E23 (18 mg, 0.042 mmol, 59.9% yield) as a white solid.

LCMS: 415[M+H]$^+$. $t_R$=1.582. (LCMS condition 2)

$^1$H NMR (400 MHz, METHANOL-d$_4$): δ 8.85 (d, J=8.8 Hz, 1H), 7.54 (d, J=1.8 Hz, 1H), 7.40 (dd, J=8.8, 1.8 Hz, 1H), 7.00 (d, J=3.5 Hz, 1H), 6.41 (d, J=3.5 Hz, 1H), 4.58 (q, J=7.0 Hz, 2H), 3.68 (br. s., 4H), 2.50 (br. s., 4H), 2.35 (s, 3H), 1.48 (t, J=7.2 Hz, 3H).

Example 24

(4-((4-ethoxy-7H-pyrrolo-[2,3-d]pyrimidin-2-yl)amino)-3-isopropoxyphenyl)(4-methylpiperazin-1-yl)methanone (E24)

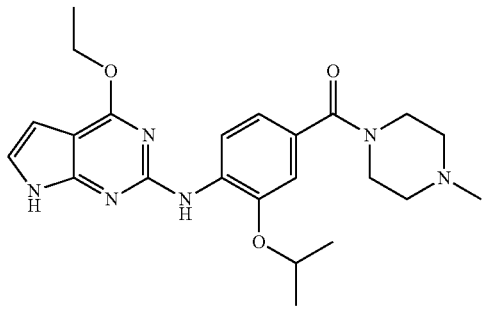 [SMILES: CCOc1nc(Nc2ccc(C(=O)N3CCN(C)CC3)cc2OC(C)C)nc2[nH]ccc12]

A solution of (4-((4-ethoxy-7-tosyl-7H-pyrrolo[2,3-d]pyrimidin-2-yl)amino)-3-isopropoxyphenyl)(4-methylpiperazin-1-yl)methanone (which can be prepared according to D105) (100 mg, 0.169 mmol) and sodium hydroxide (0.169 mL, 0.337 mmol, 2M in water) in THF (10 mL) was stirred overnight at 50° C. The reaction mixture was poured into EtOAc (20 mL) and extracted with water (3×30 mL). The organic layer was evaporated in vacuum and the crude was purified by prep-HPLC to give the title compound E24 (45 mg, 0.100 mmol, 59.0% yield) as a yellow solid.

LCMS: 437[M+H]$^+$. $t_R$=1.626. (LCMS condition 2)

$^1$H NMR (400 MHz, DMSO-d$_6$): δ 11.57 (br. s., 1H), 8.62 (d, J=8.3 Hz, 1H), 7.58 (s, 1H), 6.91-7.10 (m, 3H), 6.34 (d, J=1.3 Hz, 1H), 4.67-4.82 (m, 1H), 4.52 (q, J=7.0 Hz, 2H), 3.51 (br. s., 4H), 2.32 (br. s., 4H), 2.20 (s, 3H), 1.41 (t, J=7.0 Hz, 3H), 1.36 (d, J=6.0 Hz, 6H).

Example 25

(3-ethoxy-4-((4-ethoxy-7H-pyrrolo-[2,3-d]pyrimidin-2-yl)amino)phenyl)(4-methylpiperazin-1-yl)methanone (E25)

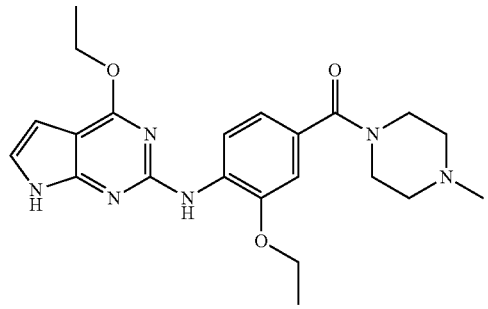 [SMILES: CCOc1cc(C(=O)N2CCN(C)CC2)ccc1Nc1nc(OCC)c2cc[nH]c2n1]

A solution of (3-ethoxy-4-((4-ethoxy-7-tosyl-7H-pyrrolo[2,3-d]pyrimidin-2-yl)amino)phenyl)(4-methylpiperazin-1-yl)methanone (which can be prepared according to D106) (100 mg, 0.173 mmol) and sodium hydroxide (0.173 mL, 0.346 mmol, 2M in water) in THF (10 mL) was stirred overnight at 60° C. The reaction mixture was poured into EtOAc (20 mL) and extracted with water (3×30 mL). The organic layer was evaporated in vacuum and the crude was purified by prep-HPLC to give the title compound E25 (60 mg, 0.140 mmol, 81% yield) as a yellow solid.

LCMS: 425[M+H]$^+$. $t_R$=1.583. (LCMS condition 2)

$^1$H NMR (400 MHz, DMSO-d$_6$): δ 11.58 (br. s., 1H), 8.61 (d, J=8.0 Hz, 1H), 7.61 (s, 1H), 6.92-7.12 (m, 3H), 6.34 (d, J=2.0 Hz, 1H), 4.52 (q, J=7.0 Hz, 2H), 4.19 (q, J=7.0 Hz, 2H), 3.52 (br. s., 4H), 2.32 (br. s., 4H), 2.20 (s, 3H), 1.42 (m, 6H).

Example 26

(3-(dimethylamino)-4-((4-ethoxy-7H-pyrrolo-[2,3-d]pyrimidin-2-yl)amino)phenyl)(4-methylpiperazin-1-yl) methanone (E26)

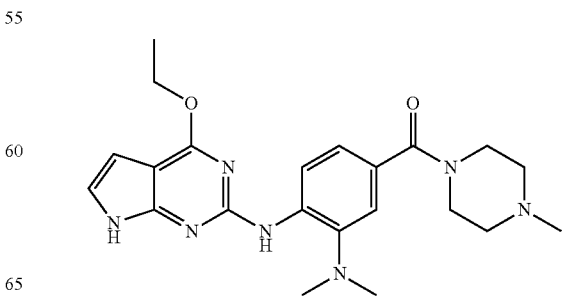

To a solution of (3-(dimethylamino)-4-((4-ethoxy-7-tosyl-7H-pyrrolo[2,3-d]pyrimidin-2-yl)amino)phenyl)(4-methylpiperazin-1-yl)methanone (which can be prepared according to D107) (100 mg, 0.173 mmol) in THF (10 mL) was added NaOH (0.173 mL, 0.346 mmol). The reaction mixture was stirred overnight at 60° C. The reaction mixture was poured into EtOAc (20 mL) and washed with water (3×30 mL). The organic layer was evaporated in vacuum and the crude was purified by prep-HPLC to give the title compound E26 (50 mg, 0.116 mmol, 66.8% yield) as a white solid.

LCMS: 425[M+H]$^+$. $t_R$=1.59. (LCMS condition 2)

$^1$H NMR (400 MHz, DMSO-d$_6$): δ 11.58 (br. s., 1H), 8.63 (d, J=8.3 Hz, 1H), 8.07 (s, 1H), 7.26 (d, J=1.3 Hz, 1H), 7.12-7.22 (m, 1H), 6.99-7.10 (m, 1H), 6.34 (d, J=1.5 Hz, 1H), 4.52 (q, J=7.0 Hz, 2H), 3.52 (br. s., 4H), 2.66 (s, 6H), 2.32 (br. s., 4H), 2.20 (s, 3H), 1.41 (t, J=7.0 Hz, 3H).

Example 27

(S)-(4-((4-ethoxy-7H-pyrrolo-[2,3-d]pyrimidin-2-yl)amino)-3-methoxyphenyl)(3-methylmorpholino)methanone (E27)

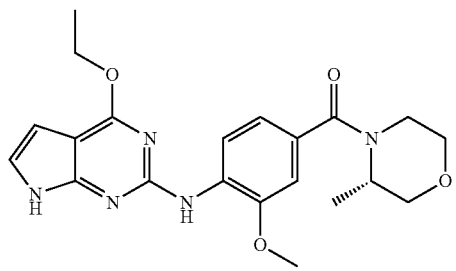 [SMILES: CCOc1nc(Nc2ccc(C(=O)N3CCOC[C@@H]3C)cc2OC)nc2[nH]ccc12]

A solution of (S)-(4-((4-ethoxy-7-tosyl-7H-pyrrolo[2,3-d]pyrimidin-2-yl)amino)-3-methoxyphenyl)(3-methylmorpholino)methanone (which can be prepared according to D108) (250 mg, 0.442 mmol) and sodium hydroxide (0.221 mL, 0.442 mmol, 2M in water) in isopropanol (5.0 mL) was stirred overnight at 60° C. The reaction mixture was concentrated in vacuum. The residue was poured into brine, extracted with ethyl acetate (20 mL×3). The organic layer was then washed with brine (20 mL×3), dried over Na$_2$SO$_4$, filtered and concentrated in vacuum. The crude was purified by column chromatography on silica gel (PE:EA=1:1) to give the title compound E27 (80 mg, 0.194 mmol, 44.0% yield) as a white solid.

LCMS: 412[M+H]$^+$. $t_R$=1.305. (LCMS condition 2)

$^1$HNMR (400 MHz, DMSO-d$_6$): δ 11.57 (s, 1H), 8.60 (d, J=10.5 Hz, 1H), 7.62 (s, 1H), 7.00 (m, 3H), 6.32 (d, J=4.0 Hz, 1H), 4.52 (dd, J=9.0 Hz, 2H), 4.17 (s, 1H), 3.92 (s, 3H), 3.79 (m, 2H), 3.59 (2H, m), 3.42 (m, 1H), 3.26 (m, 1H), 1.38 (t, J=9.0 Hz, 3H), 1.26 (d, J=8.0 Hz, 3H).

Example 28

(4-((4-ethoxy-7H-pyrrolo-[2,3-d]pyrimidin-2-yl)amino)-3-methoxy-2-methylphenyl)(morpholino)methanone (E28)

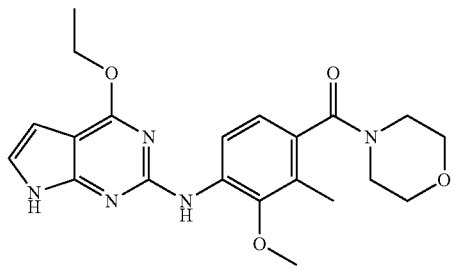 [SMILES: CCOc1nc(Nc2ccc(C(=O)N3CCOCC3)c(C)c2OC)nc2[nH]ccc12]

A solution of (4-((4-ethoxy-7-tosyl-7H-pyrrolo[2,3-d]pyrimidin-2-yl)amino)-3-methoxy-2-methylphenyl)(morpholino)methanone (which can be prepared according to D109) (250 mg, 0.442 mmol) and sodium hydroxide (0.221 mL, 0.442 mmol, 2M in water) in isopropanol (5.0 mL) was stirred overnight at 60° C. The reaction mixture was concentrated in vacuum. The residue was poured into brine, extracted with ethyl acetate (20 mL×3). The organic layer was then washed with brine (20 mL×3), dried over Na$_2$SO$_4$, filtered and concentrated in vacuum. The crude was purified by column chromatography on silica gel (PE:EA=1:1) to give the title compound E28 (125 mg, 0.304 mmol, 68.7% yield) as a white solid.

LCMS: 412[M+H]$^+$. $t_R$=1.248. (LCMS condition 2)

$^1$HNMR (400 MHz, DMSO-d$_6$): δ 11.53 (s, 1H), 8.38 (d, J=10.5 Hz, 1H), 7.67 (s, 1H), 7.02 (m, 1H), 6.95 (d, J=10.5 Hz, 1H), 6.31 (m, 1H), 4.51 (dd, J=9.0 Hz, 2H), 3.73 (s, 3H), 3.63 (m, 4H), 3.49 (m, 2H), 3.18 (m, 2H), 2.16 (s, 3H), 1.38 (t, J=9.0 Hz, 3H).

Example 29

(R)-(3,4-dimethylpiperazin-1-yl)-(4-((4-ethoxy-7H-pyrrolo-[2,3-d]-pyrimidin-2-yl)amino)-3-methoxyphenyl)methanone (E29)

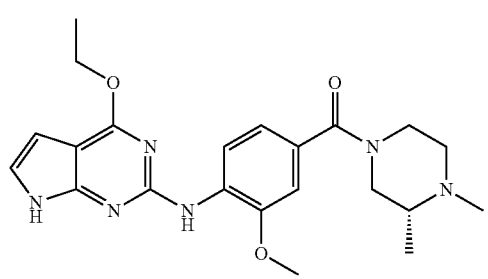 [SMILES: CCOc1nc(Nc2ccc(C(=O)N3CCN(C)[C@H](C)C3)cc2OC)nc2[nH]ccc12]

A solution of (R)-(3,4-dimethylpiperazin-1-yl)(4-((4-ethoxy-7-tosyl-7H-pyrrolo[2,3-d]pyrimidin-2-yl)amino)-3-methoxyphenyl)methanone (which can be prepared according to D110) (150 mg, 0.259 mmol) and sodium hydroxide (0.389 mL, 0.778 mmol) in isopropanol (5 mL) stirred overnight at 60° C. The mixture was concentrated and 2N HCl was added until pH=7. The mixture was then extracted with EA. The organic layer was dried and concentrated. The crude was purified by prep-HPLC to give the title compound E29 (15 mg, 0.035 mmol, 13.63% yield) as a white solid.

LCMS: 425[M+H]⁺. $t_R$=1.572. (LCMS condition 2)

¹H NMR (400 MHz, DMSO-d₆): δ 11.36-11.72 (m, 1H), 8.59 (d, J=7.8 Hz, 1H), 7.62 (br. s., 1H), 6.78-7.20 (m, 3H), 6.32 (br. s., 1H), 4.50 (d, J=6.5 Hz, 2H), 3.92 (br. s., 3H), 2.61-2.86 (m, 1H), 2.18 (br. s., 3H), 2.07 (br. s., 2H), 1.39 (t, J=6.4 Hz, 3H), 0.77-1.10 (m, 3H).

Example 30

(R)-(4-((4-ethoxy-7H-pyrrolo[2,3-d]pyrimidin-2-yl)amino)-3-methoxyphenyl)(3-methylmorpholino)methanone (E30)

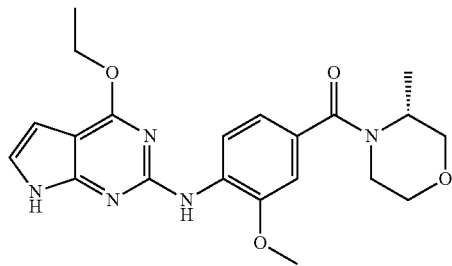 [SMILES: CCOc1nc(Nc2ccc(C(=O)N3CCOC[C@H]3C)cc2OC)nc2[nH]ccc12]

A solution of (R)-(4-((4-ethoxy-7-tosyl-7H-pyrrolo[2,3-d]pyrimidin-2-yl)amino)-3-methoxyphenyl)(3-methylmorpholino)methanone (which can be prepared according to D111)(40 mg, 0.071 mmol) and sodium hydroxide (1 mL, 2.0 mmol, 2M in water) in methanol (3 mL) was stirred at 20° C. for 2 hours. The mixture was extracted with ethyl acetate. The organic layer was dried with Na₂SO₄ and concentrated. The crude was purified by prep-HPLC to give the title compound E30 (17 mg, 0.041 mmol, 58.4% yield) as a white solid.

LCMS: 412[M+H]⁺. $t_R$=1.610. (LCMS condition 2)

¹H NMR (400 MHz, METHANOL-d₄): δ 8.75 (d, J=8.3 Hz, 1H), 7.00-7.11 (m, 2H), 6.95 (d, J=3.5 Hz, 1H), 6.38 (d, J=3.5 Hz, 1H), 4.57 (q, J=7.0 Hz, 2H), 4.20-4.46 (m, 1H), 3.99 (s, 3H), 3.80-3.97 (m, 2H), 3.60-3.76 (m, 2H), 3.38-3.59 (m, 2H), 1.48 (t, J=7.0 Hz, 3H), 1.40 (d, J=6.8 Hz, 3H).

Example 31

(4-((4-ethoxy-5-methyl-7H-pyrrolo-[2,3-d]pyrimidin-2-yl)amino)-3-methoxyphenyl)(4-methylpiperazin-1-yl)methanone (E31)

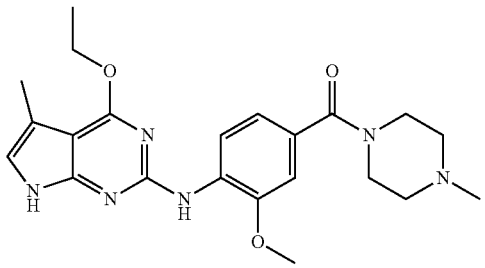 [SMILES: CCOc1nc(Nc2ccc(C(=O)N3CCN(C)CC3)cc2OC)nc2[nH]cc(C)c12]

A solution of (4-((4-ethoxy-5-methyl-7-tosyl-7H-pyrrolo[2,3-d]pyrimidin-2-yl)amino)-3-methoxyphenyl)(morpholino)methanone (which can be prepared according to D112) (60 mg, 0.104 mmol) and sodium hydroxide (2 mL, 4.00 mmol, 2M in water) in isopropanol (5 mL) was stirred overnight at 60° C. The mixture was concentrated and 2N HCl was added until pH=7. The mixture was then extracted with EA. The organic layer was dried and concentrated. The crude was purified by prep-HPLC to give the title compound E31 (10 mg, 0.024 mmol, 22.72% yield) as a white solid.

LCMS: 425 [M+H]⁺. $t_R$=1.333. (LCMS condition 2)

¹H NMR (400 MHz, DMSO-d₆): δ 11.12-11.27 (m, 1H), 8.58 (d, J=8.3 Hz, 1H), 7.57 (s, 1H), 6.89-7.08 (m, 2H), 6.75 (s, 1H), 4.47 (q, J=7.0 Hz, 2H), 3.91 (s, 3H), 3.50 (br. s., 4H), 2.31 (br. s., 4H), 2.25 (s, 3H), 2.19 (s, 3H), 1.38 (t, J=7.0 Hz, 3H).

Example 32

(4-((4-ethoxy-5-methyl-7H-pyrrolo-[2,3-d]pyrimidin-2-yl)amino)-3-methoxyphenyl)(morpholino)methanone (E32)

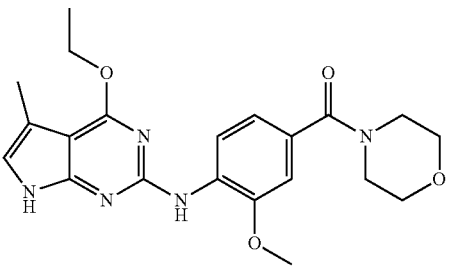 [SMILES: CCOc1nc(Nc2ccc(C(=O)N3CCOCC3)cc2OC)nc2[nH]cc(C)c12]

A solution of (4-((4-ethoxy-5-methyl-7-tosyl-7H-pyrrolo[2,3-d]pyrimidin-2-yl)amino)-3-methoxyphenyl)(4-methylpiperazin-1-yl)methanone (which can be prepared according to D113) (150 mg, 0.265 mmol) and sodium hydroxide (2 mL, 4.00 mmol, 2M in water) in isopropanol (5 mL) was stirred overnight at 60° C. The mixture was concentrated and 2N HCl was added until pH=7. The mixture was then extracted with EA. The organic layer was dried and concentrated. The crude was purified by prep-HPLC to give the title compound E32 (9 mg, 0.022 mmol, 8.25% yield) as a white solid.

LCMS: 412 [M+H]⁺. $t_R$=1.311. (LCMS condition 2)

¹H NMR (400 MHz, DMSO-d₆): δ 11.22 (br. s., 1H), 8.45-8.70 (m, 1H), 7.59 (s, 1H), 7.06 (s, 2H), 6.76 (s, 1H), 4.48 (q, J=7.0 Hz, 2H), 3.93 (s, 3H), 3.61 (br. s., 4H), 3.49-3.56 (m, 4H), 2.26 (s, 3H), 1.39 (t, J=7.0 Hz, 3H).

Example 33

(4-((4-(cyclopropylmethoxy)-7H-pyrrolo-[2,3-d]pyrimidin-2-yl)amino)-3-methoxyphenyl)(4-methylpiperazin-1-yl) methanone (E33)

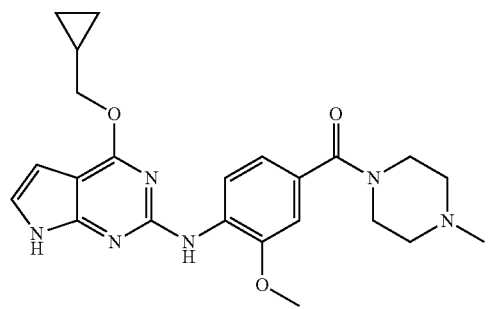 [SMILES: COc1cc(C(=O)N2CCN(C)CC2)ccc1Nc1nc(OCC2CC2)c2cc[nH]c2n1]

A solution of 2-chloro-4-(cyclopropylmethoxy)-7H-pyrrolo-[2,3-d]-pyrimidine (which can be prepared according to D87) (150 mg, 0.671 mmol), (4-amino-3-methoxyphenyl)(4-methylpiperazin-1-yl) methanone (201 mg, 0.805 mmol), xantphos (39.2 mg, 0.068 mmol), Pd$_2$(dba)$_3$ (31.3 mg, 0.034 mmol) and K$_2$CO$_3$ (282 mg, 2.039 mmol) in 2-butanol (2.0 mL) was irradiated by microwave at 120° C. for 45 min. The reaction mixture was quenched with water and extracted with EtOAc (20 mL×3). The combined extracts were dried over Na$_2$SO$_4$, filtered and concentrated in vacuum. The crude was purified via column chromatography on silica gel (DCM:MeOH=20:1) to give the title compound E33 (80 mg, 0.183 mmol, 27.3% yield) as a white solid.

LCMS: 437 [M+H]$^+$. t$_R$=1.292. (LCMS condition 2)

$^1$H NMR (400 MHz, DMSO-d$_6$): δ 11.59 (s, 1H), 8.60 (d, J=10.5 Hz, 1H), 7.62 (s, 1H), 7.03 (m, 3H), 8.35 (d, J=4.0 Hz, 1H), 4.29 (d, J=9.0 Hz, 2H), 3.91 (s, 3H), 3.52 (m, 8H), 1.31 (m, 1H), 0.58 (m, 2H), 0.38 (m, 2H).

Example 34

(4-((4-(cyclopropylmethoxy)-7H-pyrrolo-[2,3-d]pyrimidin-2-yl)amino)-3-methoxyphenyl)(morpholino)methanone (E34)

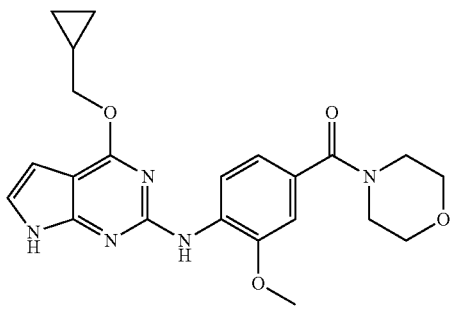 [SMILES: COc1cc(C(=O)N2CCOCC2)ccc1Nc1nc(OCC2CC2)c2cc[nH]c2n1]

A solution of 2-chloro-4-(cyclopropylmethoxy)-7H-pyrrolo-[2,3-d]-pyrimidine (which can be prepared according to D87) (150 mg 0.671 mmol), (4-amino-3-methoxyphenyl)(morpholino)methanone (190 mg, 0.805 mmol), xantphos (39.2 mg, 0.068 mmol), Pd$_2$(dba)$_3$ (31.3 mg, 0.034 mmol) and K$_2$CO$_3$ (282 mg, 2.039 mmol) in 2-butanol (2.0 mL) was irradiated by microwave at 120° C. for 45 min. The reaction mixture was quenched with water and extracted with EtOAc (20 mL×3). The combined extracts were dried over Na$_2$SO$_4$, filtered and concentrated in vacuum. The crude was purified by column chromatography on silica gel (DCM:MeOH=20:1) to give the title compound E34 (107 mg, 0.253 mmol, 37.7% yield) as a white solid.

LCMS: 424[M+H]$^+$. t$_R$=1.32. (LCMS condition 2)

$^1$H NMR (400 MHz, DMSO-d$_6$): δ 11.59 (1H, s), 8.60 (1H, d, J=10.5 Hz), 7.62 (1H, s), 7.03 (3H, m), 8.35 (1H, d, J=4.0 Hz), 4.29 (2H, d, J=9.0 Hz), 3.91 (3H, s), 3.52 (8H, m), 1.31 (1H, m), 0.58 (2H, m), 0.38 (2H, s).

Example 35

(R)-(4-((4-ethoxy-7H-pyrrolo-[2,3-d]pyrimidin-2-yl)amino)-3-methoxyphenyl)(2-(methoxymethyl)pyrrolidin-1-yl)methanone (E35)

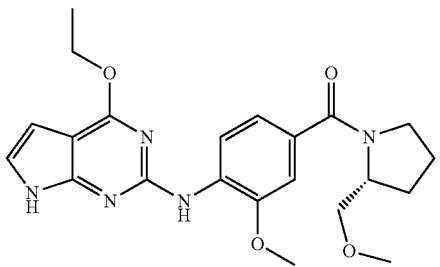 [SMILES: CCOc1nc(Nc2ccc(C(=O)N3CCC[C@@H]3COC)cc2OC)nc2[nH]ccc12]

A solution of (R)-(4-((4-ethoxy-7-tosyl-7H-pyrrolo[2,3-d]pyrimidin-2-yl)amino)-3-methoxyphenyl)(2-(methoxymethyl)pyrrolidin-1-yl)methanone (which can be prepared according to D125) (160 mg, 0.276 mmol) and NaOH (166 mg, 4.14 mmol) in isopropanol (5 mL) and water (5.00 mL) was stirred at 60° C. for 4 hours. The mixture was diluted with EA, washed with water. The organic layer was dried and concentrated. The crude was purified via MDAP (basic mobile phase) to give the title compound E35 (51 mg, 0.120 mmol, 43.4% yield) as a white solid.

LCMS: 426[M+H]$^+$. t$_R$=3.213. (LCMS condition 1)

$^1$H NMR (400 MHz, CHLOROFORM-d): δ 8.56-8.71 (m, 1H), 8.32-8.52 (m, 1H), 7.60-7.72 (m, 1H), 7.08-7.24 (m, 2H), 6.78-6.96 (m, 1H), 6.33-6.58 (m, 1H), 4.58 (d, J=7.1 Hz, 2H), 4.38-4.51 (m, 1H), 3.96 (s, 3H), 3.53-3.77 (m, 4H), 3.25-3.49 (m, 3H), 1.88-2.14 (m, 3H), 1.68-1.83 (m, 1H), 1.49 (t, J=7.1 Hz, 3H).

Example 36

(4-((4-ethoxy-7H-pyrrolo-[2,3-d]pyrimidin-2-yl)amino)-3-methoxyphenyl)(4-fluoropiperidin-1-yl)methanone (E36)

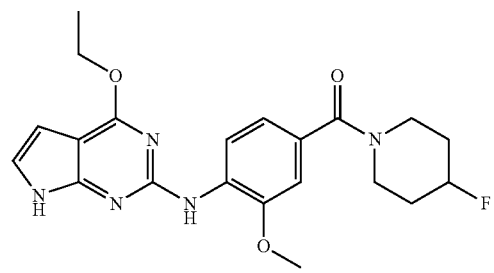 [SMILES: CCOc1nc(Nc2ccc(C(=O)N3CCC(F)CC3)cc2OC)nc2[nH]ccc12]

A solution of 2-chloro-4-ethoxy-7H-pyrrolo-[2,3-d]pyrimidine (which can be prepared according to D1) (60 mg, 0.304 mmol), (4-amino-3-methoxyphenyl)(4-fluoropiperidin-1-yl)methanone (which can be prepared according to D74) (122 mg, 0.334 mmol), Pd$_2$(dba)$_3$ (13.90 mg, 0.015 mmol), dicyclohexyl(2',4',6'-triisopropyl-[1,1'-biphenyl]-2-yl)phosphine (15.05 mg, 0.032 mmol), and potassium carbonate (126 mg, 0.911 mmol) in 2-butanol (6 mL) was irradiated by microwave to 120° C. for 45 min. The mixture was filtrated with Celite and the solution was concentrated.

The crude was purified via MADP (basic mobile phase) to give the title compound E36 (30.5 mg, 0.070 mmol, 23.08% yield) as a white solid.

LCMS: 414[M+H]$^+$. $t_R$=3.19. (LCMS condition 1)

$^1$H NMR (400 MHz, DMSO-d$_6$): δ 11.52 (br. s., 1H), 8.53 (d, J=8.1 Hz, 1H), 7.56 (s, 1H), 6.85-7.07 (m, 3H), 6.26 (dd, J=3.2, 1.7 Hz, 1H), 4.72-5.03 (m, 1H), 4.44 (q, J=7.1 Hz, 2H), 3.76-4.00 (m, 3H), 3.54 (br. s., 4H), 1.67 (br. s., 4H), 1.33 (t, 3H).

Example 37

(S)-(2,4-dimethylpiperazin-1-yl)(4-((4-ethoxy-7H-pyrrolo-[2,3-d]-pyrimidin-2-yl)amino)-3-methoxyphenyl)methanone (E37)

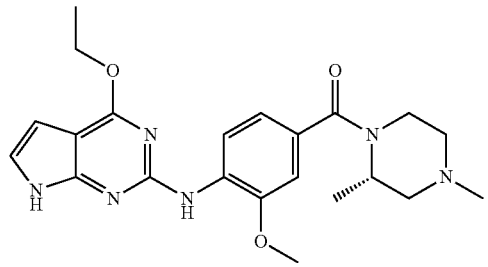 [SMILES: CCOc1nc(Nc2ccc(C(=O)N3CCN(C)C[C@@H]3C)cc2OC)nc2[nH]ccc12]

A solution of (S)-(2,4-dimethylpiperazin-1-yl)(4-((4-ethoxy-7-tosyl-7H-pyrrolo[2,3-d]pyrimidin-2-yl)amino)-3-methoxyphenyl)methanone (which be prepared according to D114) (100 mg, 0.173 mmol) and sodium hydroxide (0.259 mL, 0.518 mmol, 2M in water) in isopropanol (5 mL) was stirred overnight at 60° C. The mixture was concentrated and 2N HCl was added until pH=7. The mixture was then extracted with EA. The organic layer was dried and concentrated. The crude was purified by prep-HPLC to give the title compound E37 (7 mg, 0.016 mmol, 9.54% yield) as a white solid.

LCMS: 425[M+H]$^+$. $t_R$=1.262. (LCMS condition 2)

$^1$H NMR (400 MHz, DMSO-d$_6$): δ 11.58 (br. s., 1H), 8.60 (d, J=8.3 Hz, 1H), 7.63 (s, 1H), 6.80-7.17 (m, 3H), 6.10-6.47 (m, 1H), 4.52 (q, J=7.0 Hz, 2H), 3.94 (s, 3H), 3.75-3.92 (m, 1H), 3.19 (br. s., 1H), 2.58-2.83 (m, 2H), 2.17 (s, 3H), 2.04 (dd, J=11.3, 3.5 Hz, 1H), 1.87 (d, J=3.0 Hz, 1H), 1.41 (t, J=7.2 Hz, 3H), 1.29 (d, J=6.8 Hz, 3H).

Example 38

(2-chloro-4-((4-ethoxy-7H-pyrrolo-[2,3-d]pyrimidin-2-yl)amino)-3-methoxyphenyl)(4-methylpiperazin-1-yl)methanone (E38)

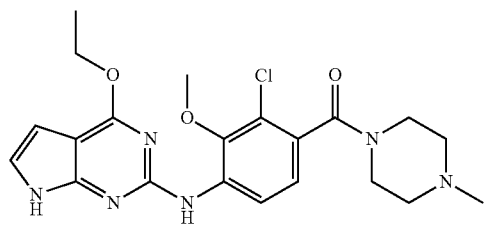 [SMILES: CCOc1nc(Nc2ccc(C(=O)N3CCN(C)CC3)c(Cl)c2OC)nc2[nH]ccc12]

A solution of (2-chloro-4-((4-ethoxy-7-tosyl-7H-pyrrolo[2,3-d]pyrimidin-2-yl)amino)-3-methoxyphenyl)(4-methylpiperazin-1-yl)methanone (which can be prepared according to D115) (100 mg, 0.167 mmol) and sodium hydroxide (1 mL, 2.000 mmol, 2M in water) in methanol (3 mL) was stirred at 20° C. for 2 hours. The mixture was then extracted with EA. The organic layer was dried and concentrated. The crude was purified by prep-HPLC to give the title compound E38 (6 mg, 0.013 mmol, 8.08% yield) as a white solid.

LCMS: 412[M+H]$^+$. $t_R$=1.564. (LCMS condition 2)

$^1$H NMR (400 MHz, METHANOL-d$_4$): δ 8.69-8.79 (m, 1H), 7.04-7.11 (m, 1H), 6.87-7.01 (m, 1H), 6.39 (d, J=3.5 Hz, 1H), 4.51-4.61 (m, 2H), 3.94 (s, 3H), 3.80 (br. s., 2H), 3.33-3.39 (m, 2H), 2.37-2.60 (m, 4H), 2.33 (s, 3H), 1.48 (t, 3H)

Example 39

(R)-(4-((4-ethoxy-7H-pyrrolo-[2,3-d]-pyrimidin-2-yl)amino)-3-methoxyphenyl)(hexahydropyrrolo[1,2-a]pyrazin-2(1H)-ylmethanone (E39)

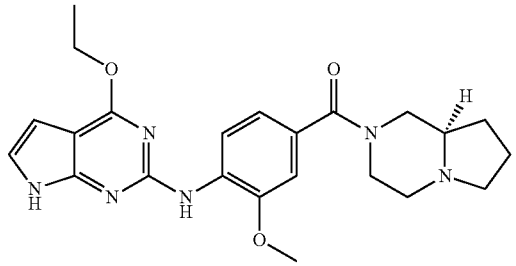 [SMILES: CCOc1nc(Nc2ccc(C(=O)N3CCN4CCC[C@@H]4C3)cc2OC)nc2[nH]ccc12]

A solution of (R)-(4-((4-ethoxy-7-tosyl-7H-pyrrolo[2,3-d]pyrimidin-2-yl)amino)-3-methoxyphenyl)(hexahydropyrrolo[1,2-a]pyrazin-2(1H)-yl)methanone (which can be prepared according to D116) (250 mg, 0.423 mmol) and sodium hydroxide (16.93 mg, 0.423 mmol) in isopropanol (5 mL) was stirred overnight under 60° C. The reaction mixture was concentrated in vacuum. The residue was poured into water and extracted with DCM (20 mL×3). The combined extracts were dried over Na$_2$SO$_4$, filtered and concentrated in vacuum.

The crude was purified by column chromatography on silica gel (DCM:MeOH=30:1) to give the title compound E39 (60 mg, 0.137 mmol, 32.5% yield) as a white solid.

LCMS: 437[M+H]$^+$. $t_R$=1295. (LCMS condition 2)

$^1$H NMR (400 MHz, DMSO-d$_6$): δ 11.45-11.70 (m, 1H), 8.60 (d, J=8.3 Hz, 1H), 7.63 (s, 1H), 7.04 (s, 3H), 6.33 (d, J=3.3 Hz, 1H), 4.51 (q, J=7.2 Hz, 2H), 3.93 (s, 3H), 3.33 (s, 4H), 2.99 (t, J=7.4 Hz, 2H), 2.06 (q, J=8.5 Hz, 2H), 1.87 (d, J=2.8 Hz, 1H), 1.60-1.80 (m, 3H), 1.40 (t, J=7.0 Hz, 3H), 1.17-1.34 (m, 1H).

Example 40

(R)-(2,4-dimethylpiperazin-1-yl)(4-((4-ethoxy-7H-pyrrolo-[2,3-d]-pyrimidin-2-yl)-amino)-3-methoxyphenyl)methanone (E40)

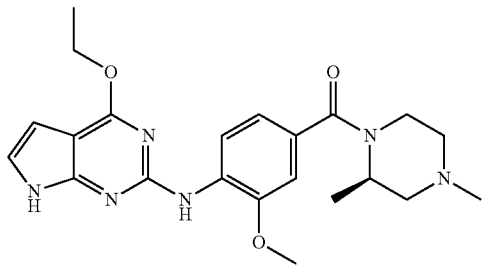 [SMILES: CCOc1nc(Nc2ccc(C(=O)N3CCN(C)C[C@H]3C)cc2OC)nc2[nH]ccc12]

A solution of (R)-(2,4-dimethylpiperazin-1-yl)(4-((4-ethoxy-7-tosyl-7H-pyrrolo[2,3-d]pyrimidin-2-yl)amino)-3-methoxyphenyl)methanone (which can be prepared according to D117) (150 mg, 0.259 mmol) and sodium hydroxide (0.389 mL, 0.778 mmol, 2M in water) in isopropanol (5 mL) was stirred overnight under 60° C. The mixture was concentrated and 2N HCl was added until pH=7. The mixture was then extracted with EA. The organic layer was dried and concentrated. The crude was purified by prep-HPLC to give the title compound E40 (27 mg, 0.064 mmol, 24.54% yield) as a white solid.

LCMS: 425[M+H]$^+$. $t_R$=1.305. (LCMS condition 2)

$^1$H NMR (400 MHz, DMSO-d$_6$): δ 11.58 (br. s., 1H), 8.59 (d, J=8.3 Hz, 1H), 7.62 (s, 1H), 6.80-7.16 (m, 3H), 6.32 (br. s., 1H), 4.49 (q, J=7.0 Hz, 2H), 4.15-4.40 (m, 1H), 3.91 (s, 4H), 3.16 (d, J=5.0 Hz, 1H), 2.56-2.79 (m, 2H), 2.15 (s, 3H), 1.73-2.06 (m, 2H), 1.38 (t, J=7.0 Hz, 3H), 1.26 (d, J=6.8 Hz, 3H).

Example 41

(S)-(3,4-dimethylpiperazin-1-yl)(4-((4-ethoxy-7H-pyrrolo-[2,3-d]-pyrimidin-2-yl)amino)-3-methoxyphenyl)methanone (E41)

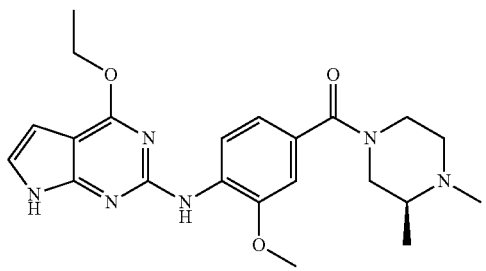 [SMILES: CCOc1nc(Nc2ccc(C(=O)N3CCN(C)[C@@H](C)C3)cc2OC)nc2[nH]ccc12]

A solution of (S)-(3,4-dimethylpiperazin-1-yl)(4-((4-ethoxy-7-tosyl-7H-pyrrolo[2,3-d]pyrimidin-2-yl)amino)-3-methoxyphenyl)methanone (which can be prepared according to D118) (220 mg, 0.371 mmol) and sodium hydroxide (0.069 mL, 0.138 mmol, 2M in water) in isopropanol (5 mL) was stirred under 60° C. for 3 hours. The mixture was concentrated and 2N HCl was added until pH=7. The mixture was then extracted with EA. The organic layer was dried and concentrated. The crude was purified by prep-HPLC to give the title compound E41 (50 mg, 0.118 mmol, 85% yield) as a white solid.

LCMS: 425[M+H]$^+$. $t_R$=1.575. (LCMS condition 2) 10 $^1$H NMR (400 MHz, DMSO-d$_6$): δ 11.59 (br. s., 1H), 8.60 (d, J=8.3 Hz, 1H), 7.64 (s, 1H), 6.98-7.09 (m, 3H), 6.33 (br. s., 1H), 4.51 (q, J=7.0 Hz, 2H), 3.93 (s, 3H), 2.60-2.85 (m, 1H), 2.51-2.55 (m, 4H), 2.19 (s, 3H), 1.40 (t, J=7.0 Hz, 3H), 0.86-1.10 (m, 3H).

Example 42

(4-((4-ethoxy-7H-pyrrolo-[2,3-d]-pyrimidin-2-yl)amino)-3-methoxyphenyl)(4-(methoxymethyl)piperidin-1-yl)methanone (E42)

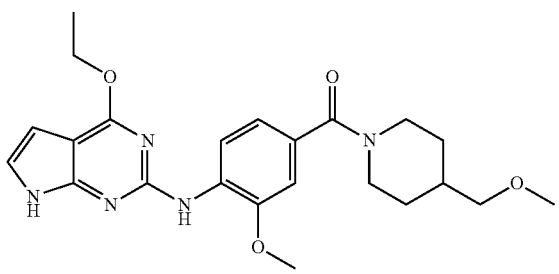 [SMILES: CCOc1nc(Nc2ccc(C(=O)N3CCC(COC)CC3)cc2OC)nc2[nH]ccc12]

A solution of (4-((4-ethoxy-7-tosyl-1-pyrrolo[2,3-d]pyrimidin-2-yl)amino)-3-methoxyphenyl)(4-(methoxymethyl)piperidin-1-yl)methanone (which can be prepared according to D127) (220 mg, 0.371 mmol) and sodium hydroxide (4 mL, 8.00 mmol, 2M in water) in isopropanol (5 mL) was stirred overnight under 60° C. The mixture was concentrated and 2N HCl was added until pH=7. The mixture was then extracted with EA. The organic layer was dried and concentrated. The crude was purified by prep-HPLC to give the title compound E42 (45 mg, 0.102 mmol, 27.6% yield) as a white solid.

LCMS: 440[M+H]$^+$. $t_R$=1.383. (LCMS condition 2)

$^1$H NMR (400 MHz, DMSO-d$_6$): δ 11.58 (br. s., 1H), 8.59 (d, J=8.3 Hz, 1H), 7.63 (s, 1H), 6.95-7.09 (m, 3H), 6.33 (d, J=3.0 Hz, 1H), 4.51 (q, J=6.9 Hz, 2H), 3.93 (s, 3H), 3.34 (s, 2H), 3.24 (s, 3H), 3.21 (d, J=6.0 Hz, 2H), 2.67-3.11 (m, 2H), 1.58-1.92 (m, 3H), 1.40 (t, J=7.0 Hz, 3H), 0.96-1.27 (m, 2H).

Example 43

(S)-(4-((4-ethoxy-7H-pyrrolo-[2,3-d]-pyrimidin-2-yl)amino)-3-methoxyphenyl)(2-(methoxymethyl)pyrrolidin-1-yl)methanone (E43)

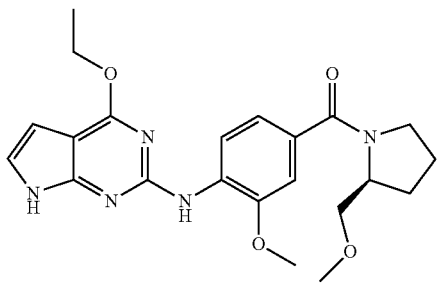 [SMILES: CCOc1nc(Nc2ccc(C(=O)N3CCC[C@H]3COC)cc2OC)nc2[nH]ccc12]

A solution of (S)-(4-((4-ethoxy-7-tosyl-7H-pyrrolo[2,3-d]pyrimidin-2-yl)amino)-3-methoxyphenyl)(2-(methoxymethyl)pyrrolidin-1-yl)methanone (which can be prepared according to D126) (100 mg, 0.173 mmol) and sodium hydroxide (104 mg, 2.59 mmol) in isopropanol (5.0 mL) and water (5.0 mL) was stirred under 60° C. for 4 hours. The mixture was diluted with EA and washed with water. The organic layer was dried and concentrated. The crude was purified via reversed chromatography (Biotage SNAP Cartridge, KP-C18-HS 120 g, 5%~95% MeCN/H$_2$O, 0.05% ammonia) to give the title compound E43 (41 mg, 0.096 mmol, 55.9% yield) as a yellow solid.

LCMS: 426[M+H]$^+$. t$_R$=3.213. (LCMS condition 1)

$^1$H NMR (400 MHz, CHLOROFORM-d): δ 8.52-8.81 (m, 2H), 7.64 (s, 1H), 7.12-7.23 (m, 2H), 6.70-6.95 (m, 1H), 6.29-6.55 (m, 1H), 4.58 (q, J=7.1 Hz, 2H), 4.34-4.53 (m, 1H), 3.95 (s, 3H), 3.52-3.77 (m, 4H), 3.40 (s, 3H), 2.03-2.14 (m, 1H), 1.90-2.03 (m, 2H), 1.75-1.82 (m, 1H), 1.49 (t, J=7.1 Hz, 3H).

Example 44

(4-((4-ethoxy-7H-pyrrolo-[2,3-d]pyrimidin-2-yl)amino)-3-methoxyphenyl)(2-oxa-6-azaspiro-[3.5]nonan-6-yl)methanone (E44)

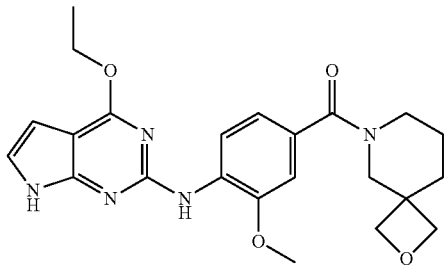 [SMILES: CCOc1nc(Nc2ccc(C(=O)N3CCCC4(COC4)C3)cc2OC)nc2[nH]ccc12]

A solution of (4-((4-ethoxy-7-tosyl-7H-pyrrolo[2,3-d]pyrimidin-2-yl)amino)-3-methoxyphenyl)(2-oxa-6-azaspiro[3.5]nonan-6-yl)methanone (which can be prepared according to D129) (150 mg, 0.254 mmol) and sodium hydroxide (0.254 mL, 0.507 mmol, 2M in water) in THF (10 mL) was stirred at 60° C. for 18 hours. The reaction mixture was poured into EtOAc (20 mL) and extracted with water (3×30 mL). The organic layer was evaporated in vacuum and purified by prep-HPLC to give the title compound E44 (30 mg, 0.069 mmol, 27.0% yield) as a white solid.

LCMS: 437.8[M+H]$^+$. t$_R$=1.396. (LCMS condition 2)

$^1$H NMR (400 MHz, CHLOROFORM-d): δ 9.20-9.45 (m, 1H), 8.65 (d, J=8.3 Hz, 1H), 7.63 (s, 1H), 6.93-7.06 (m, 2H), 6.81 (d, J=2.0 Hz, 1H), 6.44 (br. s., 1H), 4.58 (q, J=7.0 Hz, 2H), 4.24-4.50 (m, 4H), 3.94 (s, 3H), 3.74-3.90 (m, 2H), 3.52 (br. s., 2H), 1.89-1.95 (m, 2H), 1.56 (br. s., 2H), 1.49 (t, J=7.0 Hz, 3H).

Example 45

(±)-(4-((4-ethoxy-7H-pyrrolo-[2,3-d]-pyrimidin-2-yl)amino)-3-methoxyphenyl)(1-(hydroxymethyl)-3-azabicyclo-[3.1.0]-hexan-3-yl)methanone (E45)

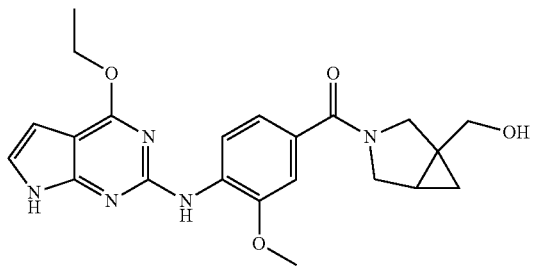 [SMILES: CCOc1nc(Nc2ccc(C(=O)N3CC4CC4(CO)C3)cc2OC)nc2[nH]ccc12]

A solution of (4-((4-ethoxy-7-tosyl-7H-pyrrolo[2,3-d]pyrimidin-2-yl)amino)-3-methoxyphenyl)(1-(hydroxymethyl)-3-azabicyclo[3.1.0]hexan-3-yl)methanone (which can be prepared according to D128) (110 mg, 0.190 mmol) and sodium hydroxide (114 mg, 2.86 mmol) in isopropanol (5 mL) and water (5.00 mL) was stirred at 60° C. for 4 hours. The mixture was diluted with EA, washed with water. The organic layer was dried and concentrated. The crude was purified via reversed chromatography (Biotage SNAP Cartridge, KP-C18-HS 120 g, 5%~95% MeCN/H$_2$O, 0.05% ammonia) to give the title compound E45 (71 mg, 0.168 mmol, 88% yield) as a yellow solid.

LCMS: 424[M+H]$^+$. t$_R$=2.737. (LCMS condition 1)

$^1$H NMR (400 MHz, CHLOROFORM-d): δ 8.57 (d, J=8.8 Hz, 2H), 7.56 (s, 1H), 7.02 (s, 2H), 6.75-6.84 (m, 1H), 6.33-6.42 (m, 1H), 4.51 (q, J=7.1 Hz, 2H), 4.11-4.30 (m, 1H), 3.87 (s, 3H), 3.37-3.79 (m, 5H), 1.38-1.47 (m, 4H), 0.71 (d, J=5.4 Hz, 1H), 0.42 (t, J=4.6 Hz, 1H).

Example 46 and 47

Enantiomer 1: (4-((4-ethoxy-7H-pyrrolo-[2,3-d]-pyrimidin-2-yl)amino)-3-methoxyphenyl)(1-(hydroxymethyl)-3-azabicyclo-[3.1.0]-hexan-3-yl)methanone (E46)

Enantiomer 2: (4-((4-ethoxy-7H-pyrrolo-[2,3-d]-pyrimidin-2-yl)amino)-3-methoxyphenyl)(1-(hydroxymethyl)-3-azabicyclo-[3.1.0]-hexan-3-yl)methanone (E47)

E46

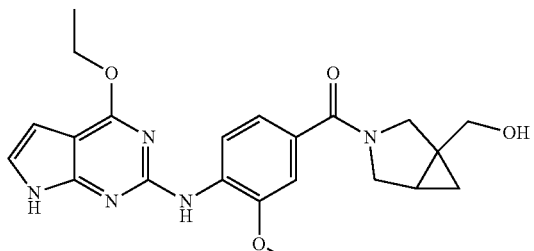

enantiomer1

-continued

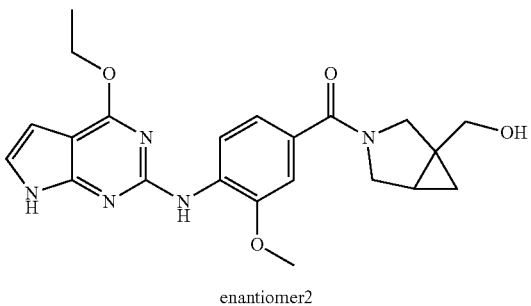

enantiomer2

The title compounds E46 (18.0 mg, 30.0% yield) and E47 (20.0 mg, 33.3% yield) were afforded by chiral-separation of E45 as gray solids. (Chiral-HPLC: Co-Solvent: MeOH; Column AS-H (4.6*250 mm, 5 um); Mobile Phase: n-Hexane (0.1% DEA): EtOH (0.1% DEA)=80:20; Flow: 1.0 ml/min; Temperature: 40; Wavelength: 214 nm&254 nm)

E46: LCMS: 424[M+H]$^+$. $t_R$=1.18 mins. (LCMS condition 2)

Chiral HPLC: $t_R$=12.863 mins. (Conditions: Column AS-H (4.6*250 mm, 5 um); Mobile Phase: n-Hexane (0.1% DEA): EtOH (0.1% DEA)=80:20) Single unknown absolute stereochemistry $^1$H NMR (400 MHz, DMSO-d$_6$): δ 11.56 (1H, s), 8.58 (d, J=10.5 Hz, 1H), 7.61 (s, 1H), 7.04 (m, 3H), 6.32 (m, 1H), 4.63 (m, 1H), 4.49 (dd, J=10.0 Hz, 2H), 4.01 (m, 4H), 3.96 (m, 1H), 3.50 (m, 2H), 3.41 (m, 2H), 1.39 (t. J=10.0 Hz, 4H), 0.71 (m, 1H), 0.27 (m, 1H).

E47: LCMS: 424 [M+H]$^+$. $t_R$=1.18 mins. (LCMS condition 2)

Chiral HPLC: $t_R$=16.540 mins. (Conditions: Column AS-H (4.6*250 mm, 5 um); Mobile Phase: n-Hexane (0.1% DEA): EtOH (0.1% DEA)=80:20) Single unknown absolute stereochemistry $^1$H NMR (400 MHz, DMSO-d$_6$): δ 11.56 (s, 1H), 8.58 (d, J=10.5 Hz, 1H), 7.61 (s, 1H), 7.07 (m, 3H), 6.32 (m, 1H), 4.64 (m, 1H), 4.49 (dd, J=10.0 Hz, 2H), 3.91 (m, 4H), 3.76 (m, 1H), 3.50 (m, 2H), 3.43 (m, 2H), 1.39 (t, J=10.0 Hz, 4H), 0.71 (m, 1H), 0.27 (m, 1H).

Example 48

(±)-(4-((4-ethoxy-7H-pyrrolo-[2,3-d]-pyrimidin-2-yl)amino)-3-methoxyphenyl)(5-(hydroxymethyl)-6-azaspiro-[2.5]-octan-6-yl)methanone (E48)

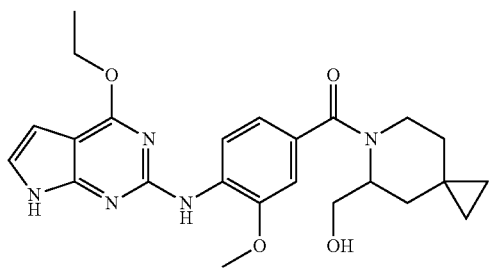 [SMILES: CCOc1nc(Nc2ccc(C(=O)N3CCC4(CC4)CC3CO)cc2OC)nc2[nH]ccc12]

To a solution of 4-((4-ethoxy-7H-pyrrolo-[2,3-d]-pyrimidin-2-yl)amino)-3-methoxybenzoic acid (D129) (which can be prepared according to D130 (58.1 mg, 0.177 mmol) and 6-azaspiro-[2.5]-octan-5-ylmethanol (which can be prepared according to D48) (25 mg, 0.177 mmol) in DMF (2.0 mL) was added DIPEA (68.6 mg, 0.531 mmol) and HATU (135 mg, 0.354 mmol). The reaction was stirred at room temperature for 2 hours. The mixture was diluted with water and extracted with DCM (20 mL×3). The combined organic layer was dried over Na$_2$SO$_4$, filtered and concentrated in vacuum. The crude was purified by column chromatography on silica gel (DCM:MeOH=20:1) to give the title compound E48 (58 mg, 0.128 mmol, 72.6% yield) as a white solid.

LCMS: 452[M+H]$^+$. $t_R$=1.44. (LCMS condition 2)

$^1$HNMR (400 MHz, DMSO-d$_6$): δ 11.55 (s, 1H), 8.56 (d, J=10.5 Hz, 1H), 7.59 (s, 1H), 7.04 (m, 3H), 6.31 (s, 1H), 4.78 (s, 1H), 4.50 (dd, J=9.0 Hz, 2H), 3.91 (s, 3H), 3.77 (s, 1H), 3.59 (s, 1H), 3.01 (s, 1H), 1.85 (m, 2H), 1.38 (t, J=9.0 Hz, 3H), 1.04 (s, 1H), 0.86 (s, 1H), 0.40 (m, 2H), 0.22 (m, 2H).

Example 49 and 50

Enantiomer 1: (4-((4-ethoxy-7H-pyrrolo-[2,3-d]-pyrimidin-2-yl)amino)-3-methoxyphenyl)(5-(hydroxymethyl)-6-azaspiro[2.5]octan-6-yl)methanone (E49)

Enantiomer 2: (4-((4-ethoxy-7H-pyrrolo-[2,3-d]-pyrimidin-2-yl)amino)-3-methoxyphenyl)(5-(hydroxymethyl)-6-azaspiro[2.5]octan-6-yl)methanone (E50)

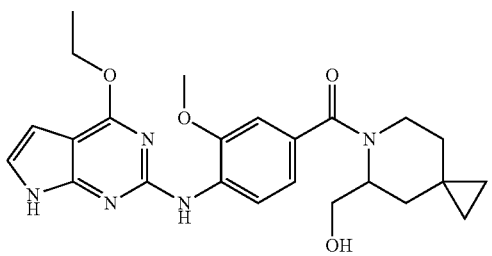

enantiomer1

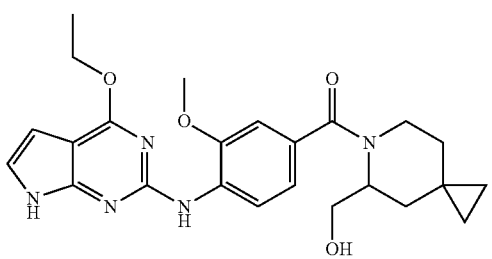

enantiomer 2

The title compounds E49 (7.0 mg, 14.0% yield) and E50 (7.0 mg, 14.0% yield) were afforded by chiral-separation of E48 as white solids. (Chiral-HPLC: Co-Solvent: MeOH; Column IC (4.6*250 mm, 5 um); Column Temperature 38.3; CO$_2$ Flow Rate 1.95; Co-Solvent Flow Rate 1.05; Co-Solvent % 35; Back Pressure 118; Total Flow 3; PDA Start Wavelength 214; PDA Stop Wavelength 359).

E49: LCMS: 452[M+H]$^+$. $t_R$=1.31 mins. (LCMS condition 2)

Chiral HPLC: $t_R$=8.37 mins. (Conditions: IC (4.6*250 mm, 5 um); Co-Solvent: MeOH; Co-Solvent: 35%) Single unknown absolute stereochemistry $^1$H NMR (400 MHz, CHLOROFORM-d): δ 7.12 (m, 2H), 6.90 (s, 1H), 6.48 (s, 1H), 4.64 (dd, J=10.0 Hz, 2H), 4.13 (s, 1H), 3.95 (s, 3H), 3.75 (s, 1H), 3.20 (s, 1H), 2.12 (m, 2H), 1.51 (t, 3H, J=10.0 Hz), 1.07 (m, 1H), 0.92 (m, 1H), 0.38 (m, 4H).

E50: LCMS: 452[M+H]$^+$. $t_R$=1.31 mins. (LCMS condition 2)

Chiral HPLC: $t_R$=6.66 mins. (Conditions: IC (4.6*250 mm, 5 um); Co-Solvent: MeOH; Co-Solvent: 35%) Single unknown absolute stereochemistry $^1$H NMR (400 MHz, CHLOROFORM-d): δ 7.91 (s, 1H), 7.12 (m, 2H), 6.90 (s, 1H), 6.48 (s, 1H), 4.62 (dd, J=10.0 Hz, 2H), 4.16 (s, 1H), 3.96 (s, 3H), 3.76 (s, 1H), 3.25 (s, 1H), 2.11 (m, 1H), 2.03 (m, 1H), 1.51 (t, J=10.0 Hz, 3H), 1.07 (m, 1H), 0.91 (m, 1H), 0.40 (m, 4H).

Example 51

(4-((4-ethoxy-7H-pyrrolo-[2,3-d]-pyrimidin-2-yl)amino)-3-methoxyphenyl)(2,7-diazaspiro-[3.5]nonan-7-yl)methanone (E51)

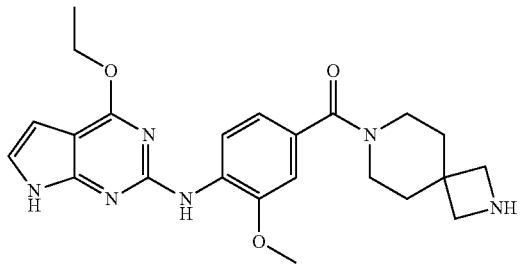 [SMILES: CCOc1nc(Nc2ccc(C(=O)N3CCC4(CC3)CNC4)cc2OC)nc2[nH]ccc12]

A solution of tert-butyl-7-(4-((4-ethoxy-7H-pyrrolo-[2,3-d]-pyrimidin-2-yl)amino)-3-methoxybenzoyl)-2, 7-diazaspiro-[3.5]-nonane-2-carboxylate (which can be prepared according to D131) (142 mg, 0.265 mmol) in DCM (10 mL) was added with TFA (0.102 mL, 1.323 mmol) slowly at room temperature. The reaction was stirred overnight at room temperature. The mixture was then concentrated and the residue was re-dissolved in methanol, adjusted the pH=9 with ammonia solution and purified by reverse phase chromatography (Biotage SNAP Cartridge, KP-C18-HS 120 g, 5%~95% MeCN/H$_2$O, 0.05% ammonia) to give the title compound E51 (63 mg, 0.137 mmol, 51.8% yield) as a white solid.

LCMS: 437.8[M+H]$^+$. $t_R$=2.00. (LCMS condition 1)

$^1$H NMR (400 MHz, DMSO-d$_6$): δ 11.28-11.65 (m, 1H), 8.52 (d, J=8.3 Hz, 1H), 7.55 (s, 1H), 6.88-7.00 (m, 3H), 6.26 (d, J=3.4 Hz, 1H), 4.44 (q, J=7.1 Hz, 2H), 3.85 (s, 3H), 3.25-3.53 (m, 8H), 1.64 (br. s., 4H), 1.33 (t, J=7.0 Hz, 3H).

Example 52 and 53

Enantiomer 1: (4-((4-ethoxy-7H-pyrrolo-[2,3-d]-pyrimidin-2-yl)amino)-3-methoxyphenyl)(1-(methoxymethyl)-6-azaspiro-[2.5]-octan-6-yl)methanone (E52)

Enantiomer 2: (4-((4-ethoxy-7H-pyrrolo-[2,3-d]-pyrimidin-2-yl)amino)-3-methoxyphenyl)(1-(methoxymethyl)-6-azaspiro-[2.5]-octan-6-yl)methanone (E53)

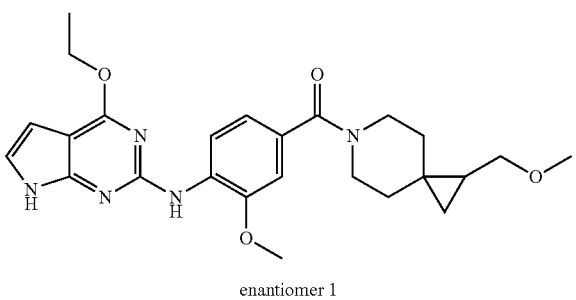

enantiomer 1

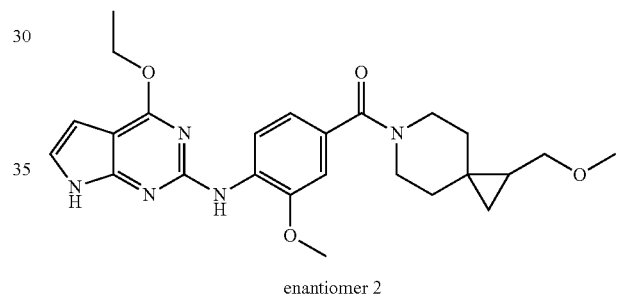

enantiomer 2

To a solution of (4-((4-ethoxy-7-tosyl-7H-pyrrolo[2,3-d]pyrimidin-2-yl)amino)-3-methoxyphenyl)(1-(methoxymethyl)-6-azaspiro[2.5]octan-6-yl)methanone (which can be prepared according to D119) (170 mg, 0.274 mmol) in THF (5 mL) was added sodium hydroxide (0.274 mL, 0.549 mmol, 2M in water). The reaction mixture was stirred at 50° C. for 1 hour. The reaction mixture was poured into EtOAc (20 mL) and extracted with water (3×30 mL). The organic layer was evaporated in vacuum to give the crude, which was purified by chiral-HPLC to give the title compound E52 (30 mg, 0.064 mmol, 23.49% yield) and E53 (30 mg, 0.064 mmol, 23.49% yield) as white solids. (Chiral-HPLC Co-Solvent: MeOH; Column IC (4.6*250 mm, 5 um); Column Temperature 39.1; CO$_2$ Flow Rate 2.25; Co-Solvent Flow Rate 0.75; Co-Solvent % 25; Back Pressure 119; Total Flow 3; PDA Start Wavelength 214; PDA Stop Wavelength 359).

E52: LCMS: 466[M+H]$^+$. (LCMS condition 2)

$t_R$=1.49 mins. Chiral HPLC: $t_R$=5.66 mins. (Conditions: IC (4.6*250 mm, 5 um); Co-Solvent: MeOH; Co-Solvent: 25%). Single unknown absolute stereochemistry $^1$H NMR (400 MHz, CHLOROFORM-d): δ 8.65 (d, J=8.3 Hz, 1H), 8.38 (br. s., 1H), 7.61 (s, 1H), 6.96-7.09 (m, 2H), 6.87 (dd, J=3.3, 2.0 Hz, 1H), 6.26-6.62 (m, 1H), 4.58 (q, J=7.0 Hz, 2H), 3.95 (s, 3H), 3.42-3.83 (m, 3H), 3.35 (s, 3H), 3.25 (t, J=9.5 Hz, 1H), 1.40-1.57 (m, 9H), 1.03 (br. s., 1H), 0.63 (dd, J=8.5, 4.8 Hz, 1H), 0.29 (t, J=4.8 Hz, 1H).

E53: LCMS: 466[M+H]⁺. $t_R$=1.49 mins. (LCMS condition 2)

Chiral HPLC: $t_R$=7.89 mins. (Conditions: IC (4.6*250 mm, 5 um); Co-Solvent: MeOH; Co-Solvent: 35%). Single unknown absolute stereochemistry ¹H NMR (400 MHz, CHLOROFORM-d): δ 8.65 (d, J=8.3 Hz, 1H), 8.43 (br. s., 1H), 7.61 (s, 1H), 6.93-7.14 (m, 2H), 6.86 (dd, J=3.3, 2.0 Hz, 1H), 6.32-6.56 (m, 1H), 4.58 (q, J=7.0 Hz, 2H), 3.95 (s, 3H), 3.53 (dd, 3H), 3.35 (s, 3H), 3.25 (t, J=9.4 Hz, 1H), 1.21-1.57 (m, 9H), 0.97-1.11 (m, 1H), 0.63 (dd, J=8.4, 4.6 Hz, 1H), 0.29 (t, J=4.9 Hz, 1H).

Example 54

(R)-(4-((4-(cyclopropylmethoxy)-5-methyl-7H-pyrrolo-[2,3-d]-pyrimidin-2-yl)amino)-3-methoxyphenyl)(2,4-dimethylpiperazin-1-yl)methanone (E54)

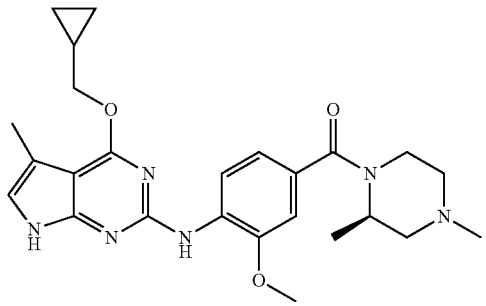 [SMILES: COc1cc(C(=O)N2CCN(C)C[C@H]2C)ccc1Nc1nc(OCC2CC2)c2c(C)c[nH]c2n1]

A solution of (R)-(4-((4-(cyclopropylmethoxy)-5-methyl-7-tosyl-7H-pyrrolo[2,3-d]pyrimidin-2-yl)amino)-3-methoxyphenyl)(2,4-dimethylpiperazin-1-yl)methanone (which can be prepared according to D120) (20 mg, 0.032 mmol), sodium hydroxide (2 mL, 4.00 mmol, 2M in water) in isopropanol (2 mL) was stirred overnight at 60° C. The mixture was concentrated and 2N HCl was added until pH=7. The mixture was then extracted with EA. The organic layer was dried and concentrated. The crude was purified by prep-HPLC to give the title compound E54 (5 mg, 10.76 μmol, 33.3% yield) as a white solid.

LCMS: 465[M+H]⁺. $t_R$=1.582. (LCMS condition 2)

¹H NMR (400 MHz, DMSO-d₆): δ 11.16 (br. s., 1H), 8.55 (d, J=8.0 Hz, 1H), 7.56 (s, 1H), 6.92-7.00 (m, 2H), 6.74 (s, 1H), 4.29 (d, J=7.0 Hz, 2H), 3.90 (s, 3H), 3.69 (m, 1H), 3.10-3.23 (m, 1H), 2.56-2.77 (m, 3H), 2.26 (s, 3H), 2.15 (s, 3H), 2.02 (dd, J=11.3, 3.5 Hz, 1H), 1.75-1.91 (m, 1H), 1.23-1.30 (m, 4H), 0.49-0.62 (m, 2H), 0.32-0.43 (m, 2H).

Example 55

(4-((4-(cyclopropylmethoxy)-5-methyl-7H-pyrrolo-[2,3-d]-pyrimidin-2-yl)amino)-3-methoxyphenyl)(4-methylpiperazin-1-yl)methanone (E55)

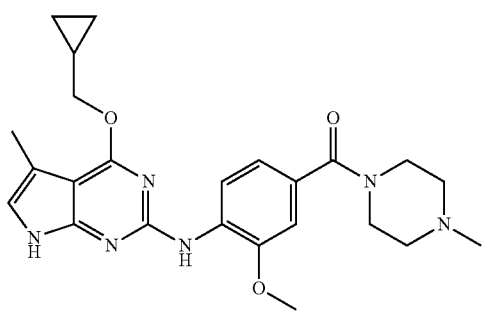 [SMILES: COc1cc(C(=O)N2CCN(C)CC2)ccc1Nc1nc(OCC2CC2)c2c(C)c[nH]c2n1]

A solution of (4-((4-(cyclopropylmethoxy)-5-methyl-7-tosyl-7H-pyrrolo[2,3-d]pyrimidin-2-yl)amino)-3-methoxyphenyl)(4-methylpiperazin-1-yl)methanone (which can be prepared according to D121) (30 mg, 0.050 mmol) and sodium hydroxide (2 mL, 4.00 mmol, 2M in water) in isopropanol (2 mL) was stirred overnight at 60° C. The mixture was concentrated and 2N HCl was added until pH=7. The mixture was then extracted with EA. The organic layer was dried and concentrated. The crude was purified by prep-HPLC to give the title compound E55 (3 mg, 6.66 μmol, 13.42% yield) as a white solid.

LCMS: 451 [M+H]⁺. $t_R$=1.511. (LCMS condition 2)

¹H NMR (400 MHz, DMSO-d₆): δ 11.17 (br. s., 1H), 8.58 (d, J=8.3 Hz, 1H), 7.57 (s, 1H), 6.97-7.05 (m, 1H), 6.76 (s, 1H), 4.30 (d, J=6.8 Hz, 2H), 3.92 (s, 3H), 3.53 (br. s., 4H), 2.33 (br. s., 4H), 2.28 (s, 3H), 2.20 (s, 3H), 0.79-0.89 (m, 1H), 0.53-0.63 (m, 2H), 0.40 (q, J=4.8 Hz, 2H).

Example 56

(4-((4-ethoxy-1H-pyrazolo-[3,4-d]-pyrimidin-6-yl)amino)-3-methoxyphenyl)(morpholino)methanone (E56)

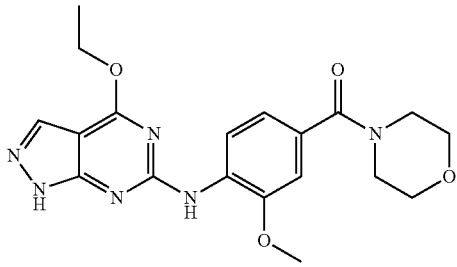 [SMILES: CCOc1nc(Nc2ccc(C(=O)N3CCOCC3)cc2OC)nc2[nH]ncc12]

A solution of 6-chloro-4-ethoxy-1H-pyrazolo-[3,4-d]-pyrimidine (which can be prepared according to D91) (180 mg, 0.906 mmol), (4-amino-3-methoxyphenyl)(morpholino)methanone (278 mg, 1.178 mmol), Pd₂(dba)₃ (41.5 mg, 0.045 mmol), potassium carbonate (376 mg, 2.72 mmol) and dicyclohexyl(2',4',6'-triisopropyl-[1,1'-biphenyl]-2-yl)phosphine (43.2 mg, 0.091 mmol) was irradiated by microwave at 120° C. for 1 hour. After filtration, the filtrate was concentrated and purified by MDAP (basic mobile phase) to give the title compound E56 as a white solid. Yield: 26.3%.

LCMS: 399[M+H]⁺. $t_R$=2.687. (LCMS condition 1)

¹H NMR (400 MHz, METHANOL-d₄): δ 8.62 (d, J=8.3 Hz, 1H), 7.80 (s, 1H), 6.89-7.04 (m, 2H), 4.51 (q, J=6.9 Hz, 3H), 3.89 (s, 3H), 3.61 (br. s., 8H), 1.39 (t, 3H).

Example 57

(4-((4-ethoxy-3-methyl-1H-pyrazolo-[3,4-d]-pyrimidin-6-yl)amino)-3-methoxyphenyl)(morpholino)methanone (E57)

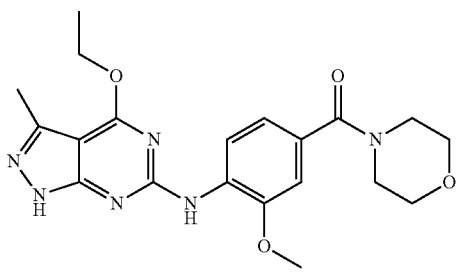 [SMILES: CCOc1nc(Nc2ccc(C(=O)N3CCOCC3)cc2OC)nc2[nH]nc(C)c12]

A solution of 6-chloro-4-ethoxy-3-methyl-1H-pyrazolo[3,4-d]pyrimidine (which can be prepared according to D92) (100 mg, 0.470 mmol), (4-amino-3-methoxyphenyl)(morpholino)methanone (111 mg, 0.470 mmol), Pd₂(dba)₃ (33 mg, 0.036 mmol), dicyclohexyl(2',4',6'-triisopropyl-[1,1'-biphenyl]-2-yl) phosphine (35 mg, 0.073 mmol) and potassium carbonate (195 mg, 1.411 mmol) in 2-butanol (12 mL) was irradiated by microwave at 120° C. for 1 hour. After filtration, the filtrate was concentrated and purified by MDAP (basic mobile phase) to give the title compound E57 (25 mg, 0.061 mmol, 12.89% yield) as a white solid.

LCMS: 413[M+H]⁺. $t_R$=2.717. (LCMS condition 1)

¹H NMR (400 MHz, METHANOL-d₄): δ 8.57 (s, 1H), 6.75-7.08 (m, 2H), 4.32-4.56 (m, 2H), 3.87 (s, 3H), 3.60 (br. s., 8H), 2.37 (s, 3H), 1.37 (m, 3H).

Example 58

(4-((4-(cyclopropylmethoxy)-1H-pyrazolo-[3,4-d]pyrimidin-6-yl)amino)-3-methoxyphenyl)(morpholino)methanone (E58)

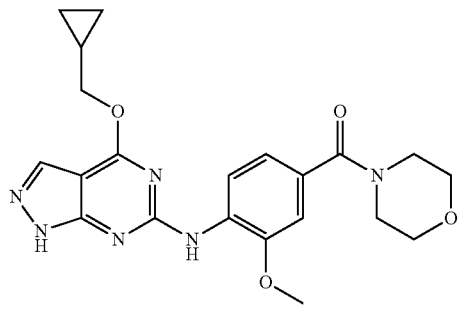 [SMILES: COc1cc(C(=O)N2CCOCC2)ccc1Nc1nc(OCC2CC2)c2cn[nH]c2n1]

A solution of 6-chloro-4-(cyclopropylmethoxy)-1H-pyrazolo[3,4-d]pyrimidine (which can be prepared according to D93) (100 mg, 0.445 mmol), (4-amino-3-methoxyphenyl)(morpholino)methanone (105 mg, 0.445 mmol), Pd₂(dba)₃ (20.38 mg, 0.022 mmol), potassium carbonate (185 mg, 1.335 mmol) and dicyclohexyl(2',4',6'-triisopropyl-[1,1'-biphenyl]-2-yl)phosphine (21.22 mg, 0.045 mmol) in 2-butanol (10 mL) was irradiated by microwave at 120° C. for 1 hour. After filtration, the filtrate was concentrated and purified by MDAP (basic mobile phase) to give the title compound E58 (20 mg, 0.047 mmol, 10.59% yield) as a white solid.

LCMS: 425[M+H]⁺. $t_R$=2.911. (LCMS condition 1)

¹H NMR (400 MHz, METHANOL-d₄): δ 8.56-8.65 (m, 1H), 7.83 (s, 1H), 6.90-7.04 (m, 2H), 4.22-4.33 (m, 2H), 4.00 (q, J=7.1 Hz, 2H), 3.90 (s, 3H), 3.61 (br. s., 8H), 1.24-1.36 (m, 1H), 1.14 (t, J=7.1 Hz, 3H), 0.50-0.62 (m, 1H), 0.23-0.40 (m, 2H).

Example 59

4-ethoxy-2-((2-methoxy-4-(morpholine-4-carbonyl)phenyl)amino)-7H-pyrrolo[2,3-d]pyrimidine-5-carbonitrile (E59)

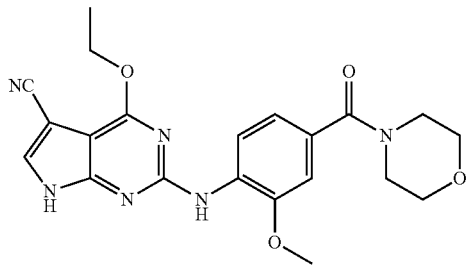 [SMILES: CCOc1nc(Nc2ccc(C(=O)N3CCOCC3)cc2OC)nc2[nH]cc(C#N)c12]

To 2-chloro-4-ethoxy-7H-pyrrolo[2,3-d]pyrimidine-5-carbonitrile (which can be prepared according to D94) (100 mg, 0.449 mmol), (9,9-dimethyl-9H-xanthene-4,5-diyl)bis(diphenylphosphine) (26.0 mg, 0.045 mmol), potassium carbonate (124 mg, 0.898 mmol) and Pd₂(dba)₃ (20.57 mg, 0.022 mmol) in 2-butanol (2 mL) was added (4-amino-3-methoxyphenyl)(morpholino)methanone (106 mg, 0.449 mmol). The mixture was irradiated by microwave at 120° C. for 45 min. The reaction mixture was poured into EtOAc (20 mL) and washed with water (3×30 mL). The organic layer was evaporated in vacuum and purified by prep-HPLC to give the title compound E59 (7 mg, 0.013 mmol, 2.95% yield) as a yellow solid.

LCMS: 423[M+H]⁺. $t_R$=1.722. (LCMS condition 3)

¹H NMR (400 MHz, CHLOROFORM-d): δ 9.14 (br. s., 1H), 8.58 (d, J=8.0 Hz, 1H), 7.70 (s, 1H), 7.41 (s, 1H), 6.97-7.10 (m, 2H), 4.61 (q, J=7.0 Hz, 2H), 3.95 (s, 3H), 3.72 (br. s., 8H), 1.52 (t, 3H).

Example 60

4-ethoxy-2-((2-isopropoxy-4-(morpholine-4-carbonyl)-phenyl)amino)-7H-pyrrlo-[2,3-d]-pyrimidine-5-carbonitrile (E60)

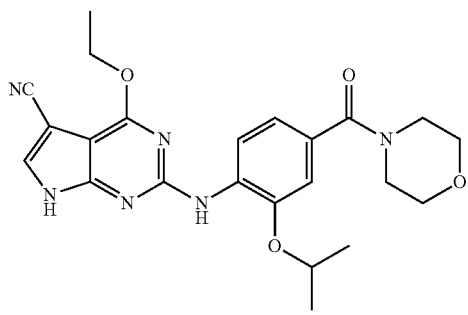 [SMILES: CCOc1nc(Nc2ccc(C(=O)N3CCOCC3)cc2OC(C)C)nc2[nH]cc(C#N)c12]

A solution of 2-chloro-4-ethoxy-7H-pyrrolo[2,3-d]pyrimidine-5-carbonitrile (which can be prepared according to D94) (50 mg, 0.225 mmol), (4-amino-3-isopropoxyphenyl)(morpholino)methanone (which can be prepared according to D68) (65.3 mg, 0.247 mmol), potassium carbonate (93 mg, 0.674 mmol), Pd₂(dba)₃ (10.28 mg, 0.011 mmol) and dicyclohexyl(2',4',6'-triisopropyl-[1,1'-biphenyl]-2-yl)phosphine (10.71 mg, 0.022 mmol) in 2-butanol (5 mL) was irradiated by microwave to 120° C. for 1 hour. After filtration, the filtrate was concentrated and purified by MDAP (basic mobile phase) to give the title compound E60 (9 mg, 0.020 mmol, 8.90% yield) as a white solid.

LCMS: 451[M+H]$^+$. $t_R$=3.089. (LCMS condition 1)

$^1$H NMR (400 MHz, DMSO-d$_6$): δ 8.41 (d, J=8.3 Hz, 1H), 7.96 (s, 1H), 7.75 (s, 1H), 7.02 (s, 1H), 6.95 (d, J=8.3 Hz, 1H), 4.60-4.74 (m, 1H), 4.50 (q, J=7.1 Hz, 2H), 3.50-3.56 (m, 8H), 1.35 (t, J=7.0 Hz, 3H), 1.28 (d, J=6.1 Hz, 6H).

Example 61

4-ethoxy-2-((2-isopropoxy-4-(4-methylpiperazine-1-carbonyl)-phenyl)-amino)-7H-pyrrolo-[2,3-d]pyrimidine-5-carbonitrile (E61)

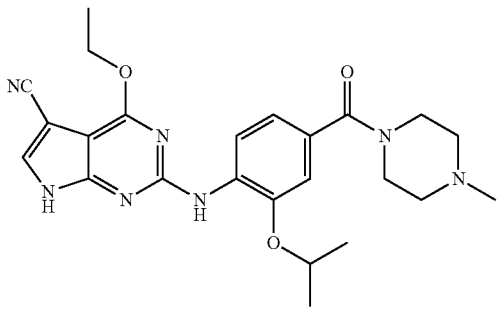 [SMILES: CCOc1nc(Nc2ccc(C(=O)N3CCN(C)CC3)cc2OC(C)C)nc2[nH]cc(C#N)c12]

A solution of 2-chloro-4-ethoxy-7H-pyrrolo[2,3-d]pyrimidine-5-carbonitrile (which can be prepared according to D94) (100 mg, 0.449 mmol), (4-amino-3-isopropoxyphenyl)(4-methylpiperazin-1-yl)methanone (which can be prepared according to D66) (137 mg, 0.494 mmol), potassium carbonate (186 mg, 1.348 mmol), Pd$_2$(dba)$_3$ (20.57 mg, 0.022 mmol) and dicyclohexyl(2',4',6'-triisopropyl-[1,1'-biphenyl]-2-yl)phosphine (21.41 mg, 0.045 mmol) in 2-butanol (5 mL) was irradiated by microwave at 120° C. for 1 hour. After filtration, the filtrate was concentrated and purified by MDAP (basic mobile phase) to give the title compound E61 (16 mg, 0.035 mmol, 7.68% yield) as a white solid.

LCMS: 464[M+H]$^+$. $t_R$=2.506. (LCMS condition 1)

$^1$H NMR (400 MHz, DMSO-d$_6$): δ 8.49 (d, 1H), 7.98 (s, 1H), 7.76 (s, 1H), 7.04 (s, 1H), 6.98 (d, 1H), 4.73 (m, 1H), 4.55 (q, 2H), 3.50 (m, 4H), 2.32 (m, 4H), 2.19 (s, 3H), 1.41 (t, 3H), 1.34 (d, 6H).

Example 62

(4-((4-ethoxy-5-(trifluoromethyl)-7H-pyrrolo-[2,3-d]-pyrimidin-2-yl)amino)-3-methoxyphenyl)(morpholino)methanone (E62)

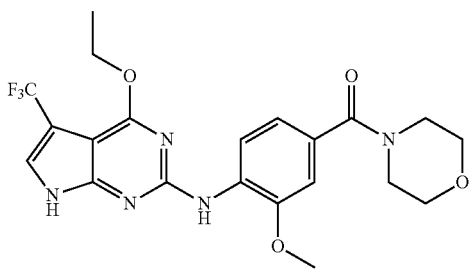 [SMILES: CCOc1nc(Nc2ccc(C(=O)N3CCOCC3)cc2OC)nc2[nH]cc(C(F)(F)F)c12]

A solution of 2-chloro-4-ethoxy-5-(trifluoromethyl)-7H-pyrrolo[2,3-d]pyrimidine (which can be prepared according to D95) (50 mg, 0.188 mmol), (4-amino-3-methoxyphenyl)(morpholino)methanone (66.7 mg, 0.282 mmol), dicyclohexyl(2',4',6'-triisopropyl-[1,1'-biphenyl]-2-yl)phosphine (17.95 mg, 0.038 mmol), potassium carbonate (78 mg, 0.565 mmol) and Pd$_2$(dba)$_3$ (17.24 mg, 0.019 mmol) in 1,4-dioxane (10 mL) under nitrogen was stirred at 120° C. for 1 hour. After cooled to room temperature, water (30 mL) was added and the mixture was extracted with EA (15 mL×3). The combined organic phase was washed with brine and then dried over Na$_2$SO$_4$. After filtration and concentration, the crude was purified by column chromatography on silica gel (DCM:MeOH=4:1) and further purified by MDAP (basic mobile phase) to give the title compound E62 (4.2 mg, 9.02 μmol, 4.79% yield) as a white solid.

LCMS: 466[M+H]$^+$. $t_R$=3.555. (LCMS condition 1)

$^1$H NMR (400 MHz, DMSO-d$_6$): δ 12.24 (br. s., 1H), 8.49 (d, J=8.3 Hz, 1H), 7.85 (s, 1H), 7.67 (s, 1H), 7.08 (s, 1H), 7.04 (d, J=8.3 Hz, 1H), 4.51 (q, J=6.9 Hz, 2H), 3.92 (s, 3H), 3.61 (br. s., 4H), 3.47-3.57 (m, 4H), 1.37 (t, 3H).

Example 63

4-ethoxy-2-((4-(4-fluoropiperidine-1-carbonyl)-2-methoxyphenyl)-amino)-7H-pyrrolo-[2,3-d]pyrimidine-5-carbonitrile (E63)

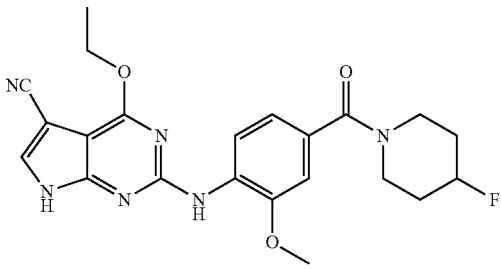 [SMILES: CCOc1nc(Nc2ccc(C(=O)N3CCC(F)CC3)cc2OC)nc2[nH]cc(C#N)c12]

A solution of 2-chloro-4-ethoxy-7H-pyrrolo-[2,3-d]-pyrimidine-5-carbonitrile (which can be prepared according to D94) (180 mg, 0.809 mmol), (4-amino-3-methoxyphenyl)(4-fluoropiperidin-1-yl)methanone ((which can be prepared according to D74) (245 mg, 0.970 mmol), potassium carbonate (335 mg, 2.426 mmol), Pd$_2$(dba)$_3$ (37.0 mg, 0.040 mmol) and dicyclohexyl(2',4',6'-triisopropyl-[1,1'-biphenyl]-2-yl)phosphine (38.5 mg, 0.081 mmol) in 2-butanol (5 mL) was irradiated by microwave at 120° C. for 4 hours. After filtration, the filtrate was concentrated and the crude was purified by reversed column chromatography (Biotage SNAP Cartridge, KP-C18-HS 120 g, 5%~95% MeCN/H$_2$O, 0.05% ammonia) to give the title compound E63 (42 mg, 0.096 mmol, 11.85% yield) as a white solid.

LCMS: 466[M+H]$^+$. $t_R$=3.315. (LCMS condition 1)

$^1$H NMR (400 MHz, DMSO-d$_6$): δ 12.29-12.63 (m, 1H), 8.34 (d, J=8.3 Hz, 1H), 7.94 (s, 1H), 7.85 (s, 1H), 7.01 (d, J=1.5 Hz, 1H), 6.96 (dd, J=1.5, 8.3 Hz, 1H), 4.73-4.97 (m, 1H), 4.48 (q, J=7.1 Hz, 2H), 3.85 (s, 3H), 3.30-3.63 (m, 4H), 1.57-1.95 (m, 4H), 1.34 (t, J=7.0 Hz, 3H).

Example 64 and 65

Enantiomer 1: (4-((4-ethoxy-7H-pyrrolo-[2,3-d]pyrimidin-2-yl)amino)-3-methoxyphenyl)-(1-(methoxymethyl)-3-azabicyclo[3.1.0]hexan-3-yl)methanone (E64)

Enantiomer 2: (4-((4-ethoxy-7H-pyrrolo-[2,3-d]pyrimidin-2-yl)amino)-3-methoxyphenyl)-(1-(methoxymethyl)-3-azabicyclo[3.1.0]hexan-3-yl)methanone (E65)

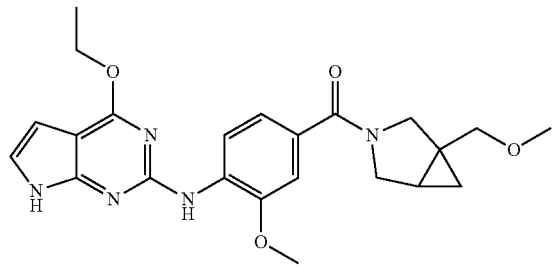

enantiomer 1

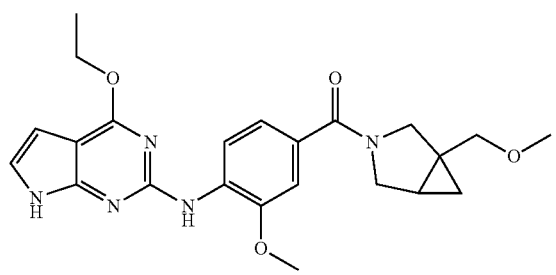

enantiomer 2

A solution of 2-chloro-4-ethoxy-7H-pyrrolo-[2,3-d]pyrimidine (which can be prepared according to D1) (103 mg, 0.521 mmol), (4-amino-3-methoxyphenyl)(1-(methoxymethyl)-3-azabicyclo-[3.1.0]hexan-3-yl)methanone (which can be prepared according to D134) (120 mg, 0.434 mmol), potassium carbonate (180 mg, 1.303 mmol), Pd$_2$(dba)$_3$ (19.88 mg, 0.022 mmol) and xantphos (21.53 mg, 0.045 mmol) in 2-butanol (6 mL) was irradiated by microwave at 120° C. for 45 min. After filtration, the filtrate was concentrated and the crude was purified MDAP (basic mobile phase) to get the racemic product, which was further purified by chiral-HPLC to give the title compound E64 (11 mg) and E65 (7 mg) as yellow solids. (Chiral-HPLC: Co-Solvent: MeOH; Column AD-H (4.6*250 mm, 5 um); Mobile Phase: n-Hexane (0.1% DEA): EtOH (0.1% DEA)=80:20; Flow: 1.0 ml/min; Temperature: 40; Wavelength: 214 nm & 254 nm)

E64: LCMS: 438[M+H]$^+$. t$_R$=1.32 mins. (LCMS condition 3)

Chiral HPLC: t$_R$=4.44 mins. (Conditions: Column AD-H (4.6*250 mm, 5 um); Mobile Phase: n-Hexane (0.1% DEA): EtOH (0.1% DEA)=80:20). Single unknown absolute stereochemistry $^1$H NMR (400 MHz, CHLOROFORM-d): δ 8.64 (d, J=8.3 Hz, 1H), 8.42 (br. s., 1H), 7.64 (s, 1H), 7.08 (s, 2H), 6.87 (dd, J=2.1, 3.4 Hz, 1H), 6.40-6.54 (m, 1H), 4.58 (q, J=7.0 Hz, 2H), 4.11-4.35 (m, 1H), 3.95 (s, 3H), 3.61-3.84 (m, 2H), 3.22-3.60 (m, 4H), 1.53-1.37 (m, 4H), 0.68-0.83 (m, 1H), 0.50 (t, J=4.4 Hz, 1H).

E65: LCMS: 438[M+H]$^+$. t$_R$=1.32 mins. (LCMS condition 3)

Chiral HPLC: t$_R$=6.15 mins. (Conditions: Column AD-H (4.6*250 mm, 5 um); Mobile Phase: n-Hexane (0.1% DEA): EtOH (0.1% DEA)=80:20). Single unknown absolute stereochemistry $^1$H NMR (400 MHz, CHLOROFORM-d): δ 8.64 (d, J=8.5 Hz, 1H), 8.43 (br. s., 1H), 7.63 (s, 1H), 7.04-7.13 (m, 2H), 6.87 (dd, J=2.3, 3.3 Hz, 1H), 6.42-6.51 (m, 1H), 4.58 (q, J=7.0 Hz, 2H), 4.15-4.36 (m, 1H), 3.94 (s, 3H), 3.28-3.82 (m, 8H), 1.36-1.53 (m, 4H), 0.67-0.85 (m, 1H), 0.50 (t, J=4.4 Hz, 1H).

Example 66

(1S,3S,5S)-2-(4-((4-ethoxy-7H-pyrrolo-[2,3-d]pyrimidin-2-yl)amino)-3-methoxybenzoyl)-2-azabicyclo-[3.1.0]-hexane-3-carbonitrile (E66)

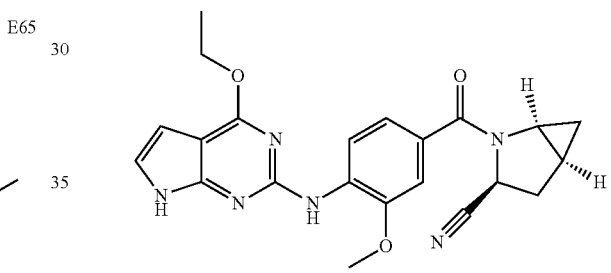

To a solution of 4-((4-ethoxy-7H-pyrrolo-[2,3-d]-pyrimidin-2-yl)amino)-1-methoxybenzoic acid (which can be prepared according to D129) (186 mg, 0.567 mmol), HATU (237 mg, 0.623 mmol) and DIPEA (0.297 mL, 1.700 mmol) in DMF (5 mL) was added (1S,3S,5S)-2-azabicyclo-[3.1.0]-hexane-3-carbonitrile hydrochloride (which can be prepared according to D136) (82 mg, 0.567 mmol). The mixture was stirred at room temperature for 5 hours. The solution was diluted with EA, washed with water. The organic layer was dried and concentrated. The crude was purified via MDAP (basic mobile phase) to give the title compound E66 (82.7 mg, 0.190 mmol, 33.5% yield) as an off-white solid.

LCMS: 419[M+H]$^+$. t$_R$=3.307 mins. (LCMS condition 1)

$^1$H NMR (400 MHz, DMSO-d$_6$): δ 11.63 (br. s., 1H), 8.73 (d, J=8.3 Hz, 1H), 7.72 (s, 1H), 7.30-7.47 (m, 2H), 7.02-7.10 (m, 1H), 6.35 (dd, J=1.8, 3.3 Hz, 1H), 5.34 (br. s., 1H), 4.47-4.59 (m, 2H), 3.98 (s, 3H), 3.62 (br. s., 1H), 2.60-2.72 (m, 1H), 2.27 (dd, J=2.9, 13.7 Hz, 1H), 1.87 (dd, J=5.7, 7.9 Hz, 1H), 1.41 (t, J=7.1 Hz, 3H), 1.13-1.05 (m, 1H), 0.89-0.98 (m, 1H).

F. BIOLOGICAL DATA

As stated above, the compounds of present invention are LRRK2 kinase inhibitors, and are useful in the treatment of diseases mediated by LRRK2. The biological activities of the compounds of present invention can be determined using any suitable assay for determining the activity of a candidate compound as a LRRK2 kinase inhibitor, as well as tissue and in vivo models.

Production of 6His-Tev-LRRK2 (1326-2527)

A LRRK2 cDNA encoding residues 1326-2527 was received from Dundee University (described in M. Jaleel et al., 2007, Biochem J, 405: 407-417). This gene fragment was subcloned into pFB-HTb (Invitrogen) using BamHI and NotI restriction sites. The LRRK2 plasmid was recombined into the baculovirus genome according to the BAC-to-BAC protocol described by Invitrogen. Transfection into *Spodoptera frugiperda* (Sf9) insect cells was performed using Cellfectin (Invitrogen), according to the manufacturer's protocol to generate P1 and P2 baculovirus stocks.

Sf9 cells were grown in HyClone SFX (Thermo Scientific) growth media at 27° C., 80 rpm in shake flask until of a sufficient volume to inoculate a bioreactor. The cells were grown in a 20 liter working volume Wave bioreactor (GE Healthcare) at 27° C., 50% dissolved oxygen and an agitation rate 22 rocks per minute, 10 degree rock angle, 200 ml/min air with a cell concentration of approximately 6×e6 cells/ml. The cells were infected with P2 Baculovirus at a multiplicity of infection (MOI) of 3. The cultivation was continued for a 48 hour expression phase. The infected cells were removed from the growth media by centrifugation at 2500 g using a Sorvall RC 3C Plus centrifuge at 2500 g for 20 minutes. The cell pellet was immediately frozen and subsequently supplied for purification.

A 260 g pellet was allowed to thaw in a water bath at 27° C. with 800 ml lysis buffer/buffer A (50 mm Tris-HCl pH 8.5, 300 mM NaCl, 1 mm DTT, 10% glycerol, 1 ml/L calbiochem complete protease inhibitor cocktail and benzonase (50 ul/800 ml)) before being dounce homogenised on ice using 20 strokes per 100 ml. The suspension was packed in ice and sonicated at 50% amplitude for 3 min 10 sec on/off using a ¾" probe. The suspension was then centrifuged at 100,000 g for 90 min, at 4° C.

The lysate (700 ml) was decanted from the insoluble pellet and contacted for 3 h at 4 C with 10 ml His bind Ni NTA resin by end over end mixing. The resin was recovered by centrifugation, 3000 g, 5 min at 4 C, and packed in an XK16 column. The column was then washed with 10 column volumes buffer A, 10 column volumes buffer B (buffer A+1M NaCl) and 10 column volumes buffer C (buffer A+20 mM imidazole). The column was then eluted with 15 column volumes buffer D (buffer A+300 mM imidazole) collecting 2 ml fractions. All washes and elution were conducted at 4 ml/min.

Fractions identified by SDS-PAGE as containing protein of interest were pooled and loaded directly onto a 320 ml SEC Superdex 200 pg column that was pre-equilibrated with buffer E (50 mM Tris-HCl pH 8.5, 300 mM NaCl, 10% glycerol, 1 mM DTT). The column was loaded and eluted with 1.2 column volumes buffer E at 2 ml/min collecting 2 ml fractions. Fractions identified by SDS-PAGE as containing protein of interest were tested for activity.

Production of Biotin-Longer LRRKtide

The peptide (biotin-RLGRDKYKTLRQIRQGNTKQR-OH) was assembled at a 0.2 mM scale using FMOC solid phase peptide synthesis on an ACT 357 MPS automated peptide synthesizer. The resulting crude peptide was cleaved from the resin using a 95:2.5:2.5 mix of trifluoroacetic acid:triisopropylsilane:water. The crude cleaved peptide was purified by reverse phase HPLC, eluting with a 5-35% gradient of 0.1% trifluoroacetic acid/acetonitrile in 0.1% trifluoroacetic acid/water.

Recombinant LRRK2 Enzyme Peptide Substrate TR-FRET Assay

This assay for LRRK2 inhibition is based on the detection of phosphorylation of the peptide 'longer LRRKtide' (biotin-RLGRDKYKTLRQIRQGNTKQR-OH) using a time resolved-fluorescence resonance energy transfer (TR-FRET) assay. It uses an antibody labelled europium chelate donor, W-1024 (Eu) and Streptavidin-Surelight APC acceptor (APC). When in close proximity, the excitation of Eu at 330 nm leads to energy transfer to APC with emission of light at 665 nm, Assay Protocol 1. A 10 mM test compound was dissolved in 100% DMSO and serially diluted 1 in 4. 100 nL was then added to a 384 well low volume black plate, excluding columns 6 and 18. 100 nL of DMSO was added to columns 6 and 18 as controls wells. Assay dilution gave a top final assay concentration of test compound of 166.67 µM 2. 3 uL of 'enzyme solution' containing 120 nM of purified recombinant 6HIS-Tev-LRRK2 (1326-2527) in assay buffer (50 mM Hepes (pH 7.2), 10 mM $MgCl_2$, 150 mM NaCl, 5% glycerol, 0.0025% triton X-100 and 1 mM DTT) was added to all wells except column 18 using a multidrop combi dispenser, giving a final assay concentration of 60 nM LRRK2 enzyme. 3 uL assay buffer only was added to column 18 using a multidrop combi dispenser as a 100% inhibition, no enzyme control. Column 6 (enzyme plus DMSO) gave 0% inhibition. Test plates were then incubated for 30 minutes at room temperature.

3. 3 uL 'substate solution' containing 2 uM Biotin-longer LRRKtide peptide substrate and 20 uM ATP was added to all wells of the plate using a multidrop combi dispenser giving a final assay concentration of 1 uM Biotin-longer LRRKtide and 10 uM ATP. Test plates were then incubated for 2 hours at room temperature. (Incubation may vary depending on rate and linearity of reaction with different enzyme batches).

4. 6 uL of 'detection solution' containing 200 nM Streptavidin SureLight® APC, 2 nM Eu-W1024 labelled anti-rabbit IgG antibody and 1:500 dilution of Phospho-Ezrin (Thr567)/Radixin (Thr564)/Moesin (Thr558) Polyclonal Antibody in 'stop' assay buffer (50 mM Hepes (pH 7.2), 60 mM EDTA, 10 mM MgCl2, 150 mM NaCl, 5% glycerol and 0.0025% triton X) was added to all wells of the plate using a multidrop combi dispenser. Test plates were then incubated for a further 2 hours at room temperature and then read on a suitable plate reader (Excitation 330 nm, emission 620 nm (Eu) and 665 nm (APC)). Data is analysed using ActivityBase software (IDBS). Dilutions and concentrations of reagents determined on a batch to batch basis Recombinant Cellular LRRK2 AlphaScreen Assay To determine the activity of compounds against LRRK2 kinase activity in cells, the observed LRRK2 kinase-dependent modulation of LRRK2 Ser 935 phosphorylation (Dzamko et al., 2010, Biochem. J. 430: 405-413) was utilized to develop a quantitative 384 well plate-based immunoassay of LRRK2 Ser935 phosphorylation in the human neuroblastoma cell line SH-SY5Y, engineered to over-express recombinant full length LRRK2 protein.

A BacMam virus expressing full length recombinant LRRK2 was purchased from Invitrogen and amplified by inoculation of SF-9 cells at MOI 0.3 for 4-5 days in Sf-900 III SFM medium supplemented with 3% fetal bovine serum. Infected cell cultures were then centrifuged at 2000 g for 20 minutes, viral supernatant titer determined by anti-gp64 plaque assay and stored at 4° C.

Affinity-purified anti-phospho LRRK2 Ser935 sheep polyclonal antibody (Dzamko et al., 2010, Biochem. J. 430: 405-413) was biotinylated by standard methods (PerkinElmer). Anti-LRRK2 rabbit polyclonal antibody was purchased from Novus Biologicals. AlphaScreen Protein A IgG Kit (including acceptor and donor beads) was purchased from Perkin Elmer.

SH-SY5Y cells were grown in DMEM/F12 medium with 10% dialysed fetal bovine serum and harvested by treatment with 0.5% trypsin-EDTA for 5 minutes at 370 C followed by centrifugation at 1000 rpm for 4 minutes. The cell pellet was resuspended in Opti-MEM reduced serum media (Invitrogen) at 200,000 cells/ml and mixed with the BacMam LRRK2 virus at MOI=50. 50 µl cell solutions were then dispensed to each well of a 384-well plate and incubated at 37° C., 5% $CO_2$ for 24 hours.

Serial dilutions of test compounds were prepared in Opti-MEM reduced serum media (Invitrogen) and 5.6 ul transferred from compound plate to cell assay plate to achieve a top final assay concentration of 10 uM. DMSO was used in certain wells as controls. Cells were incubated at 37° C., 5% $CO_2$ for 60 minutes. The medium was then removed and cells lysed by addition of 20 ul cell lysis buffer (Cell Signaling Technology) and incubation at 4° C. for 20 minutes. 10 ul of antibody/acceptor bead mix [(1/1000 biotinylated-pS935 LRRK2 antibody, 1/1000 total-LRRK2 antibody, 1/100 Acceptor beads in AlphaScreen detection buffer (25 mM Hepes (pH 7.4), 0.5% Triton X-100, 1 mg/ml Dextran 500 and 0.1% BSA)] was then added to each well and plates incubated for 2 hours at ambient temperature in the dark. 10 µl of donor beads solution (1/33.3 donor beads in AlphaScreen detection buffer) was then added to each well. Following incubation for a further 2 hours at ambient temperature in the dark, plates were read on an EnVision™ plate reader at emission 520-620 nm with excitation 680 nm. Dose response curve data was based on sigmoidal dose-response model.

Pharmacological Data

Compounds of Examples E1-E66 were tested in the recombinant LRRK2 enzyme peptide substrate TR-FRET assay and/or recombinant cellular LRRK2 alphaScreen assay. Compounds of E1-E66 were found to inhibit LRRK2 kinase activity in either or both assays.

The $pIC_{50}$ value for each compound was either reported in at least one experiment or the average of multiple experiments. It is understood that the data described herein may have reasonable variations depending on the specific conditions and procedures used by the person conducting the experiments.

Compounds of Examples E1-E66 were tested in the recombinant cellular LRRK2 alphaScreen assay and exhibited a $pIC_{50} \geq 5.0$. The compounds of Examples E4, E6, E9, E13, E15, E18, E27, E30-E34, E40, and E59 exhibited $pIC_{50} \geq 7.0$.

The compounds of Examples E1-E31, E33-E36, E39-E44, E46, E47, E51-E53, E56, E61, E63, E64 and E66 were tested in the recombinant LRRK2 enzyme peptide substrate TR-FRET assay and exhibited a $pIC_{50} \geq 5.0$. The compounds of Examples E2-E9, E13, E20, E24, E25, E27, E29, E31, E35, E36, E39-E42, E44, E46, E52, E53, E64 and E66 exhibited $\geq 8.0$.

For example, the pIC50 values of recombinant cellular LRRK2 alphaScreen assay and recombinant LRRK2 enzyme peptide substrate TR-FRET assay for following examples are:

| Example No | recombinant LRRK2 enzyme peptide substrate TR-FRET assay (pIC50) | recombinant cellular LRRK2 alphaScreen assay (pIC50) |
|---|---|---|
| E1 | 7.9 | 6.8 |
| E2 | 8.1 | 6.7 |
| E3 | 8.1 | 6.8 |
| E6 | 8.5 | 7.1 |
| E16 | 7.8 | 6.4 |
| E20 | 8 | 6.7 |
| E24 | 8 | 6.4 |
| E39 | 8.1 | 6.8 |
| E40 | 8 | 7.3 |

What is claimed is:

1. A compound of Formula (I) or a pharmaceutically acceptable salt thereof

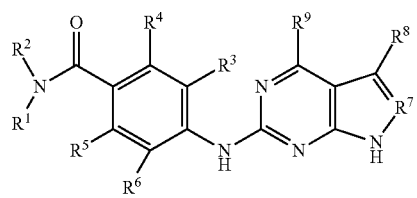

Formula (I)

wherein
$R^1$ is H,
$R^2$ is $C_{1-5}$alkyl optionally substituted with one or more hydroxyl, or
$R^1$ and $R^2$, together with the nitrogen to which they are attached, form:
(1) a nitrogen containing heterocyclic ring, wherein the heterocyclic ring is optionally substituted with one or more substituents independently selected from the group consisting of $C_{1-3}$alkyl, —$CH_2$—$OCH_3$, halo, and piperazin-1-yl optionally substituted with $C_{1-3}$alkyl on the nitrogen at the 4 position, or
(2) a bicyclic ring system selected from the group consisting of

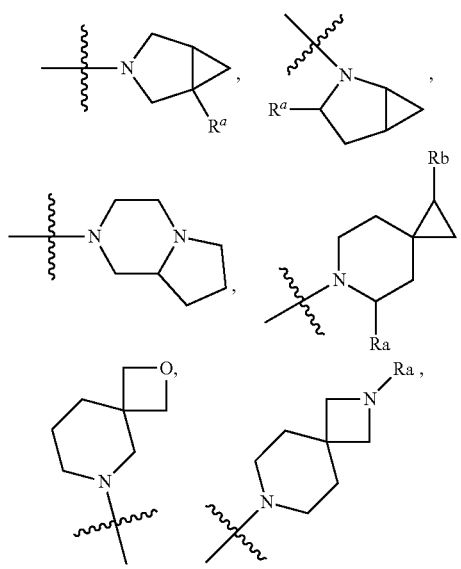

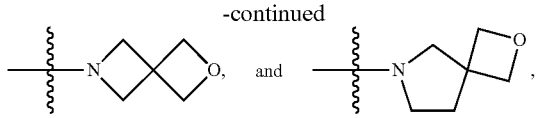

wherein each occurrence of $R^a$ and $R^b$ is independently selected from the group consisting of H, CN, halo, —CH$_2$OCH$_3$, C$_{1-3}$alkoxyl, and C$_{1-3}$alkyl optionally substituted with one hydroxy group;

$R^3$ and $R^5$ are each independently selected from the group consisting of H, C$_{1-3}$alkoxyl, —O—C$_{1-3}$haloalkyl, —O—CH$_2$—C$_{3-6}$cyclalkyl, halo, and —NR$^x$R$^y$, wherein R$^x$ and R$^y$ are each independently H or C$_{1-3}$alkyl;

$R^4$ and $R^5$ are each independently selected from the group consisting of H, halo, C$_{1-3}$alkoxy, and C$_{1-3}$alkyl, $R^7$ is N or CH;

$R^8$ is selected from the group consisting of H, CN, C$_{1-3}$haloalkyl and C$_{1-3}$alkyl; and $R^9$ is selected from the group consisting of C$_{1-3}$alkoxyl, C$_{1-3}$haloalkyl, —O—C$_{1-3}$haloalkyl, and —O—CH$_2$—C$_{3-6}$cycloalkyl, with the proviso that the compound of Formula (I) is not N-propyl-4-[[4-[3,3,3-tris(fluoranyl)propyl]-7H-pyrrolo[2,3-d]pyrimidin-2-yl]amino]benzamide.

2. The compound of Formula (I) or a pharmaceutically acceptable salt thereof according to claim 1, wherein $R^1$ and $R^2$, together with the nitrogen to which they are attached, form a nitrogen containing heterocyclic ring, wherein the heterocyclic ring is selected from the morpholinyl, piperazinyl or piperidinyl, optionally substituted with one or two substituents each independently selected from C$_{1-3}$alkyl.

3. The compound of Formula (I) or a pharmaceutically acceptable salt thereof according to claim 1, wherein $R^1$ and $R^2$, together with the nitrogen to which they are attached, form

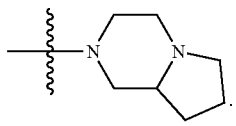

4. The compound of Formula (I) or a pharmaceutically acceptable salt thereof according to claim 1, wherein $R^1$ and $R^2$, together with the nitrogen to which they are attached, form

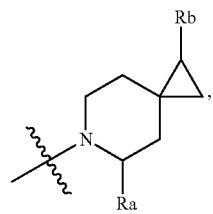

wherein each occurrence of $R^a$ and $R^b$ is independently selected from the group consisting of H, —CH$_2$OCH$_3$, C$_{1-3}$alkoxyl, and —CH$_2$OH.

5. The compound of Formula (I) or a pharmaceutically acceptable salt thereof according to claim 1, wherein $R^3$ and $R^6$ are each independently selected from C$_{1-3}$alkoxyl.

6. The compound of Formula (I) or a pharmaceutically acceptable salt thereof according to claim 1, wherein $R^4$ and $R^5$ are each independently selected from H or F.

7. The compound of Formula (I) or a pharmaceutically acceptable salt thereof according to claim 1, wherein $R^7$ is CH.

8. The compound of Formula (I) or a pharmaceutically acceptable salt thereof according to claim 1, wherein $R^8$ is H.

9. The compound of Formula (I) or a pharmaceutically acceptable salt thereof according to claim 1, wherein $R^9$ is C$_{1-3}$alkoxyl.

10. The compound of Formula (I) or a pharmaceutically acceptable salt thereof according to claim 1, wherein the compound is a compound selected from the group consisting of (4-(4-ethoxy-7H-pyrrolo-[2,3-d]-pyrimidin-2-yl)amino)-3-methoxyphenyl)(morpholino)methanone, (4-((4-ethoxy-7H-pyrrolo-[2,3-d]-pyrimidin-2-yl)amino)-2-fluoro-5-methoxyphenyl(morpholino)methanone, (4-((4-ethoxy-7H-pyrrolo-[2,3-d]-pyrimidin-2-yl)amino)-3-methoxyphenyl)(4-methylpiperazin-1-yl)-methanone, (4-((4-ethoxy-7H-pyrrolo-[2,3-d]pyrimidin-2-yl)amino)-3-methoxyphenyl)(4-(4-methylpiperazin-1-yl)-piperidin-1-yl)-methanone, (4-((4-ethoxy-7H-pyrrolo-[2,3-d]pyrimidin-2-yl)amino-2-fluoro-5-methoxyphenyl)(4-methylpiperazin-1-yl)-methanone, (S)-4-(4-ethoxy-7H-pyrrolo[2,3-d]-pyrimidin-2-yl)amino)-3-methoxyphenyl(hexahydropyrrolo-[1,2-a]-pyrazin-2(1H)-yl)methanone, (3-(difluoromethoxy)-4-((4-ethoxy-7H-pyrrolo-[2,3-d]-pyrimidin-2-yl)amino)phenyl)(4-methylpiperazin-1-yl)-methanone, (3-(cyclopropylmethoxy)-4-((4-ethoxy-7H-pyrrolo-[2,3-d]-pyrimidin-2-yl)amino)phenyl)(4-methylpiperazin-1-yl)-methanone, (4-((4-ethoxy-7H-pyrrolo-[2,3-d]-pyrimidin-2-yl)amino)phenyl)(morpholino)methanone, (4-((4-ethoxy-7H-pyrrolo-[2,3-d]-pyrimidin-2-yl)amino)-3-methoxyphenyl)(2-oxa-6-azaspiro-[3.3]heptan-6-yl)methanone, ((2R,6S)-2,6-dimethylmorpholino)(4-((4-ethoxy-7H-pyrrolo[2,3-d]pyrimidin-2-yl)amino)-3-methoxyphenyl) methanone, (4-((4-ethoxy-7H-pyrrolo-[2,3-d]pyrimidin-2-yl)amino)-3-methoxyphenyl)(2-oxa-6-azaspiro-[3.4]-octan-6-yl)-methanone, (4-((4-ethoxy-7H-pyrrolo-[2,3-d]-pyrimidin-2-yl)amino)-3-methoxyphenyl)(2-methyl-2,7-diazaspiro-[3.5]-nonan-7-yl)methanone, 4-((4-ethoxy-7H-pyrrolo-[2,3-d]pyrimidin-2-yl)amino)-N-(2-hydroxy-2-methylpropyl)-3-methoxybenzamide, (4-((4-ethoxy-7H-pyrrolo-[2,3-d]-pyrimidin-2-yl)amino)phenyl)(4-methylpiperazin-1-yl)methanone, (4-((4-ethoxy-7H-pyrrolo-[2,3-d]-pyrimidin-2-yl)amino)-3-methoxyphenyl)(6-azaspiro-[2.5]octan-6-yl) methanone, (4-((4-ethoxy-7H-pyrrolo-[2,3-d]-pyrimidin-2-yl)amino)-3-methoxyphenyl)(oxazolidin-3-yl) methanone, (4-((4-ethoxy-7H-pyrrolo-[2,3-d]-pyrimidin-2-yl)amino)-2-methoxyphenyl)(morpholino)methanone, (3-(dimethylamino)-4-((4-ethoxy-7H-pyrrolo-[2,3-d]-pyrimidin-2-yl)amino)phenyl)-(morpholino)methanone, (3-ethoxy-4-((4-ethoxy-7H-pyrrolo-[2,3-d]pyrimidin-2-yl)amino)phenyl)(morpholino)methanone,
(4-((4-ethoxy-7H-pyrrolo-[2,3-d]-pyrimidin-2-yl)amino)-3-isopropoxyphenyl)(morpholino)methanone,
(4-((4-ethoxy-7H-pyrrolo-[2,3-d]-pyrimidin-2-yl)amino)-3-fluorophenyl)(4-methylpiperazin-1-yl)methanone,
(3-chloro-4-((4-ethoxy-7H-pyrrolo-[2,3-d]pyrimidin-2-yl)amino)phenyl)(4-methylpiperazin-1-yl)methanone,
(4-((4-ethoxy-7H-pyrrolo-[2,3-d]pyrimidin-2-yl)amino-3-isopropoxyphenyl)(4-methylpiperazin-1-yl)methanone,
(3-ethoxy-4-((4-ethoxy-7H-pyrrolo-[2,3-d]pyrimidin-2-yl)amino)phenyl)(4-methylpiperazin-1-yl)methanone,
(3-(dimethylamino)-4-((4-ethoxy-7H-pyrrolo-[2,3-d]pyrimidin-2-yl)amino)phenyl)(4-methylpiperazin-1-yl)methanone,
(S)-4-((4-ethoxy-7H-pyrrolo-[2,3-d]pyrimidin-2-yl)amino)-3-methoxyphenyl)(3-methylmorpholino)methanone,
(4-((4-ethoxy-7H-pyrrolo-[2,3-d]pyrimidin-2-yl)amino)-3-methoxy-2-methylphenyl)(morpholino)methanone,
(R)-(3,4-dimethylpiperazin-1-yl)-(4-((4-ethoxy-7H-pyrrolo-[2,3-d]pyrimidin-2-yl)amino)-3-methoxyphenyl)methanone,
(R)-(4-((4-ethoxy-7H-pyrrolo[2,3-d]pyrimidin-2-yl)amino-3-methoxyphenyl)(3-methylmorpholino)methanone,
(4-((4-ethoxy-5-methyl-7H-pyrrolo-[2,3-d]pyrimidin-2-yl)amino)-3-methoxyphenyl)(4-methylpiperazin-1-yl)methanone,
(4-((4-ethoxy-5-methyl-7H-pyrrolo-[2,3-d]pyrimidin-2-yl)amino)-3-methoxyphenyl)(morpholino)methanone,
(4-((4-(cyclopropylmethoxy)-7H-pyrrolo-[2,3-d]pyrimidin-2-yl)amino)-3-methoxyphenyl)(4-methylpiperazin-1-yl) methanone,
(4-((4-(cyclopropylmethoxy)-7H-pyrrolo-[2,3-d]pyrimidin-2-yl)amino)-3-methoxyphenyl)(morpholino)methanone,
(R)-(4-((4-ethoxy-7H-pyrrolo-[2,3-d]pyrimidin-2-yl)amino-3-methoxyphenyl)(2-(methoxymethyl)pyrrolidin-1-yl)methanone,
(4-((4-ethoxy-7H-pyrrolo-[2,3-d]pyrimidin-2-yl)amino)-3-methoxyphenyl)(4-fluoropiperidin-1-yl)methanone,
(S-(2,4-dimethylpiperazin-1-yl)(4-((4-ethoxy-7H-pyrrolo-[2,3-d]-pyrimidin-2-yl)amino-3-methoxyphenyl)methanone,
(2-chloro-4-((4-ethoxy-7H-pyrrolo-[2,3-d]pyrimidin-2-yl)amino)-3-methoxyphenyl)(4-methylpiperazin-1-yl)methanone,
(R-(4-((4-ethoxy-7H-pyrrolo-[2,3-d]-pyrimidin-2-yl)amino)-3-methoxyphenyl(hexahydropyrrolo[1,2-a]pyrazin-2(1H)-yl)methanone,
(R)-(2,4-dimethylpiperazin-1-yl)(4-((4-ethoxy-7H-pyrrolo-[2,3-d]-pyrimidin-2-yl)-amino)-3-methoxyphenyl)methanone,
(S)-(3,4-dimethylpiperazin-1-yl)(4-((4-ethoxy-7H-pyrrolo-[2,3-d]-pyrimidin-2-yl)amino)-3-methoxyphenyl)methanone,
(4-((4-ethoxy-7H-pyrrolo-[2,3-d]pyrimidin-2-yl)amino)-3-methoxyphenyl)(4-(methoxymethyl)piperidin-1-yl)methanone,
(S)-(4-((4-ethoxy-7H-pyrrolo-[2,3-d]-pyrimidin-2-yl)amino)-3-methoxyphenyl)(2-(methoxymethyl)pyrrolidin-1-yl)methanone,
(4-((4-ethoxy-7H-pyrrolo-[2,3-d]pyrimidin-2-yl)amino)-3-methoxyphenyl)(2-oxa-6-azaspiro-[3.5]nonan-6-yl)methanone,
(±)-(4-((4-ethoxy-7H-pyrrolo-[2,3-d]-pyrimidin-2-yl)amino)-3-methoxyphenyl)(1-(hydroxymethyl)-3-azabicyclo-[3.1.0]-hexan-3-yl)methanone,
(4-((4-ethoxy-7H-pyrrolo-[2,3-d]-pyrimidin-2-yl)amino)-3-methoxyphenyl)(1-(hydroxymethyl)-3-azabicyclo-[3.1.0]-hexan-3-yl)methanone,
(4-((4-ethoxy-7H-pyrrolo-[2,3-d]-pyrimidin-2-yl)amino)-3-methoxyphenyl)(1-(hydroxymethyl)-3-azabicyclo-[3.1.0]-hexan-3-yl)methanone,
(±)-4-((4-ethoxy-7H-pyrrolo-[2,3-d]-pyrimidin-2-yl)amino)-3-methoxyphenyl)(5-(hydroxymethyl)-6-azaspiro-[2.5]-octan-6-yl)methanone,
(4-((4-ethoxy-7H-pyrrolo-[2,3-d]-pyrimidin-2-yl)amino)-3-methoxyphenyl)(5-(hydroxymethyl)-6-azaspiro[2.5]octan-6-yl)methanone,
(4-((4-ethoxy-7H-pyrrolo-[2,3-d]-pyrimidin-2-yl)amino)-3-methoxyphenyl)(5-(hydroxymethyl)-6-azaspiro[2.5]octan-6-yl)methanone,
(4-((4-ethoxy-7H-pyrrolo-[2,3-d]-pyrimidin-2-yl)amino)-3-methoxyphenyl)(2,7-diazaspiro-[3.5]nonan-7-yl)methanone,
(4-((4-ethoxy-7H-pyrrolo-[2,3-d]-pyrimidin-2-yl)amino)-3-methoxyphenyl)(1-(methoxymethyl)-6-azaspiro-[2.5]-octan-6-yl)methanone,
(R)-4-((4-(cyclopropylmethoxy)-5-methyl-7H-pyrrolo-[2,3-d]-pyrimidin-2-yl)amino)-3-methoxyphenyl)(2,4-dimethylpiperazin-1-yl)methanone,
(4-((4-(cyclopropylmethoxy)-5-methyl-7H-pyrrolo-[2,3-d]-pyrimidin-2-yl)amino)-3-methoxyphenyl)(4-methylpiperazin-1-yl)methanone,
(4-((4-ethoxy-1H-pyrazolo-[3,4-d]-pyrimidin-6-yl)amino)-3-methoxyphenyl)(morpholino)methanone,
(4-((4-ethoxy-3-methyl-1H-pyrazolo-[3,4-d]-pyrimidin-6-yl)amino)-3-methoxyphenyl)(morpholino)methanone,
(4-((4-(cyclopropylmethoxy)-1H-pyrrolo-[3,4-d]pyrimidin-6-yl)amino)-3-methoxyphenyl)(morpholino)methanone,
4-ethoxy-24((2-methoxy-4-(morpholine-4-carbonyl)phenyl)amino)-7H-pyrrolo[2,3-d]pyrimidin-5-carbonitrile,
4-ethoxy-2-((2-isopropoxy-4-(morpholine-4-carbonyl)-phenyl)amino)-7H-pyrrolo-[2,3-d]-pyrimidine-5-carbonitrile,
4-ethoxy-2-((2-isopropoxy-4-(4-methylpiperazine-1-carbonyl)-phenyl)-amino)-7H-pyrrolo-[2,3-d]pyrimidine-5-carbonitrile,
(4-((4-ethoxy-5-(trifluoromethyl)-7H-pyrrolo-[2,3-d]-pyrimidin-2-yl)amino)-3-methoxyphenyl)(morpholino)methanone,
4-ethoxy-2-((4-(4-fluoropiperidine-1-carbonyl)-2-methoxyphenyl)-amino)-7H-pyrrolo-[2,3-d]pyrimidine-5-carbonitrile,
(4-((4-ethoxy-7H-pyrrolo-[2,3-d]pyrimidin-2-yl)amino)-3 methoxyphenyl)-(1-(methoxymethyl)-3-azabicyclo[3.1.0]hexan-3-yl)methanone, and
(1S,3S,5S)-2-(4-((4-ethoxy-7H-pyrrolo-[2,3-d]pyrimidin-2-yl)amino)-3-methoxybenzoyl)-2-azabicyclo-[3.1.0]-hexane-3-carbonitrile,
a free base form, a free acid form or a pharmaceutically acceptable salt thereof.

11. A pharmaceutical composition comprising the compound of Formula (I) or a pharmaceutically acceptable salt thereof according to claim 1; and one or more pharmaceutically acceptable excipients.

12. A method of treatment of Parkinson's disease which comprises administering to a subject in need thereof a therapeutically effective amount of a compound of Formula (I) or a pharmaceutically acceptable salt thereof according to claim 1.

13. The method of claim 12, wherein the subject is human.

* * * * *